US008790691B2

(12) United States Patent
Cullis et al.

(10) Patent No.: US 8,790,691 B2
(45) Date of Patent: Jul. 29, 2014

(54) MODIFIED DRUGS FOR USE IN LIPOSOMAL NANOPARTICLES

(75) Inventors: Pieter Cullis, Vancouver (CA); Marcel Bally, Bowen Island (CA); Marco Ciufolini, Vancouver (CA); Norbert Maurer, Vancouver (CA); Igor Jigaltsev, Vancouver (CA)

(73) Assignee: The University of British Columbia, Vancouver (CA)

( * ) Notice: Subject to any disclaimer, the term of this patent is extended or adjusted under 35 U.S.C. 154(b) by 686 days.

(21) Appl. No.: 12/993,482

(22) PCT Filed: May 26, 2009

(86) PCT No.: PCT/IB2009/006532
§ 371 (c)(1),
(2), (4) Date: Feb. 14, 2011

(87) PCT Pub. No.: WO2009/141738
PCT Pub. Date: Nov. 26, 2009

(65) Prior Publication Data
US 2011/0165225 A1    Jul. 7, 2011

Related U.S. Application Data

(60) Provisional application No. 61/055,929, filed on May 23, 2008.

(51) Int. Cl.
| A61K 9/127 | (2006.01) |
| C07D 405/12 | (2006.01) |
| C07D 413/12 | (2006.01) |
| C07D 305/14 | (2006.01) |
| C07J 43/00 | (2006.01) |
| C07J 41/00 | (2006.01) |
| C07D 493/04 | (2006.01) |
| C07D 498/16 | (2006.01) |
| C07K 7/64 | (2006.01) |
| A61K 31/496 | (2006.01) |
| A61K 31/5377 | (2006.01) |
| A61K 31/4523 | (2006.01) |
| A61K 31/337 | (2006.01) |
| A61K 31/58 | (2006.01) |
| A61K 31/573 | (2006.01) |
| A61K 38/13 | (2006.01) |
| B82Y 5/00 | (2011.01) |

(52) U.S. Cl.
USPC ........... 424/450; 544/375; 544/147; 544/380; 544/377; 546/196; 549/510; 540/456; 552/575; 530/321; 514/254.11; 514/232.8; 514/320; 514/449; 514/176; 514/179; 514/253.03; 514/205; 977/773; 977/798; 977/907

(58) Field of Classification Search
None
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| 4,737,323 A | 4/1988 | Martin et al. |
| 4,837,028 A | 6/1989 | Allen |
| 4,942,184 A | 7/1990 | Haugwitz et al. |
| 4,960,790 A | 10/1990 | Stella et al. |
| 5,316,771 A | 5/1994 | Barenholz et al. |
| 5,475,011 A | 12/1995 | Ojima et al. |
| 5,489,589 A | 2/1996 | Wittman et al. |
| 5,547,981 A | 8/1996 | Greenwald et al. |
| 5,622,986 A | 4/1997 | Greenwald et al. |
| 6,472,507 B1 | 10/2002 | Fischer et al. |
| 6,482,850 B2 | 11/2002 | Ali et al. |
| 6,855,720 B2 | 2/2005 | Yang |
| 2007/0116753 A1 | 5/2007 | Hong et al. |
| 2008/0153899 A1 | 6/2008 | Swindell et al. |

FOREIGN PATENT DOCUMENTS

| CN | 101029034 A | 9/2007 |
| EP | 0 320 988 | 6/1989 |
| EP | 0 569 281 | 11/1993 |

OTHER PUBLICATIONS

Immordino M, Preparation, characterization, cytotoxicity and pharmacokinetics of liposomes containing docetaxel, JCR, 2003, 91, 417-429.*
Adlakha-Hutcheon et al., "Controlled destabilizsation of a liposomal drug delivery system enhances mitoxantrone antitumor activity", Nature Biotechnology, 17, 1999, pp. 775-779.
Baldwin et al., "Rules for Ring Closure: Ring Formation by Conjugate Addition of Oxygen Nucleophiles", J. Org. Chem., 43(24), 1977, pp. 3846-3852.
Baldwin, "Rules for Ring Closure", JCS Chem. Comm., 1976, pp. 734-736.
Bowman et al., Liposomal Vincristine Which Exhibits Increased Drug Retention and Increased Circulation Longevity Cures Mice Bearing P388 Tumors, Cancer Research, 54, 1994, pp. 2830-2833.

(Continued)

Primary Examiner — Frederick Krass
Assistant Examiner — Celeste A Roney
(74) Attorney, Agent, or Firm — Kilpatrick Townsend & Stockton LLP

(57) ABSTRACT

Drag derivatives are provided herein which are suitable for loading into liposomal nanoparticle carriers. In some preferred aspects, the derivatives comprise a poorly water-soluble drag derivatized with a weak-base moiety that facilitates active loading of the drag through a LN transmembrane pH or ion gradient into the aqueous interior of the LN. The weak-base moiety can optionally comprise a lipophilic domain that facilitates active loading of the drag to the inner monolayer of the liposomal membrane. Advantageously, LN formulations of the drag derivatives exhibit improved solubility, reduced toxicity, enhanced efficacy, and/or other benefits relative to the corresponding free drags.

17 Claims, 10 Drawing Sheets

(56) References Cited

OTHER PUBLICATIONS

Capdeville et al., "Glivec (STI571, IMATINIB), A Rationally Developed, Targeted Anticancer Drug", Nature Reviews, Drug Discovery, 1, 2002, pp. 493-502.
Cheung et al., "Loading of doxorubicin into liposomes by forming $Mn^{2+}$-drug complexes", Biochimica et Biophysica Acta, 1414, 1998, pp. 205-216.
Cullis et al., "Influence of pH gradients on the transbilayer transport of drugs, lipids, peptides and metal ions into large unilamellar vesicles", Biochimica et Biophysica Acta, 1331, 1997, pp. 187-211.
Cullis et al., "Lipid Polymorphism and the Functional Roles of Lipids in Biological Membranes,"Biochimica et Biophysica Acta, 559, 1979, pp. 399-420.
Drummond et al., "Optimizing Liposomes for Delivery of Chemotherapeutic Agents to Solid Tumors", Pharmacological Reviews, 51(4), 1999, pp. 691-743.
Du et al., "Synthsis and evaluation of water-soluble docetaxel prodrugs-docetaxel esters of malic acid", Bioorganic & Medicinal Chemistry, 15, 2007, pp. 6323-6330.
Fenske et al., "Ionophore-mediated uptake of ciprofloxacin and vincristine into large unilamellar vesicles exhibiting transmembrance ion gradients", Biochimica et Biophysica Acta, 1414, 1998, pp. 188-204.
Fenske et al., "Encapsulation of weakly-basic drugs, antisense oligonucleotides, and plasmid DNA within large unilamellar vesicles for drug delivery applications", Liposomes, Second Edition, A Practical Approach, Torchilin and Weissig Editors, 2003, Ch. 6, pp. 167-191.
Fields et al., "Dual-attribute continuous monitoring of cell proliferation/cytotoxicity", Supplied by the British Library, American Biotechnology Laboratory, 1993, pp. 48-50.
Fiske et al., "The Colorimetric Determination of Phosphorus", The Journal of biological Chemistry, vol. LXVI, No. 2, 1925, pp. 375-400.
Gabizon et al., "Development of liposomal anthracyclines: from basics to clinical applications", Journal of controlled Release, 53, 1998, pp. 275-279.
Ganesh, "Improved biochemical strategies for targeted delivery of taxoids", Bioorganic & Medicinal chemistry, 15, 2007, pp. 3597-3623.
Haran et al., "Transmembrane ammonium sulfate gradients in liposomes produce efficient and stable entrapment of amphipathic weak bases", Biochimica et Biophysica Acta, 1151, 1993, pp. 201-215.
Hobbs et at "Regulation of transport pathways in tumor vessels: Role of tumor type and microenvironment", Proc. Natl. Acad. Sci., 95, 1998, pp. 4607-4612.
Hope et al., "Generation of Multilamellar and Unilamellar Phospholipid Vesicles", Chemistry and Physics of Lipids, 40, 1986, pp. 89-107.
Hope et al., "production of large unilamellar vesicles by a rapid extrusion procedure. Characterization of size distribution . . . " Biochimica et Biophysica Acta, 812, 1985, pp. 55-65.
Jain, "Delivery of molecular and cellular medicine to solid tumors", Journal of Controlled Release, 53, 1998, pp. 49-67.
Koning et al., "Selective transfer of a lipophilic prodrug of 5-fluorodeoxyuridine from immunoliposomes to colon cancer cells", Biochimica et Biophysica Acta, 1420, 1999, pp. 153-167.
Madden et al., "The accumulation of drugs within large unilamellar vesicles exhibiting a proton gradient: a survey", Chemistry and Physics of Lipids, 53, 1990, pp. 37-46.
Martin et al., "The Design of Cationic Lipids for Gene Delivery", Current Pharmaceutical Design, 2005, 11, pp. 375-394.
Maurer et al., "Developments in liposomal drug delivery systems", Expert Opin. Biol. Ther., 1(6), 2001, pp. 923-947.
Mishra et al., "Studies in Nucleosides: Part XVI-Synthesis of Azathioprine Analogues", Indian Journal of chemistry, vol. 26B, 1987, pp. 847-850.
Nakayama et al., "Letters to the Editors: Assessment of the Alamar Blue assay for cellular growth and viability in vitro", Journal of Immunological Methods, 204, 1997, pp. 205-208.
Ostro editor, Liposomes, Marcel Dekker Inc., New York, 1983, Ch. 1, "Liposome Preparation: Methods and Mechanisms", pp. 27-51.
Pick, "Liposomes with a Large Trapping Capacity Prepared by Freezing and Thawing of Sonicated Phospholipid Mixtures", Archives of Biochemistry and Biophysics, 212(1), 1981, pp. 186-194.
Pizzolato et al., "The camptothecins", New Drug Classes, The Lancet, 361, 2003, pp. 2235-2242.
Plowman et al., Teicher BA Editor, Anticancer drug development guide: Preclinical screening, clinical trials, and approval., "Human Tumor Xenograft Models in NCI Drug Development", 1997, pp. 101-125.
Pop et al., "Derivatives of Dexanabinol. II. Salts of Amino Acid Esters Containing Tertiary and Quaternary Heterocyclic Nitrogen with Increased Water-Solubility", Pharmaceutical Research, 13(3), 1996, pp. 469-475.
Rautio et al., "Synthesis and in vitro Evaluation of Novel Morpholinyl- and Methylpiperazinylacloxyalkyl Prodrugs . . . ", J. Med. Chem., 43, 2000, pp. 1489-1494.
Semple et al., "Optimization and characterization of a Sphingomyelin/Cholesterol Liposome Formulation . . . ", J. of Pharmaceutical Sciences. 94(5), 2005, pp. 1024-1038.
Shan et al., "Preferential extravasation and accumulation of liposomal vincristine in tumor comparing to normal tissue enhances antitumor activity", Cancer Chemother Pharmacol, 58, 2006, pp. 245-255.
Soepenberg et al., "Real-time pharmacokinetics guiding clinical decisions: phase I study of a weekly schedule of liposome . . . ", European Journal of Cancer, 40, 2004, pp. 681-688.
Szoka et al., "Comparative Properties and Methods of Preparation of Lipid Vesicles (Liposomes)", Ann. Rev. Biophys. Bioeng., 9, 1980, pp. 467-508.
Waterhouse et al., "Preparation, Chacterization, and biological Analysis of Liposomal Formulations of Vincristine", Methods in enzymology, 391, 2005, 2, pp. 40-57.
Webb et al., "Sphingomyelin-cholesterol liposomes significantly enhance the pharmacokinetic and thereapeutic properties of vincristine in murine and human tumour models", British Journal of Cancer, 72, 1995, pp. 896-904.
Working et al., "Reduction of the Cariotoxicity of Doxorubicin in Rabbits and Dogs by encapsulation in Long-Circulating, Pegylated Liposomes", The Journal of Pharmacology and Experimental Therapeutics, 1999, 289(2), pp. 1128-1133.

* cited by examiner pH 7.4

Plasma

A.

B.

A.

B.

A.

B.

C.

MODIFIED DRUGS FOR USE IN LIPOSOMAL NANOPARTICLES

CROSS-REFERENCE TO RELATED APPLICATION

The present application claims the benefit of U.S. provisional patent application No. 61/055,929, filed May 23, 2008, which is herein incorporated by reference in its entirety.

FIELD OF THE INVENTION

The present invention relates generally to methods of chemically modifying drugs that are resistant or incapable of being encapsulated in liposomes to form derivatives that can be efficiently loaded into liposomal nanoparticles (LN) exhibiting a transmembrane pH or ion gradient. In some preferred aspects, the derivatives are pro-drugs that are readily converted to the free drug upon release from the LN. The invention also relates to drug derivatives made according to methods of the invention, LN formulations and pharmaceutical compositions comprising such derivatives, and methods of making and using the same.

BACKGROUND

Many existing drug discovery strategies are predicated on finding 'druggable' compounds that are water-soluble and bioavailable. As a result, newly discovered compounds with poor solubility and limited bioavailability rarely advance to lead status, often despite having promising therapeutic properties.

A variety of drug formulations and delivery methods have been developed in an effort to overcome the limitations of non-druggable compounds. Liposomal nanoparticles (LN) are a leading drug delivery system for the systemic (intravenous) administration of drugs, and there are a number of liposomal drugs currently on the market and in clinical trials. LN generally have low toxicity and can be designed to provide a wide range of beneficial pharmaceutical properties, such as improved serum half-life, bioavailability, permeability, and the like. LN formulations have been particularly successful in connection with chemotherapeutic agents, which have limited efficacy when administered in their conventional (free) form due to their low aqueous solubility, short serum half-life, and indiscriminate accumulation in normal and disease tissues alike.

Long-circulating LN typically have diameters of about 100 nm or less, and remain in the blood circulation for extended periods of time. The extended lifespan of long-circulating LN allows them to accumulate at or near sites of infection, inflammation, tumor growth, and other disease-associated drug targets. This accumulation is facilitated by the local structure of the vasculature in these regions (referred to as "leaky" vasculature), characterized by large pores through which liposomes can reach therapeutic targets (Jain, Microcirculation, 4: 1-23 (1997), Hobbs et al., Proc. Natl. Acad. Sci. USA, 95: 4607-4612 (1998)). Stable association of a chemotherapeutic agent or other drug with long-circulating LN can therefore increase the amount of the drug that reaches therapeutic targets, prolong the exposure of the targets to therapeutic levels of the drug through controlled (sustained) release from the LN, and reduce accumulation in healthy, non-targeted tissues, thereby increasing effectiveness and reducing toxicity. In the case of solid tumors, LN formulations of chemotherapeutic agents have yielded dramatic improvements in therapeutic index, tolerability, efficacy, and other properties, in both animal models and clinical studies.

The application of LN technology to a drug of interest requires the drug to be amenable to being loaded in a liposomal carrier and released at an appropriate rate at or near therapeutic targets. The ability to load a drug into liposomes depends on the chemical properties of the drug, the liposomal membrane, and the interior environment of the liposome. In general, both water soluble and lipid soluble drugs can be loaded into liposomes using passive loading techniques that rely on the association of water soluble drugs with the polar phospholipids lining the inner liposomal membrane and/or the aqueous liposomal interior, and the association of lipid soluble drugs with the lipid bilayer. However, many useful drugs have more complex solubility profiles that are less amenable to passive loading methods.

One approach for loading poorly soluble drugs into liposomes is to modify the drug to facilitate passive loading. For example, liposomal formulations have been developed in which taxanes are modified by the addition of a hydrocarbon chain containing an electronegative "hydrolysis-promoting group" (HPG) to form fatty acid derivatives with enhanced solubility in the lipid bilayer, as described in U.S. Pat. No. 6,482,850 and related applications. However, passive loading methods generally have poor loading efficiencies and produce liposomes with poor drug retention and release, limiting the utility of the resulting formulations.

To overcome limitations related to passive loading, several active loading techniques have been developed that allow drugs to be loaded with high efficiency and retention. A particularly effective approach involves loading of drugs that are weak bases by forming a pH gradient across the liposomal membrane to produce liposomes with an acidic liposomal interior and an exterior environment with higher pH than the liposome interior (e.g. neutral pH) (e.g., Maurer, N., Fenske, D., and Cullis, P. R. (2001) Developments in liposomal drug delivery systems. Expert Opinion in Biological Therapy 1, 923-47; Cullis et al., Biochim Biophys Acta., 1331: 187-211 (1997); Fenske et al., Liposomes: A practical approach. Second Edition. V. Torchilin and V. Weissig, eds., Oxford University Press, p. 167-191 (2001)). Weakly basic drugs can exist in two co-existing (equilibrium) forms; a charge-neutral (membrane-permeable) form and a charged/protonated (membrane impermeable) form. The neutral form of the drug will tend to diffuse across the liposome membrane until the interior and exterior concentrations are equal. However, an acidic interior environment results in protonation of the neutral form, thereby driving continued uptake of the compound trapping it in the liposome interior. Another approach involves the use of metal ion gradients (e.g. Cheung B C, Sun T H, Leenhouts J M, Cullis P R: Loading of doxorubicin into liposomes by forming $Mn^{2+}$-drug complexes. Biochim Biophys Acta (1998) 1414:205-216). The metal ion concentration is high in the liposome interior; the exterior environment is metal ion free. This loading method relies the same basic principles as the pH gradient technique. The neutral form of the weak base drug can permeate across the membrane and is retained in the aqueous interior of the liposomes through formation of a drug-metal ion complex. In this case drug-metal ion complex formation drives the continued uptake of the drug.

Some anticancer and antimicrobial drugs, such as vincristine, vinorelbine, doxorubicin, ciprofloxacin and norfloxacin, can be readily loaded and stably retained in LN using pH gradient active loading techniques (e.g., Drummond et al., Pharmacol. Rev., 51: 691-743 (1999), Cullis et al., Biochim Biophys Acta., 1331: 187-211 (1997); Semple et al., J.

Pharm. Sci., 94(5): 1024-38 (2005)). However, a number of clinically important drugs are not weak bases and are thus not amenable to such active loading techniques (e.g., Soepenberg et al., European J. Cancer, 40: 681-688 (2004)). For example, many anticancer drugs, including certain taxane-based drugs (e.g., paclitaxel and docetaxel), and podophyllotoxin derivatives (e.g., etoposide) cannot readily be formulated as LN using standard methods.

Taxotere® (docetaxel) and Taxol® (paclitaxel) are the most widely prescribed anticancer drugs on the market, and are associated with a number of pharmacological and toxicological concerns, including highly variable (docetaxel) and non-linear (paclitaxel) pharmacokinetics, serious hypersensitivity reactions associated with the formulation vehicle (Cremophor EL, Tween 80), and dose-limiting myelosuppression and neurotoxicity. In the case of Taxotere®, the large variability in pharmacokinetics causes significant variability in toxicity and efficacy, as well as hematological toxicity correlated with systemic exposure to the unbound drug. In addition, since the therapeutic activity of taxanes increases with the duration of tumor cell drug exposure, the dose-limiting toxicity of commercial taxane formulations substantially limits their therapeutic potential.

Accordingly, there is a need in the art for strategies to enable a wide variety of drugs to be formulated as LN and thus realize the benefits of liposomal delivery technology.

SUMMARY

In one aspect, a drug derivative of formula I is provided:

wherein
 D is a drug;
 n is 1, 2, or 3; and
 Z is a Liposome Solubilization Unit of formula II:

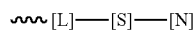

wherein
  [L] is a Linker selected from the group consisting of: carboxy, carboxyamido, and alkyl silyl.
  [S] is a Spacer selected from the group consisting of: $C_1$-$C_{10}$ alkyl, $C_2$-$C_{10}$ alkenyl, and $C_2$-$C_{10}$ alkynyl, each optionally substituted with one or more substituents selected from the group consisting of: halo; $C_1$-$C_{10}$ alkyl; cycloalkyl; and —$YR^2$, wherein
   Y is a heteroatom selected from the group consisting of: N, O, S, and Si, and
   $R^2$ is selected from the group consisting of: H; a heteroatom selected from the group consisting of N, O, and S; $C_1$-$C_{10}$ alkyl; and cycloalkyl, each optionally substituted with halo;
  $C_1$-$C_{10}$ heteroalkyl, optionally substituted one or more times with—$YR^2$, wherein
   Y is a heteroatom selected from the group consisting of N, O, S, and Si, and
   $R^2$ is selected from the group consisting of: H; a heteroatom selected from the group consisting of: N, O, and S; $C_1$-$C_{10}$ alkyl; and cycloalkyl, each optionally substituted with halo; and
  cycloalkyl, heterocyclyl, aryl, and heteroaryl, each optionally substituted with halo; and
 [N] is a Solubilization Domain of the general formula III:

wherein
  R and R' are independently selected from the group consisting of: H; $C_1$-$C_{10}$ alkyl, $C_2$-$C_{10}$ alkenyl, $C_2$-$C_{10}$ alkynyl, each optionally substituted with halo; cycloalkyl, heterocyclyl, aryl, and heteroaryl, each optionally substituted with halo; and a protonable nitrogen-containing heterocyclic system; or
  R and R' together with the nitrogen atom to which they are attached form a heterocyclic ring having four to five carbon atoms, which may comprise one of multiple rings within a ring system.

In some aspects, [N] has a pKa of at least about 5.5.
In further aspects, [N] has a pKa less than or equal to about 12.0.

In some aspects, the drug derivative is suitable to be actively loaded into liposomal nanoparticles having an aqueous interior.

In further aspects, the drug derivative is suitable to be actively loaded into the aqueous interior of the liposomal nanoparticles. In some aspects, the aqueous interior of the liposomal nanoparticles has an acidic pH relative to the external medium. In further aspects, the drug derivative is protonated within the aqueous interior of the liposomal nanoparticles.

In other aspects, the drug derivative is suitable to be actively loaded so that the drug derivative resides within or is stably associated with the liposomal nanorparticle membrane. In some of these aspects, [N] is selected from a group of formula IVa or IVb:

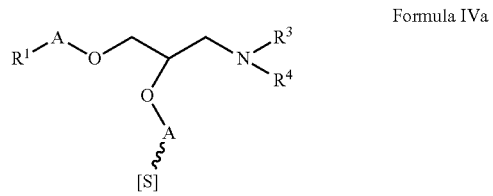

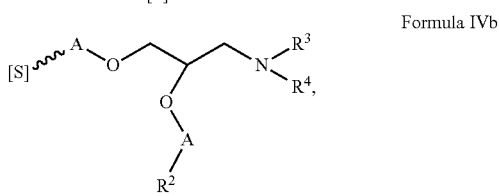

wherein:
  A is selected from the group consisting of: carbonyl, methylene, and NR—C=O, where R is H or $C_1$-$C_5$ alkyl;

R[1] and R[2] are independently selected from the group consisting of: linear or branched $C_1$-$C_{30}$ alkyl, $C_2$-$C_{30}$ alkenyl, and $C_2$-$C_{30}$ alkynyl; and R[3] and R[4] are independently selected from the group consisting of: H; $C_1$-$C_{10}$ alkyl, $C_2$-$C_{10}$ alkenyl, $C_2$-$C_{10}$ alkynyl, each optionally substituted with halo; and cycloalkyl, heterocyclyl, aryl, and heteroaryl, each optionally substituted with halo; or R[3] and R[4] together with the nitrogen atom to which they are attached form a heterocyclic ring having four to five carbon atoms, which may comprise one of multiple rings within a ring system.

Also provided herein is a liposomal nanoparticle formulation of a drug derivative provided herein. In some aspects, the liposomal nanoparticle formulation is formed by actively loading the drug derivative into liposomal nanoparticles having an aqueous interior.

In further aspects, the drug derivative resides within the aqueous interior of the liposomal nanoparticles. In some aspects, the aqueous interior of the liposomal nanoparticles has an acidic pH relative to the external medium. In further aspects, the drug derivative is protonated within the aqueous interior of the liposomal nanoparticles.

In yet further aspects, the drug derivative resides within or is stably associated with the liposomal nanoparticle membrane. In further aspects, [N] is a group of formula IVa or IVb:

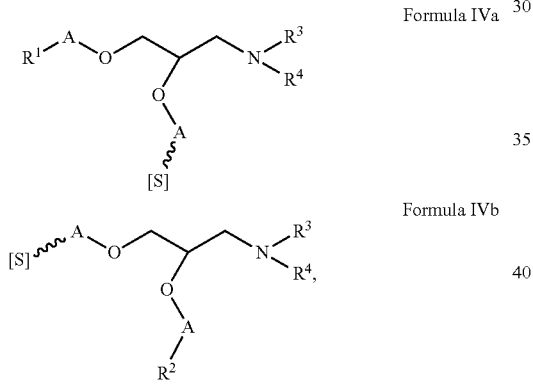

wherein:

A is selected from the group consisting of: carbonyl, methylene, and NR—C═O, where R is H or $C_1$-$C_5$ alkyl;

R[1] and R[2] are independently selected from the group consisting of: linear or branched $C_1$-$C_{30}$ alkyl, $C_2$-$C_{30}$ alkenyl, and $C_2$-$C_{30}$ alkynyl; and R[3] and R[4] are independently selected from the group consisting of: H; $C_1$-$C_{10}$ alkyl, $C_2$-$C_{10}$ alkenyl, $C_2$-$C_{10}$ alkynyl, each optionally substituted with halo; and cycloalkyl, heterocyclyl, aryl, and heteroaryl, each optionally substituted with halo; or R[3] and R[4] together with the nitrogen atom to which they are attached form a heterocyclic ring having four to five carbon atoms, which may comprise one of multiple rings within a ring system.

In another aspect, a pharmaceutical composition is provided herein comprising a liposomal nanoparticle formulation of a drug derivative provided herein and a pharmaceutically acceptable excipient.

In an additional aspect, a method of modifying a drug to facilitate loading of the drug into LN is provided herein, the method comprising conjugating a Liposome Solubilization Unit (Z) of formula II to the drug

wherein

[L] is a Linker selected from the group consisting of: carboxy, carboxyamido, and alkyl silyl.

[S] is a Spacer selected from the group consisting of:
$C_1$-$C_{10}$ alkyl, $C_2$-$C_{10}$ alkenyl, and $C_2$-$C_{10}$ alkynyl, each optionally substituted with one or more substituents selected from the group consisting of: halo; $C_1$-$C_{10}$ alkyl; cycloalkyl; and —YR[2], wherein
Y is a heteroatom selected from the group consisting of: N, O, S, and Si, and
R[2] is selected from the group consisting of: H; a heteroatom selected from the group consisting of N, O, and S; $C_1$-$C_{10}$ alkyl; and cycloalkyl, each optionally substituted with halo;
$C_1$-$C_{10}$ heteroalkyl, optionally substituted one or more times with —YR[2], wherein
Y is a heteroatom selected from the group consisting of N, O, S, and Si, and
R[2] is selected from the group consisting of: H; a heteroatom selected from the group consisting of: N, O, and S; $C_1$-$C_{10}$ alkyl; and cycloalkyl, each optionally substituted with halo; and
cycloalkyl, heterocyclyl, aryl, and heteroaryl, each optionally substituted with halo; and

[N] is a Solubilization Domain of the general formula III:

wherein

R and R' are independently selected from the group consisting of: H; $C_1$-$C_{10}$ alkyl, $C_2$-$C_{10}$ alkenyl, $C_2$-$C_{10}$ alkynyl, each optionally substituted with halo; cycloalkyl, heterocyclyl, aryl, and heteroaryl, each optionally substituted with halo; and a protonable nitrogen-containing heterocyclic system; or R and R' together with the nitrogen atom to which they are attached form a heterocyclic ring having four to five carbon atoms, which may comprise one of multiple rings within a ring system.

In still additional aspects, a method of loading a drug into liposomal nanoparticles is provided herein, the method comprising the steps of conjugating a Liposome Solubilization Unit (Z) of formula II to the drug to form a drug derivative; and actively loading the drug derivative into liposomal nanoparticles having an aqueous interior wherein formula II is:

[L] is a Linker selected from the group consisting of: carboxy, carboxyamido, and alkyl silyl.

[S] is a Spacer selected from the group consisting of:
C$_1$-C$_{10}$ alkyl, C$_2$-C$_{10}$ alkenyl, and C$_2$-C$_{10}$ alkynyl, each optionally substituted with one or more substituents selected from the group consisting of: halo; C$_1$-C$_{10}$ alkyl; cycloalkyl; and —YR$^2$, wherein
Y is a heteroatom selected from the group consisting of: N, O, S, and Si, and
R$^2$ is selected from the group consisting of: H; a heteroatom selected from the group consisting of N, O, and S; C$_1$-C$_{10}$ alkyl; and cycloalkyl, each optionally substituted with halo;
C$_1$-C$_{10}$ heteroalkyl, optionally substituted one or more times with —YR$^2$, wherein
Y is a heteroatom selected from the group consisting of N, O, S, and Si, and
R$^2$ is selected from the group consisting of: H; a heteroatom selected from the group consisting of: N, O, and S; C$_1$-C$_{10}$ alkyl; and cycloalkyl, each optionally substituted with halo; and
cycloalkyl, heterocyclyl, aryl, and heteroaryl, each optionally substituted with halo; and
[N] is a Solubilization Domain of the general formula III:

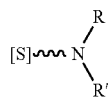

wherein
R and R' are independently selected from the group consisting of: H; C$_1$-C$_{10}$ alkyl, C$_2$-C$_{10}$ alkenyl, C$_2$-C$_{10}$ alkynyl, each optionally substituted with halo; cycloalkyl, heterocyclyl, aryl, and heteroaryl, each optionally substituted with halo; and a protonable nitrogen-containing heterocyclic system; or
R and R' together with the nitrogen atom to which they are attached form a heterocyclic ring having four to five carbon atoms, which may comprise one of multiple rings within a ring system.

In some aspects, the drug derivative is actively loaded into the aqueous interior of the liposomal nanoparticles. In further aspects, the aqueous interior of the liposomal nanoparticles has an acidic pH relative to the external medium. In yet further aspects, the drug derivative is protonated within the aqueous interior of the liposomal nanoparticles.

In some aspects, the drug derivative is actively loaded so that it resides within or is stably associated with the liposomal nanoparticle membrane. In further aspects, [N] is a group of formula IVa or IVb:

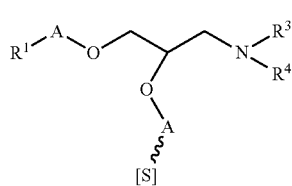

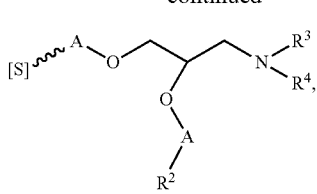

wherein:
A is selected from the group consisting of: carbonyl, methylene, and NR—C═O, where R is H or C$_1$-C$_5$ alkyl;
R$^1$ and R$^2$ are independently selected from the group consisting of: linear or branched C$_1$-C$_{30}$ alkyl, C$_2$-C$_{30}$ alkenyl, and C$_2$-C$_{30}$ alkynyl; and
R$^3$ and R$^4$ are independently selected from the group consisting of: H; C$_1$-C$_{10}$ alkyl, C$_2$-C$_{10}$ alkenyl, C$_2$-C$_{10}$ alkynyl, each optionally substituted with halo; and cycloalkyl, heterocyclyl, aryl, and heteroaryl, each optionally substituted with halo; or
R$^3$ and R$^4$ together with the nitrogen atom to which they are attached form a heterocyclic ring having four to five carbon atoms, which may comprise one of multiple rings within a ring system.

In yet another aspect, a method is provided for treating a disease or condition, comprising administering an effective amount of a pharmaceutical composition described herein to a patient in need of treatment.

DETAILED DESCRIPTION

Figure 1:
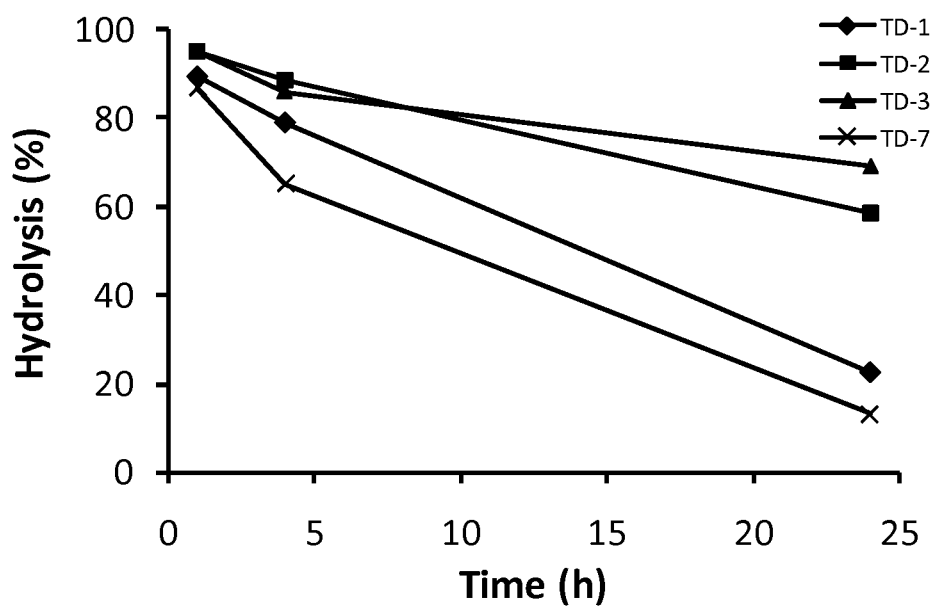
FIG. 1. Kinetics of prodrug hydrolysis in pH 7.4 aqueous buffer and phosphate-buffered mouse plasma (pH 7.4) at 37° C.
Figure 1:
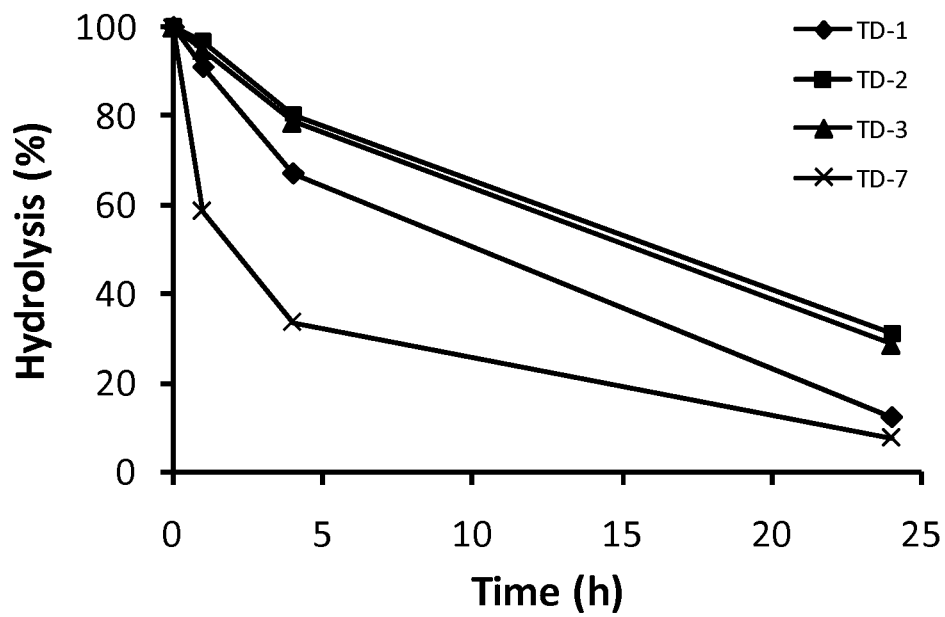

As used herein, the term "liposome" or "liposomal nanoparticle" or "LN" refers to a self-assembling structure comprising one or more lipid bilayers, each of which comprises two monolayers containing oppositely oriented amphipathic lipid molecules. Amphipathic lipids comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups are oriented towards the bilayer's surface and acyl chains are oriented towards the interior of the bilayer, effectively shielding the acyl chains from contact with the aqueous environment.

Liposomes useful in connection with the methods and compositions described herein can have a single lipid bilayer (unilamellar liposomes) or multiple lipid bilayers (multilamellar liposomes) surrounding or encapsulating an aqueous compartment. Various types of liposomes are described, e.g., in Cullis et al., *Biochim. Biophys Acta*, 559: 399-420 (1987).

Amphipathic lipids typically comprise the primary structural element of liposomal lipid vesicles. Hydrophilic characteristics of lipids derive from the presence of phosphato, carboxylic, sulfato, amino, sulfhydryl, nitro, and other like polar groups. Hydrophobicity can be conferred by the inclusion of groups that include, but are not limited to, long chain saturated and unsaturated aliphatic hydrocarbon groups, which may be substituted by one or more aromatic, cycloaliphatic or heterocyclic group(s). Examples of preferred amphipathic compounds are phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, distearoylphosphatidylcholine (DSPC), dilinoleoylphosphatidylcholine and egg sphingomyelin. Other lipids such as sphingolipids and glycosphingolipids, are also useful in methods and compositions provided herein. Additionally, the amphipathic lipids described above may be mixed with other lipids, such as triacylglycerols and sterols.

As used herein, the term "$C_{1-10}$-alkyl" refers to a linear or branched saturated hydrocarbon chain wherein the longest chain has from one to ten carbon atoms, such as methyl, ethyl, n-propyl, isopropyl, n-butyl, isobutyl, sec-butyl, tert-butyl, pentyl, isopentyl, neopentyl, hexyl, etc.

As used herein, the term "$C_{2-10}$-alkenyl" means a linear or branched hydrocarbon group having from two to ten carbon atoms and containing one or more double bonds. Non-limiting examples of $C_{2-10}$-alkenyl groups include allyl, homoallyl, vinyl, crotyl, butenyl, pentenyl, hexenyl, heptenyl, octenyl, etc. Non-limiting examples of $C_{2-10}$-alkenyl groups with more than one double bond include butadienyl, pentadienyl, hexadienyl, heptadienyl, heptatrienyl, octatrienyl, etc. groups as well as branched forms of these. The position of the unsaturation (the double bond) may be at any position along the carbon chain.

As used herein, the term "$C_{2-10}$-alkynyl" refers a linear or branched hydrocarbon group containing from two to eight carbon atoms and containing one or more triple bonds. Non-limiting examples of $C_{2-10}$-alkynyl groups include ethynyl, propynyl, butynyl, pentynyl, hexynyl, heptynyl, octynyl, etc. groups as well as branched forms of these. The position of unsaturation (the triple bond) may be at any position along the carbon chain. More than one bond may be unsaturated such that the "$C_{2-10}$-alkynyl" is a di-yne or enedi-yne.

As used herein, the term "heteroalkyl" indicates an alkane group containing 1 or more, and preferably 1 or 2, heteroatoms selected from O, S and N. Where present, such heteroatoms are optionally further substituted by a heteroatom selected from O, S, N, and Si, or an alkyl, alkenyl, alkynyl, cycloalkyl, aryl, or heteroaryl group optionally substituted with halo. Non-limiting examples include (one or more) ether, thioether, ester and amide groups.

As used herein, the terms "aryl" and "cycloalkyl" refer to mono- and bicyclic ring structures comprising 5 to 12 carbon atoms, and preferably to monocyclic rings comprising 5 to 6 carbon atoms. Where such rings comprise one or more heteroatoms, selected from N, S and O, (i.e., heterocyclic, or heteroaryl rings) such rings comprise a total of 5 to 12 atoms, more preferably 5 to 6 atoms. Heterocyclic rings include, but are not limited to, furyl, pyrrolyl, pyrazolyl, thienyl, imidazolyl, indolyl, benzofuranyl, benzothiophenyl, indazolyl, benzoimidazolyl, benzothiazolyl, isoxazolyl, oxazolyl, thiazolyl, isothiazolyl, pyridyl, piperidinyl, piperazinyl, pyridazinyl, pyrimidinyl, pyrazinyl, morpholinyl, oxadiazolyl, thiadiazolyl, imidazolinyl, imidazolidinyl and the like. The ring may be substituted with one or more heteroatoms selected from O, S, and N. Where present, such heteroatoms are optionally further substituted by a heteroatom selected from O, S, N, and Si, or an alkyl, alkenyl, alkynyl, cycloalkyl, aryl, or heteroaryl group optionally substituted with halo.

The substituents $C_{1-10}$ alkyl, $C_{2-10}$ alkenyl, $C_{2-10}$ alkynyl, $C_{1-10}$ alkoxy, $C_{1-10}$ heteroalkyl, $C_{1-10}$ aminoalkyl, $C_{1-10}$ haloalkyl and/or $C_{1-10}$ alkoxycarbonyl may, if present, be substituted by one or more of hydroxyl, $C_{1-6}$ alkoxy, halogen, cyano, amino or nitro.

As used herein, the term "halogen" or "halo" includes chlorine, fluorine, which are preferred, and iodine and bromine.

The present invention relates generally to a medicinal chemistry platform for modifying drugs to facilitate loading of the drugs into liposomal nanoparticles (LN). In some preferred aspects, lipophilic/water-insoluble drugs that are resistant or incapable of being encapsulated into liposomes using standard techniques are modified to form drug derivatives that can be efficiently loaded into LN exhibiting a pH gradient across the liposomal membrane. While various aspects of the invention are described in relation to chemotherapeutic agents, methods and compositions provided herein represent a flexible technology platform that can be used with any drug or therapeutic agent for which liposomal delivery would be beneficial, including but not limited to, established chemotherapeutic agents and drugs for treating cancers, inflammatory conditions, infectious diseases, and other indications.

Also provided herein are drug derivatives capable of being efficiently loaded into LN exhibiting a transmembrane pH or ion gradient, as well as LN formulations and pharmaceutical compositions comprising such drug derivatives. In various embodiments, the drug derivatives are prepared by chemically modifying known drugs having one or more properties, such as but not limited to, poor aqueous solubility, that prevent them from being efficiently loaded into liposomes. In some preferred embodiments, the drug is a chemotherapeutic agent.

In some aspects, drug derivatives provided herein are formed by derivatizing a drug with a "solubilizing unit" which possesses one or more characteristics that facilitate loading of the derivatized drug into LN. In various aspects, the solubilizing unit is physiochemically tailored to facilitate efficient loading of a derivatized drug into LN and/or efficient release of the drug from the LN under preferred conditions at or near a therapeutic target.

In some preferred aspects, the solubilizing unit comprises a weakly basic amino group which facilitates active loading of the drug derivative into LN in the presence of a transmembrane pH or ion gradient. As used herein, the term "weak base derivative" refers to a drug modified according to methods provided herein to contain a weakly basic moiety, such as a primary, secondary or tertiary amine.

In some aspects, the weak base moiety is an ionizable amino group, such as an N-methyl-piperazino group, a morpholino group, a piperidino group, a bis-piperidino group or a dimethylamino group. Examples of modifying groups for the synthesis of weak base drug derivatives include, but are not limited to, N-methyl-piperazino (e.g., as in the anticancer drug Glivec®), bis-piperazino, bis-piperidino (e.g., as in the anticancer drug irinotecan), piperidino, morpholino, dimethylamino, aminomethyl (glycine), aminoethyl (alanine), and aminobutyryl groups, and lipids with a protonable amine group.

In some aspects, the weakly basic amino group is selected from the group consisting of:

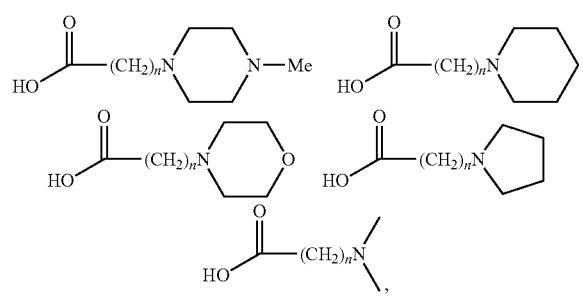

where n is between 1 and about 10, or more preferably 1 and 4.

In some aspects, the solubilization unit further comprises a linker unit which facilitates attachment of the solubilization unit to the drug targeted for derivatization. In some aspects, the linker comprises a reactive carbonyl group (e.g., a carboxylic acid moiety) which reacts with a free OH group on the drug to form a carboxylester linkage. In further aspects, the linker comprises a dialkylsilyl group which reacts with a free OH group on the drug to form a silyl ether linkage. In other aspects, the linker comprises a carbamate group.

In various aspects, drug derivatives of the following general structure are provided, where Z is a water-solubilizing unit, D is a drug, and n is 1, 2, or 3:

In some aspects, Z comprises a group of formula II, wherein:

   Formula II the wavy line represents the bond connecting Formula IIA to a reactive group, such as a free O atom, in the drug;

[L] is a Linker selected from the group consisting of: carboxy, carboxyamido, and alkyl silyl;

[S] is a Spacer selected from the group consisting of:
$C_1$-$C_{10}$ alkyl, $C_2$-$C_{10}$ alkenyl, and $C_2$-$C_{10}$ alkynyl, each optionally substituted with one or more substituents selected from the group consisting of: halo; $C_1$-$C_{10}$ alkyl; cycloalkyl; and —$YR^2$, wherein
Y is a heteroatom selected from the group consisting of: N, O, S, and Si, and
$R^2$ is selected from the group consisting of: H; a heteroatom selected from the group consisting of N, O, and S; $C_1$-$C_{10}$ alkyl; and cycloalkyl, each optionally substituted with halo;
$C_1$-$C_{10}$ heteroalkyl, optionally substituted one or more times with —$YR^2$, wherein
Y is a heteroatom selected from the group consisting of N, O, S, and Si, and
$R^2$ is selected from the group consisting of: H; a heteroatom selected from the group consisting of: N, O, and S; $C_1$-$C_{10}$ alkyl; and cycloalkyl, each optionally substituted with halo; and
cycloalkyl, heterocyclyl, aryl, and heteroaryl, each optionally substituted with halo; and

[N] is a Solubilization Domain, comprising a weakly basic group that facilitates loading of the drug derivative into LN exhibiting a transmembrane pH or ion gradient, where [N] is of the general formula III, wherein:

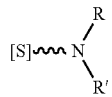   III

R and R' are independently selected from the group consisting of: H; $C_1$-$C_{10}$ alkyl, $C_2$-$C_{10}$ alkenyl, $C_2$-$C_{10}$ alkynyl, each optionally substituted with halo; cycloalkyl, heterocyclyl, aryl, and heteroaryl, each optionally substituted with halo; and a protonable nitrogen-containing heterocyclic system; or
R and R' together with the nitrogen atom to which they are attached form a heterocyclic ring having four to five carbon atoms, which may comprise one of multiple rings within a ring system.

In various aspects, the solubilizing unit is tailored to facilitate active loading of the drug derivative to specific locations within the LN. For example, in some aspects, a drug is derivatized with a water-solubilizing unit that facilitates active loading of the drug derivative into the aqueous interior of the LN. The addition of an amine group is a common drug modification strategy to improve water-solubility (e.g., Capdeville et al., Nature Reviews Drug Discovery, 1: 493-502 (2002); Pizzolato and Saltz, Lancet, 361: 2235-2242 (2003)), and a variety of methods are known in the art for making amine drug derivatives, including reversible drug conjugates (e.g., groups removed in vivo by enzyme action). Non-limiting examples of amine-modified drugs with improved aqueous solubility include the anticancer agents Glivec (N-methyl-piperazine), irinotecan (bis-piperidine) and topotecan (ethyldimethylamino group).

In other aspects, a drug is derivatized with a lipid-solubilizing unit to facilitate active loading of the drug derivative such that the derivative resides in, or is stably associated with, the liposomal membrane. In some aspects, the lipid-solubilizing unit comprises a weakly basic group and a lipophilic group. The lipophilic group may be selected to facilitate active loading of the drug into LN, stability of the drug within LN, and/or the release of the drug at or near a therapeutic target. In some aspects, the lipophilic group has a similar or complementary lipid composition as the liposomal membrane. In some such aspects, the lipid-solubilizing unit is selected from a group of formula IVa or IVb:

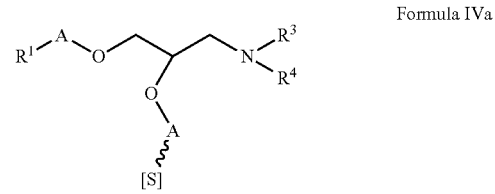   Formula IVa

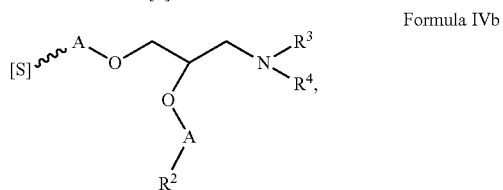   Formula IVb wherein:
A is selected from the group consisting of: carbonyl, methylene, and NR—C=O, where R is H or $C_1$-$C_5$ alkyl;
$R^1$ and $R^2$ are independently selected from the group consisting of: linear or branched $C_1$-$C_{30}$ alkyl, $C_2$-$C_{30}$ alkenyl, and $C_2$-$C_{30}$ alkynyl; and
$R^3$ and $R^4$ are independently selected from the group consisting of: H; $C_1$-$C_{10}$ alkyl, $C_2$-$C_{10}$ alkenyl, $C_2$-$C_{10}$ alkynyl, each optionally substituted with halo; and cycloalkyl, heterocyclyl, aryl, and heteroaryl, each optionally substituted with halo; or
$R^3$ and $R^4$ together with the nitrogen atom to which they are attached form a heterocyclic ring having four to five carbon atoms, which may comprise one of multiple rings within a ring system.

Weak base derivatives can be loaded into LN by imposing a pH gradient across the liposome membrane (inside acidic) and incubating the liposome with the drug to be encapsulated. Depending on the pH, weak base derivatives can exist in either a charged (protonated) form (e.g., where the pH is below the pKa) or a neutral form (e.g., where the pH is at or above the pKa). Only the neutral form can rapidly permeate across the liposome membrane. Upon reaching the acidic liposome interior, the charged membrane-impermeable form is adopted, driving the continued uptake and retention of the compound in the liposome interior.

In some preferred aspects, the drug loading properties of a weak base derivative provided herein can be fine-tuned by selecting and/or modifying one or more properties of derivative amine groups and/or derivative lipophilic groups. For example, the pKa of a derivative amine group can be selected such that the amine group is protonated in the aqueous interior of the LN preparation being used (e.g., at low pH) and unprotonated in the external medium (e.g., at neutral or basic pH).

In some aspects, the pKa of a derivative amine group is less than or equal to about 12.0, less than or equal to about 11.5, less than or equal to about 11.0, less than or equal to about 10.5, less than or equal to about 10.0, less than or equal to about 9.5, or less than or equal to about 9.0.

In some aspects, the pKa of a derivative amine group is at least about 5.0, at least about 5.5, at least about 6.0, at least about 6.5, at least about 7.0, at least about 7.5, at least about 8.0, or at least about 8.5.

A solubilizing unit comprising a weak base moiety can be attached to any suitably reactive functional group on the drug targeted for modification. Such functional groups include hydroxyl, sulfhydryl and carboxyl groups among others. In some aspects, the solubilizing unit is attached via a free OH group on the drug, for example, by a carboxylester bond.

In some aspects, drugs are derivatized in a region that is not essential for the intended therapeutic activity such that the activity of the derivative is substantially equivalent to that of the free drug. For example, in some aspects, the weak base derivative comprises the taxane docetaxel derivatized at the 7-OH group of the baccatin skeleton.

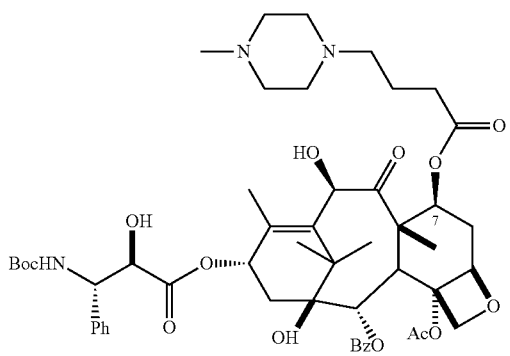

In further aspects, drugs are derivatized in a region that is essential for activity such that the derivatives are prodrugs that must be converted to the parent compound or another active form in order to exert the intended therapeutic effect. For example, in some aspects, docetaxel derivatives are provided herein which are derivatized at the 2'-OH group which is essential for docetaxel activity.

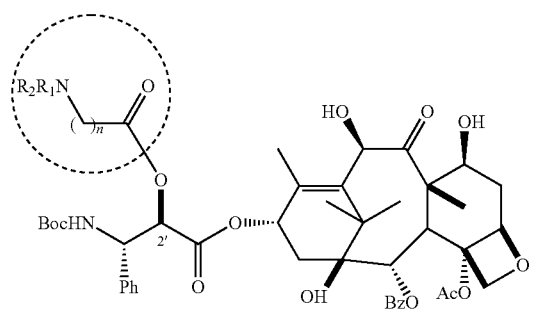

Prodrug derivatives provided herein are preferably rapidly converted to the free drug upon release from the LN carrier and exposure to physiological conditions in vivo. For example, in some preferred aspects, the derivative amino group of a weak base derivative provided herein is removed rapidly from the drug following release from the liposome, for example via the action of endogenous enzymes and/or by spontaneous hydrolysis.

Thus, in some aspects, the solubilizing unit is reversibly conjugated to the drug derivative to form a prodrug which is stable under certain conditions (e.g., during loading, formulation, storage, and/or administration of a LN composition) and dissociates to release the free drug at or near its therapeutic target(s), for example by the action of endogenous enzymes and/or under certain physiological conditions (e.g., pH, ionic strength).

In some aspects, weak base derivatives are engineered to be stable inside the liposomal nanocarrier (e.g., at low pH) but are 'self-releasing' at physiological pH, such that the prodrug is rapidly converted into its active form upon release from the liposome. This can be achieved by, e.g., attaching an aminobutyryl group to docetaxel, which in its unprotonated form (pH 7.4) can trigger release through nucleophilic attack on the ester carbonyl.

In some aspects, the hydrolytic stability of an ester linkage of a weak base derivative may be modulated by exploiting one or more of the following effects:

i) inductive effects: Esters may be stabilized or destabilized toward cleavage at physiological pH, either with assistance of proteases or by spontaneous hydrolysis, or by positioning the solubilizing amino group closer to (destabilization) or farther away from (stabilization) the carbonyl center. The pKa of the amino group also plays a role in this context: a charged (protonated) amine promotes ester hydrolysis under physiological conditions. By appropriate choice of groups R groups on the amino group the N-center can be modulated to achieve an ideal rate of ester cleavage.

ii) Chemical and proximity effects. Esterification with, e.g., a 4-aminobutyrl group in which the amino unit has a pKa ~6 produces an entity which will exist in its protonated form at low pH, such as the pH found inside ammonium sulfate-loaded LN. Release of such derivatives from the LN carrier and exposure to physiological conditions (e.g., pH 7.4) promotes formation of a free base form, allowing the free amine to trigger "self-release" of the derivatizing unit through nucleophilic attack on the ester carbonyl. Advantageously, this allows prodrug derivatives to be rapidly converted into active form upon release from LN.

In further aspects, the hydrolytic stability of a silyl ether linkage of a weak base derivative may be modulated to facilitate spontaneous hydrolysis. Unlike with ester linkers, there are no endogenous desilylating enzymes. Thus, derivatives comprising a silyl ether linkage preferably comprise a linker group that allows for hydrolysis under physiological conditions. The primary determinant of the rate of silyl group cleavage is the steric bulk around the Si atom. Modulation of this physiochemical property entails varying the size of groups R and R' in silyl halides, e.g., through the series Me, Et, i-Pr, t-Bu, Ph, etc. As in the case of the esters, the pKa of the amino group also plays a role in defining the stability of derivatives. For example, an amino group with a pKa ~6 will exist predominantly as the free base at physiological pH, thereby facilitating the cleavage of the silyl group.

In further aspects, the size and/or chemical composition of a lipophilic derivative group can be selected to enhance solubility in the liposomal membrane and/or stability of the drug within the liposome (e.g., by anchoring the drug in the liposomal membrane).

Advantageously, weak base derivatives of a drug provided herein can be loaded into liposomes more efficiently than the free drug. In some aspects, a weak base derivative provided herein can be loaded into liposomes with a loading efficiency or at least about 50%, at least about 55%, at least about 65%, at least about 70%, at least about 75%, at least about 80%, at least about 85%, or higher over a wide range of drug-to-lipid ratios (e.g., from about 0.01 mg/mg, to about 10 mg/mg or higher).

In further aspects, LN formulations of weak base derivatives provided herein can be optimized to achieve sustained release of the drug derivative through, e.g., modification of the lipid composition of the LN carrier membrane. For example, in various aspects, LN formulations provided herein have a release half-life in vivo of between about 1 to about 96 hours, or about 2 to about 72 hours, or about 4 to about 48 hours.

Methods provided herein can be used to modify any drug or therapeutic agent for which a liposomal formulation is desirable. In some preferred aspects, the drug is lipophilic and/or poorly water-soluble. Advantageously, modification of such drugs according to methods provided herein results in improved solubility, reduced toxicity, increased efficacy, and/or other benefits relative to the free drug.

Non-limiting examples of drugs that can be modified and loaded into LN according to methods provided herein are given in Table 1.

TABLE 1

Exemplary drugs for derivatization.

| Drug | Indication | Solubility in Water (µg/ml) |
|---|---|---|
| Amprenavir | HIV | 36 (49 pred.) |
| Bexarotene | Antineoplastic | 0.15 (pred.) |
| Calcitrol | Calcium regulator | 6.7 (pred.) |
| Cyclosporin A | Immunosuppressant | 9.5 (pred.) |
| Digoxin | Heart failure | 127 (pred.) |
| Doxercalciferol | Hyperparathyroism | relatively insoluble |
| Paricalcitol | Hyperparathyroism | 6.8 |
| Dronabinol | Anorexia | 2800 (pred.) insoluble in water, oil at room temp. |
| Etoposide | Antineoplastic | 58.7, 200 |
| Teniposide | Antineoplastic | 59.8 (pred.) |
| Isotretinoin | Antiacne | 4.8 (pred.) |
| Sirolimus | Antineoplastic | 1.7 (pred.), insoluble in water |
| Tretinoin | Antineoplastic | 1000, 4.7 (pred.) |
| Valproic acid | Antiepileptic | 1300 |
| Amphotericin B | Antifungal | 750 |
| Docetaxel | Antineoplastic | 12.7 (pred.) |
| Paclitaxel | Antineoplastic | 5.5 (pred.) |
| Fulvestrant | Antineoplastic | 6.7 (pred.) |
| Tacrolimus | Immunosuppressant | 4 (pred.), insoluble |
| Valrubicin | Antineoplastic | 32.5 (pred.), insoluble |

TABLE 1-continued

Exemplary drugs for derivatization.

| Drug | Indication | Solubility in Water (µg/ml) |
|---|---|---|
| Propofol | Anesthetic | 124 |
| Prednisone | Anti-inflammatory | 312 |
| Prednisolone | Anti-inflammatory | 223 |
| Dexamethasone | Anti-inflammatory | 89 |
| Tacrolimus (FK-506) | Immunosuppressive | 4 (pred.), insoluble |
| Mycophenolic acid | Immunosuppressive, anti-proliferative | 35.5 (pred.), insoluble |
| Lovastation | Anti-cholesteremic | 24 (pred.) | pred. = predicted
Sources: R. G. Strickley, Pharm. Res. 21(2): 201 (2004); DrugBank at http://www.drugbank.ca/

In some preferred aspects, the drug is a chemotherapeutic agent. Examples of established drugs or classes of drugs that can be derivatized according to methods provided herein include the taxanes (e.g. paclitaxel and docetaxel) and the podophyllotoxin derivatives (e.g. etoposide and teniposide). The taxanes, which include docetaxel (Taxotere) and paclitaxel (Taxol), are an important family of drugs that have extensive use in clinical oncology. Like most anticancer drugs, taxanes are non-selective for cancer cells and can also cause damage to healthy cells. Because taxanes are poorly soluble in aqueous solution, they are typically formulated in vehicles such as Cremophor and Polysorbate 80, which themselves cause adverse reactions in patients. Steroidal and anti-allergy pre-medication is often used to minimize the side effects of the vehicle. Advantageously, LN taxane formulations provided herein allow for administration of taxanes without use of a toxic vehicle. Moreover, because LN can exit the bloodstream and preferentially accumulate at high concentrations in tumors due to the "leaky" nature of blood vessels at these sites, LN taxane formulations can offer superior anti-cancer activity with fewer side effects (e.g., improved therapeutic index) compared to Taxotere, the approved formulation of the parent compound.

In some aspects, LN formulations provided herein increase the amount of a chemotherapeutic agent that specifically reaches a site of tumor growth and/or prolongs the duration of exposure of a tumor to therapeutically active levels of drug, for example through extended plasma half-life of the LN and/or sustained release of the chemotherapeutic agent from the LN carrier.

In some aspects, the drug is docetaxel (Taxotere®) or paclitaxel, the structures of which are shown below. The two drugs differ at the level of the acyl group present on the nitrogen atom of the side chain (tert-butoxycarbonyl, or BOC, in docetaxel; benzoyl in paclitaxel) and in that the C-10 OH group is free in docetaxel, but it is acetylated in paclitaxel.

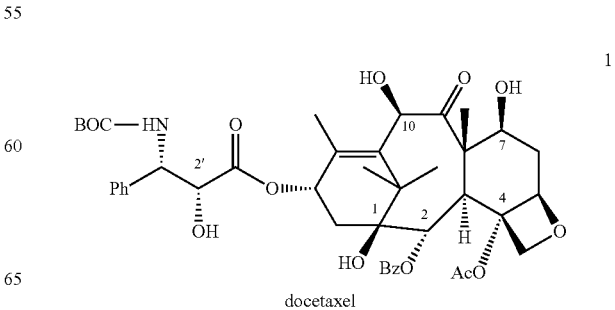

docetaxel

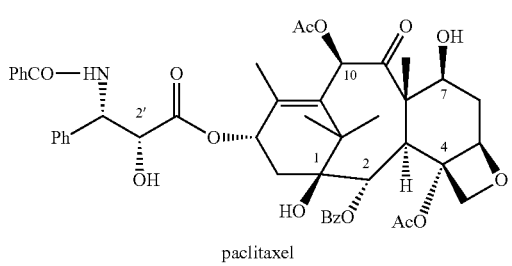

paclitaxel

Modification of docetaxel and paclitaxel according to methods provided herein involves derivatization of one or more of the free OH units with appropriate groups. In some aspects, the drug is derivatized at the C-1 OH. In other, preferred aspects, the drug is derivatized at the C-2', C-7, and/or C-10 OH to produce the following derivatives, wherein groups Z connected to the C-2', C7, and/or C-10 OH are, independently, H, or a residue containing a protonatable nitrogen functionality. Any drug may be derivatized in a similar manner as docetaxel and paclitaxel at a free OH group or other reactive functionality (which can be present on the native drug or on a modified version of the drug).

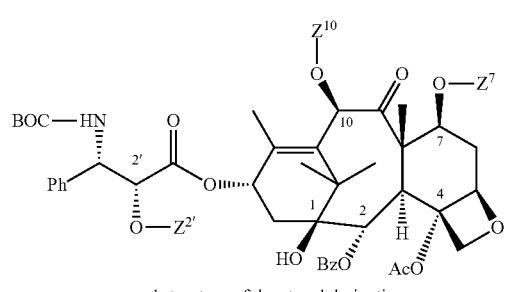

general structure of docetaxel derivatives

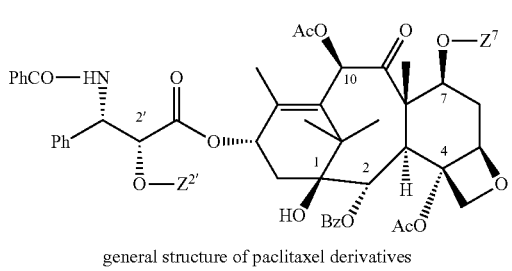

general structure of paclitaxel derivatives

In some aspects, LN formulations provided herein have one or more pharmacological properties of liposomal vincristine (Margibo®), which is currently in Phase III clinical trials for the treatment of various cancers (e.g., Boman et al., Brit. J. Cancer 72: 896-904 (1995), Shan et al., Cancer Chemother. Pharmacol. 58(2): 245-55 (2006), Waterhouse et al., Methods Enzymol. 391: 40-57 (2005)).

In various aspects, drug derivatives of the following general structure are provided, where Z is a water-solubilizing unit and D is a drug:

In some aspects, Z comprises a group of formula IIA, wherein:

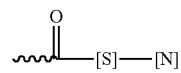

Formula IIA (i) the wavy line represents the bond connecting Formula IIA to a reactive group, such as a free O atom, in the drug (e.g., compounds 3 and/or 4, above);

(ii) [S] is a "spacer" comprising:

(a) a chain of the type $(CH_2)_n$, where n may range from 1 to 10, OR (b) a derivative of the above $(CH_2)_n$ where one or more H atoms are replaced by: a linear, branched, or cyclic alkyl group containing from 1 to 10 C atoms, a heteroatom such as N, O, S, Si, which may be further connected to H atoms; or to heteroatoms such as N, O, S; or to linear, branched, or cyclic alkyl groups containing from 1 to 10 C atoms and facultatively incorporating one or more halogen atoms, a halogen atom; OR (c) a derivative of the above $(CH_2)_n$ where one or more $CH_2$'s are replaced by: a heteroatom such as N, O, S, Si, which may be further connected to H atoms; or to heteroatoms such as N, O, S; or to linear, branched, or cyclic alkyl groups containing from 1 to 10 C atoms and facultatively incorporating one or more halogen atoms, a ring structure consisting of 3 to 10 carbon atoms and facultatively incorporating one of more heteroatoms such as N, O, S, Si, or halogen, as well as multiple bonds among pairs of atoms; OR (d) a derivative of the above $(CH_2)_n$ where one or more pairs of adjacent C atoms share a double bond of E- or Z-geometry, or a triple bond.

Examples of such spacers [S] include, but are not limited to:

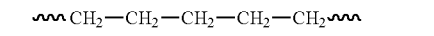
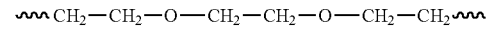
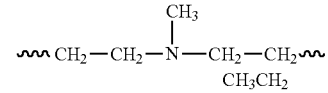
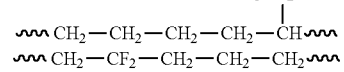
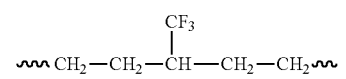
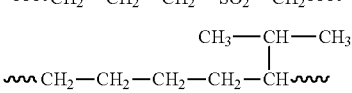
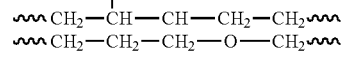
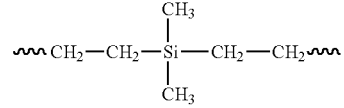

-continued

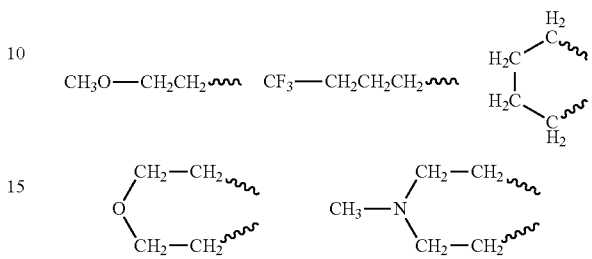

(iii) [N] is a Solubilizing Domain, comprising a weakly basic group that facilitates loading of the drug derivative into LN exhibiting a transmembrane pH or ion gradient, selected from:

(a) a substituent of general structure R—N—R', in which the N (nitrogen) atom is connected to the spacer, and where R and R' may be, independently: H; a linear, branched, or cyclic alkyl group containing from 1 to 10 C atoms and facultatively incorporating with one or more heteroatoms such as N, O, S, Si, and halogen, as well as multiple bonds among pairs of atoms; or part of ring structure consisting of 3 to 10 carbon atoms and facultatively incorporating one of more heteroatoms such as N, O, S, Si, or halogen, as well as multiple bonds among pairs of atoms.

Examples of such R and R' include, but are not limited to, the following:

H, methyl, ethyl, propyl, isopropyl, butyl, isobutyl, sec-butyl, tert-butyl, cyclopropyl, cyclobutyl, cyclopentyl, cyclohexyl, phenyl, benzyl,

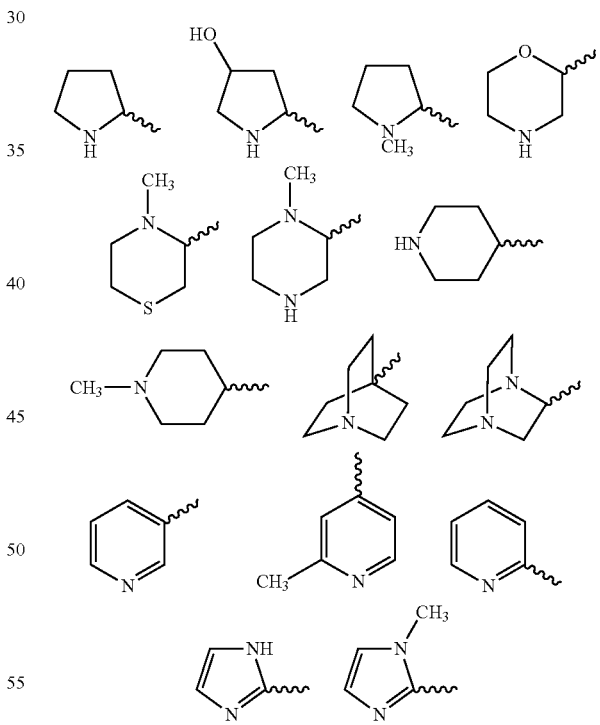

OR (b) a protonatable, nitrogen-containing heterocyclic system such as a pyrrolidine, piperidine, pyridazine, morpholine, thiomorpholine, quinuclidine, imidazole, pyridine, and the like, or a substituted variant thereof, as illustrated by the following representative, but not exclusive, examples, wherein the wavy line represents the bond connecting the heterocyclic structure to the spacer:

Representative aspects of formula IIA above thus include, but are not limited to, the following:

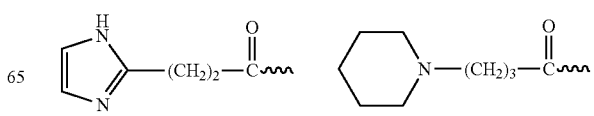

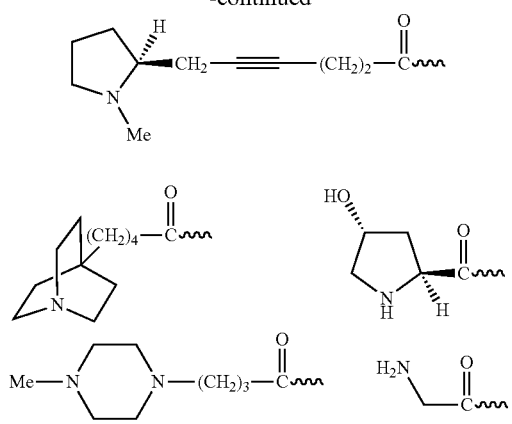
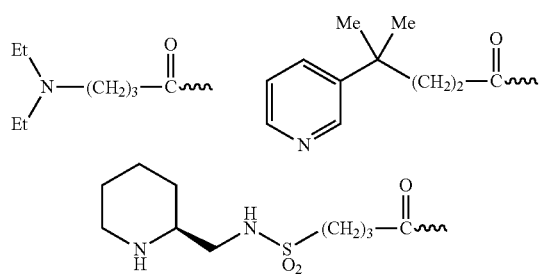
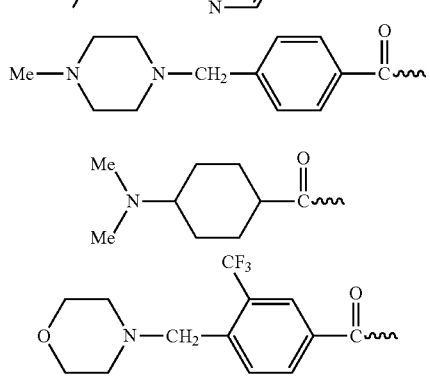
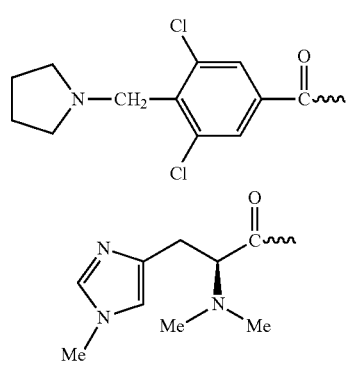
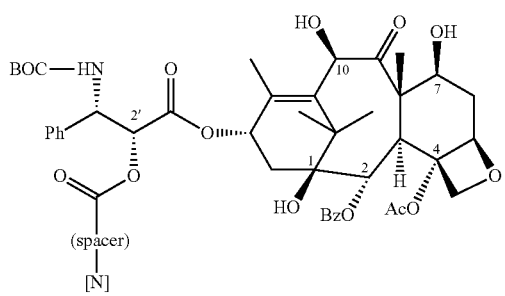
type A
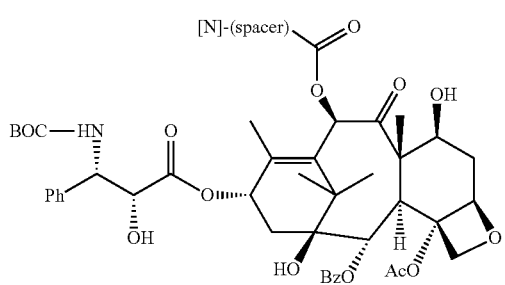
type B
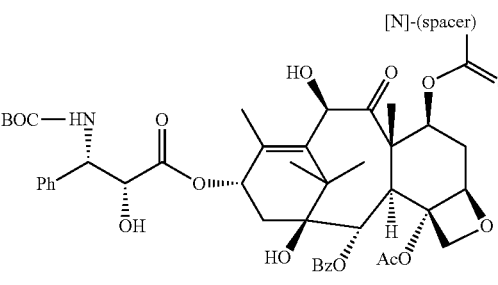
monoester derivatives of docetaxel
type C
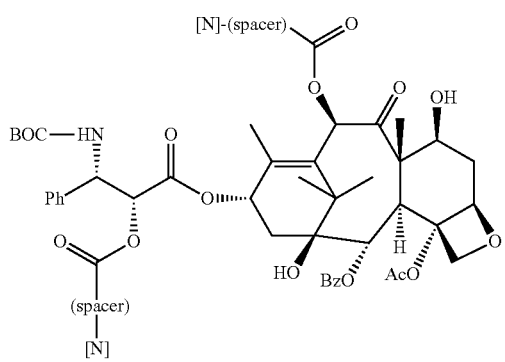
type D
Derivatization of docetaxel with up to three units of Formula IIA, which may be different or identical, produces mono-, bis-, or triesters of the type A, B, C, D, E, F, and G shown below.

type E

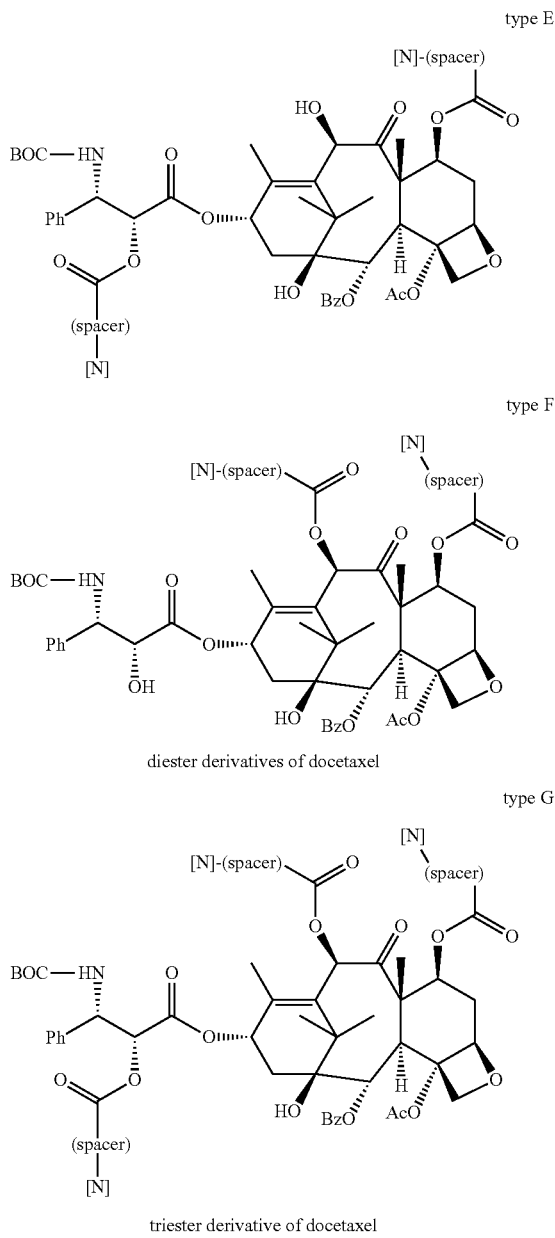

diester derivatives of docetaxel type F type G triester derivative of docetaxel

In a like manner, paclitaxel may be converted to mono- and diester derivatives of the type H, I and J shown below:

type H

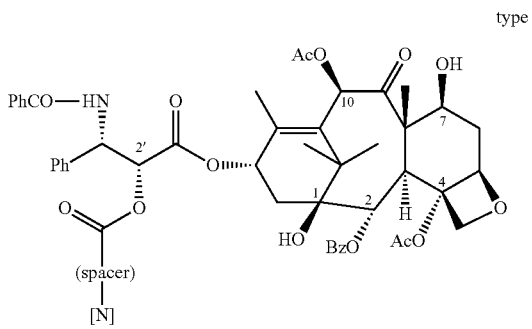

type I

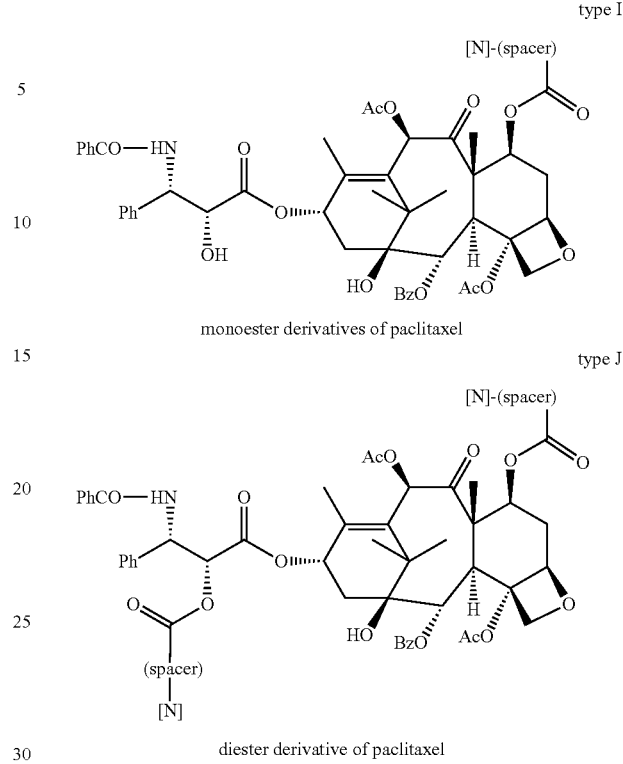

monoester derivatives of paclitaxel type J diester derivative of paclitaxel

Elaboration of docetaxel or of paclitaxel to such derivatives involves, for instance, the coupling of the unprotected or partially protected parent drug with a carboxylic acid form of 5 by the use of standard techniques of modern organic chemistry that are well known to the person skilled in the art.

In some aspects, Z comprises a group of Formula IIB, wherein:

Formula IIB

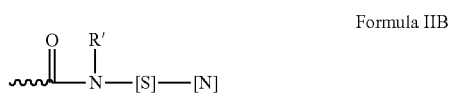

(i) the wavy line represents the bond connecting Formula IIB to the appropriate reactive group, such as an O atom, in the drug [D] (e.g., compounds 3 and/or 4);

(ii) the "spacer" [S] is as detailed above for Formula IIA (iii) the solubilizing unit [N] is as detailed above for Formula IIA (iv) R' is H, or a linear, branched, or cyclic alkyl group containing from 1 to 10 C atoms and facultatively incorporating with one or more heteroatoms such as N, O, S, Si, and halogen, as well as multiple bonds among pairs of atoms.

Examples of such R' include, but are not limited to, the following:

H, methyl, ethyl, propyl, isopropyl, butyl, isobutyl, sec-butyl, tent-butyl, cyclopropyl, cyclobutyl, cyclopentyl, cyclohexyl, phenyl, benzyl,

Representative aspects of structure Formula IIB above include, but are not limited to, the following:

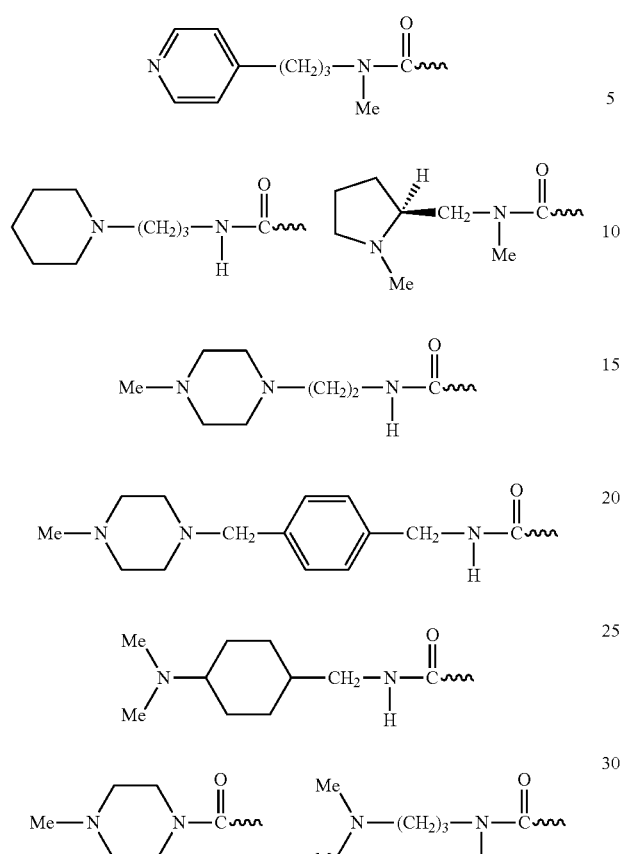
Derivatization of docetaxel with up to three units of the type 6, which may be different or identical, produces mono-, bis-, or tricarbamates of the type A, B, C, D, E, F, and G shown below.
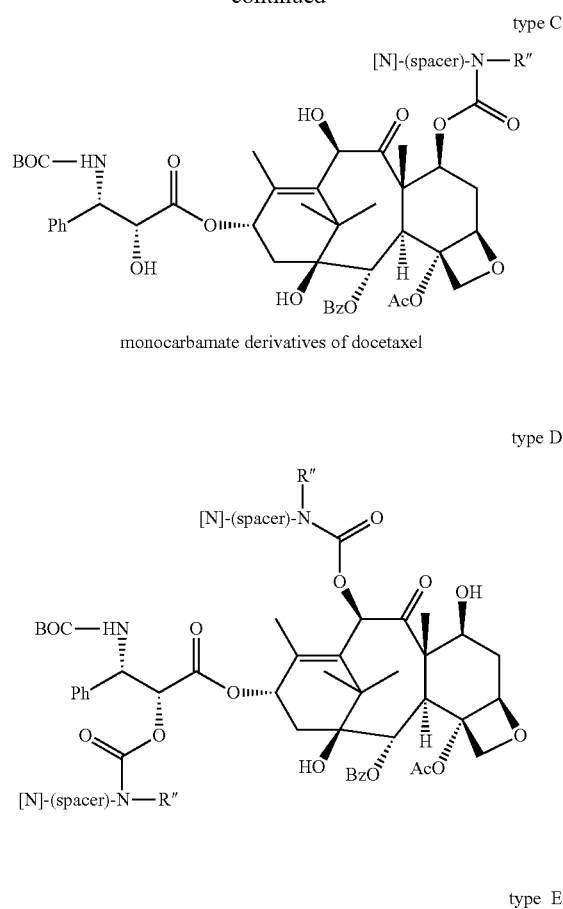
monocarbamate derivatives of docetaxel
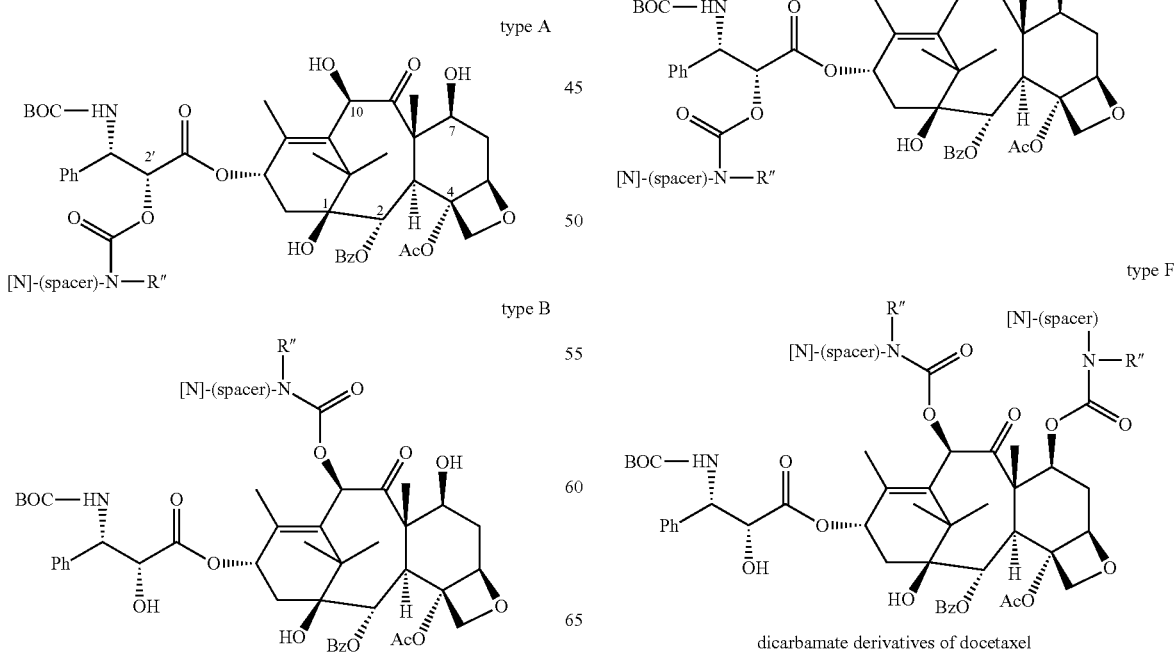
dicarbamate derivatives of docetaxel

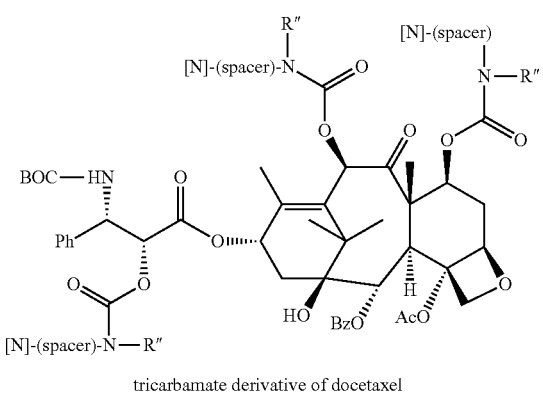

tricarbamate derivative of docetaxel

In a like manner, paclitaxel may be converted to mono- and dicarbamate derivatives of the type H, I and J shown below:

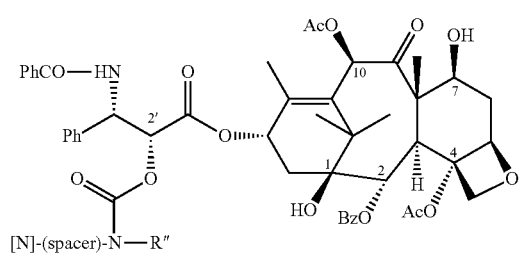

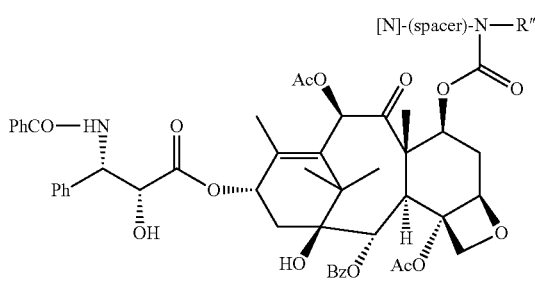

monocarbamate derivatives of paclitaxel

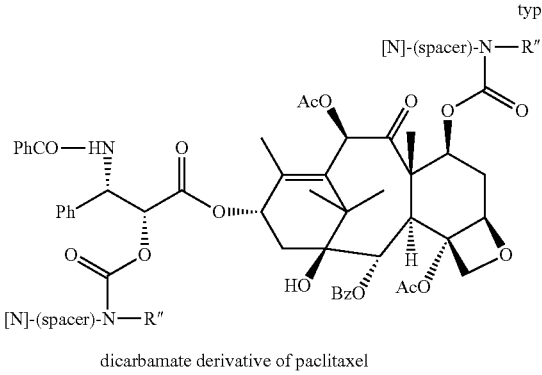

dicarbamate derivative of paclitaxel

Elaboration of docetaxel or of paclitaxel to such derivatives involves, for instance, the coupling of the unprotected or partially protected parent drug with an isocyanate (R″=H) or an imidazolide (R″≠H) form of 6 by the use of standard techniques of modern organic chemistry that are well known to the person skilled in the art.

In some aspects, Z is a group of the general Formula IIC, wherein:

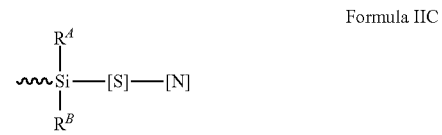

Formula IIC (i) the wavy line represents the bond connecting Formula IIC to an appropriate reactive group, such as an O atom, in the drug [D] (e.g., compounds 3 and/or 4);

(ii) the "spacer" is as detailed above for Formula IIA (iii) Group [N] is as detailed above for Formula IIA (iii) $R^A$ and $R^B$ represent, independently, a linear, branched, or cyclic alkyl group containing from 1 to 10 C atoms and facultatively incorporating with one or more heteroatoms such as N, O, S, Si, and halogen, as well as multiple bonds among pairs of atoms.

Examples of such $R^A$ and $R^B$ include, but are not limited to, the following: H, methyl, ethyl, propyl, isopropyl, butyl, isobutyl, sec-butyl, tent-butyl, cyclopropyl, cyclobutyl, cyclopentyl, cyclohexyl, phenyl, and benzyl.

Representative aspects of Formula IIC above include, but are not limited to, the following:

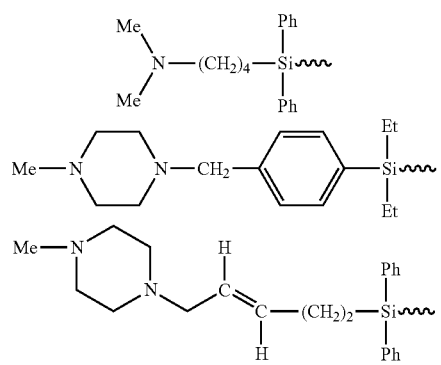

Derivatization of docetaxel with up to three units of Formula IIC, which may be different or identical, converts it to mono-, bis-, or tris-silyl ethers of the type A, B, C, D, E, F, and G shown below.

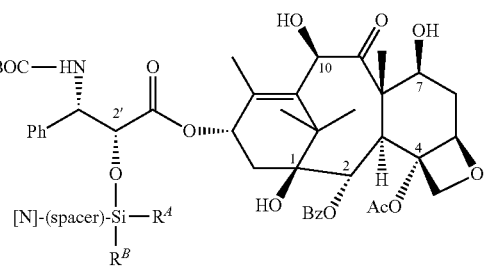

type B
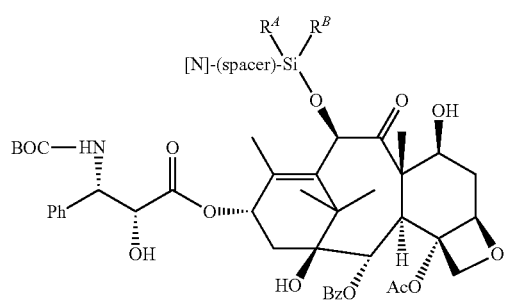
type C
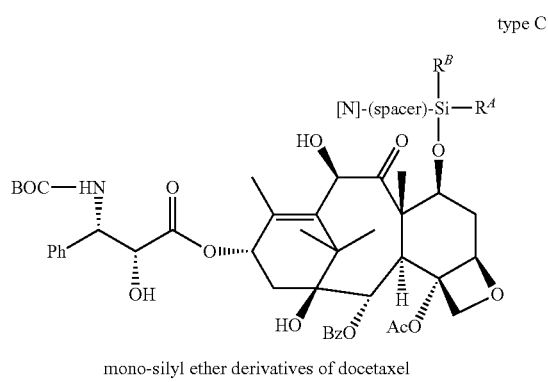
mono-silyl ether derivatives of docetaxel
type D
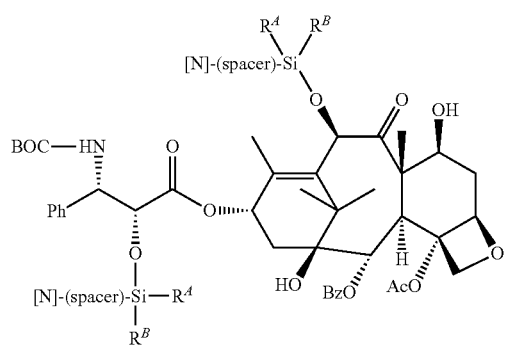
type E
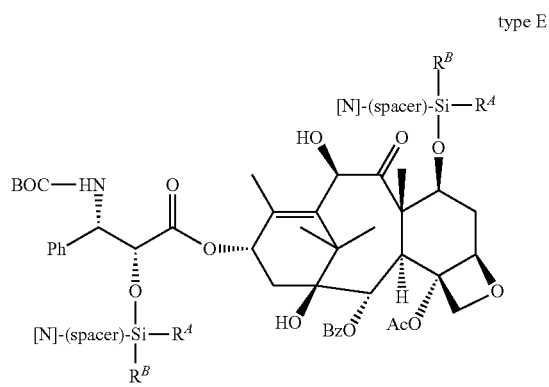
type F
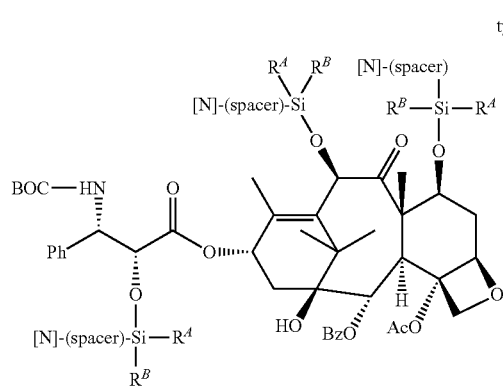
bis-silyl ether derivatives of docetaxel
type G
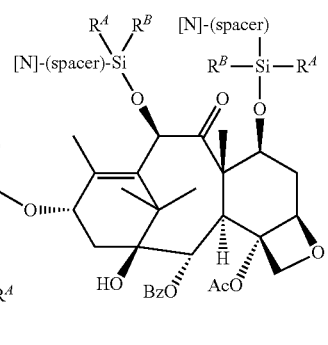
tris-silyl ether derivatives of docetaxel
In a like manner, paclitaxel may be converted to mono- and diester derivatives of the type H, I and J shown below:
type H
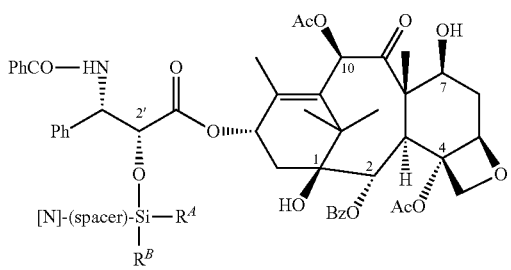
type I
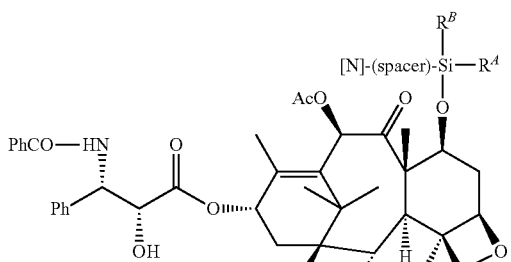
mono-silyl ether derivatives of paclitaxel

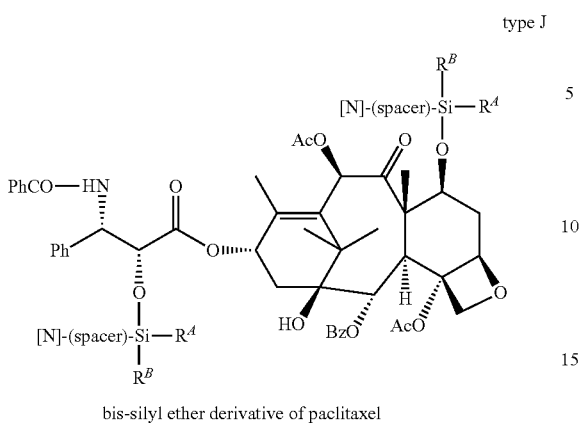

bis-silyl ether derivative of paclitaxel

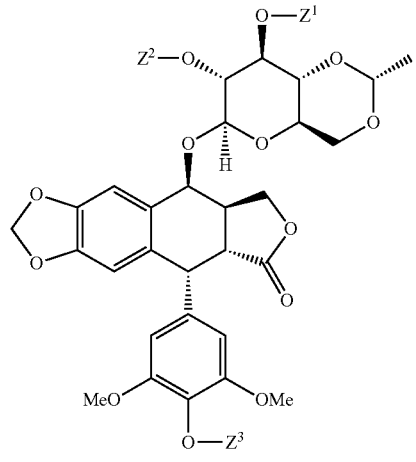

mono, bis, or tris ester, carbamate, or silyl ether derivatives

Elaboration of docetaxel or paclitaxel to such derivatives involves, for instance, the coupling of the unprotected or partially protected parent drug with a chloride or an imidazolide form of Formula IIC by the use of standard techniques of modern organic chemistry that are well known to the person skilled in the art.

The technology exemplified above with taxanes is applicable to any drug possessing suitable anchoring sites, such as OH, COOH (carboxyl), or NH groups, for solubilizing units, [Z], of Formulae IIA, IIB, or Formulae IIC.

In some aspects, the drug is etoposide, which is a widely used anticancer agent approved for the treatment of lymphoma, lung and testicular cancers. Etoposide exhibits poor water-solubility, undergoes metabolic inactivation, and has substantial toxic side effects. In various preferred aspects, etoposide LN formulations provided herein have substantially reduced toxicity, improved solubility and bioavailability, and increased efficacy.

To illustrate, etoposide, 8, and the corticosteroid prednisone, 9, may be converted to ester, carbamate, or silyl ether derivatives as detailed above for the taxanes. [Z] in these derivatives is as defined earlier for compounds in the taxol series

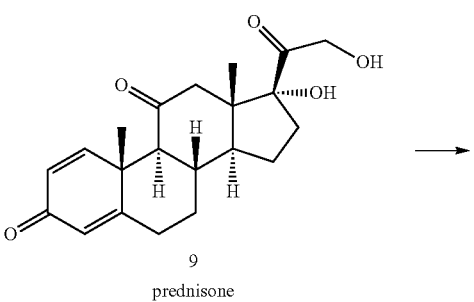

prednisone

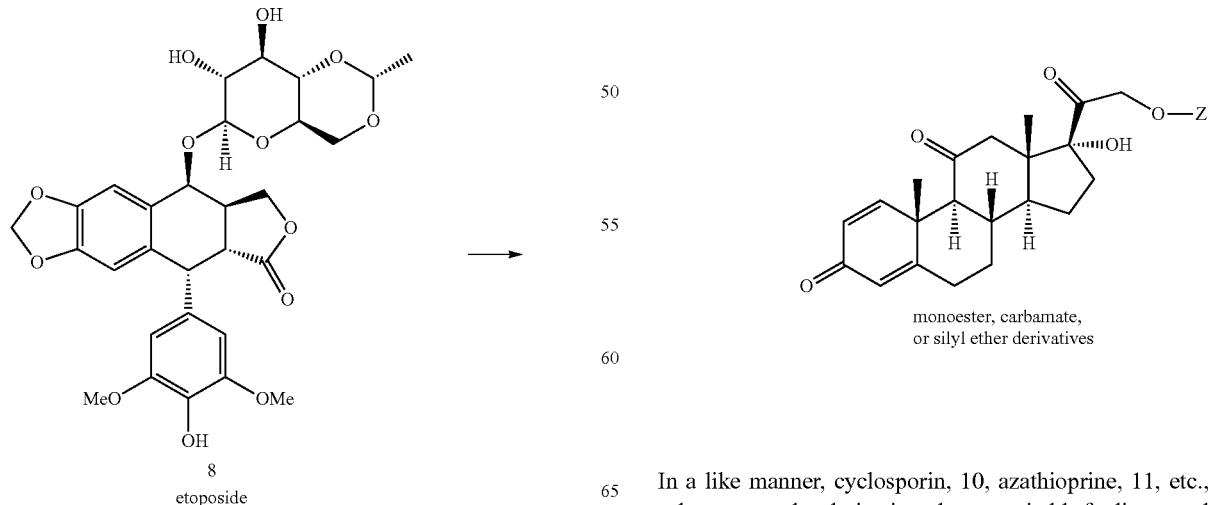

8
etoposide monoester, carbamate, or silyl ether derivatives

In a like manner, cyclosporin, 10, azathioprine, 11, etc., may be converted to derivatives that are suitable for liposomal formulation:

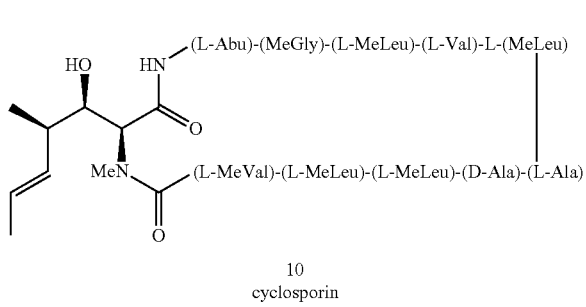
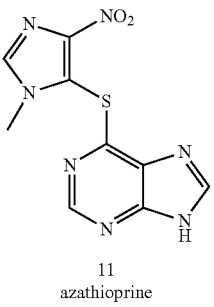

10
cyclosporin 11
azathioprine

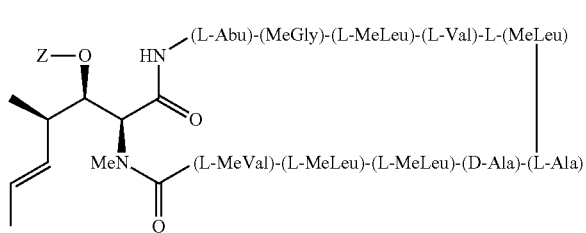
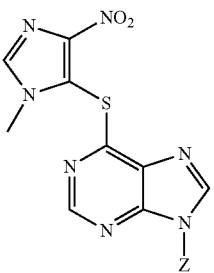

30

In some aspects, a drug of interest is derivatized with a lipid-solubilizing unit that comprises a weakly basic amine group and a lipophilic group. In some preferred aspects, the solubilizing unit has a structure that similar to that of the lipids comprising the liposomal membrane. For example, in some aspects a drug derivative is of the general formula: [D]-[L]-[S]—[N], wherein [S] is a Spacer as defined above in relation to Formulae IIA-IIC and [N] is a solubilizing domain and [L] is a linker, as defined below.

In some aspects, [N] is a group of Formula IVA ("internal" derivatives) or Formula IVB ("terminal" derivatives), wherein:

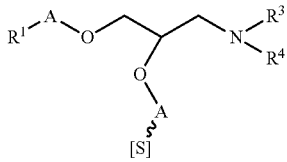

Formula IVA

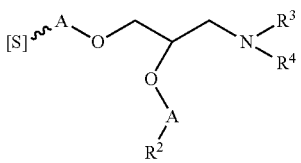

Formula IVB (i) A represents a carbonyl group (C=O); a carbamoyl group (NR—C=O, where R is H or an alkyl group incorporating from 1 to 5 C atoms); or a methylene group ($CH_2$);

(ii) $R^1$ and $R^2$ represent a linear or branched lipophilic alkyl group containing up to 30 carbon atoms and facultatively incorporating one or more multiple bonds between pairs of adjacent carbon atoms;

(iii) $R^3$ and $R^4$ represent, independently, H; or alkyl groups incorporating from 1 to 5 C atoms, such as methyl ethyl, propyl, isopropyl, butyl, isobutyl, etc.; or branches of a ring structure such as pyrrolidine, piperidine, piperazine, morpholine, thiomorpholine, etc.

(iii) the Linker, [L], is:

(a) a carbonyl group, C=O;

(b) a carbamoyl group, NR—C=O, where R is H or an alkyl group incorporating from 1 to 5 C atoms; OR (c) a group $R^A$—Si—$R^B$ as defined above.

Below are a number of clinically significant taxanes derivatized with a solubilizing group comprising a weakly basic moiety and a lipophilic moiety, to form "terminal" type (Formula IVB) derivatives and "internal" type (Formula IVA) derivatives. Such derivatives can be made by, for instance, coupling any unprotected or partially protected parent drug with a carboxylic acid, an acyl imidazolide, a carbamoyl imidazolide, a silyl chloride, or a silyl imidazolide form of the linker, [L], using techniques known in the art. The resulting derivatives can be actively loaded into LN such that the drug resides in the liposomal membrane.

Docetaxel derivatives of Formula IVA include esters, carbamates, and silyl ethers with the following representative structures:

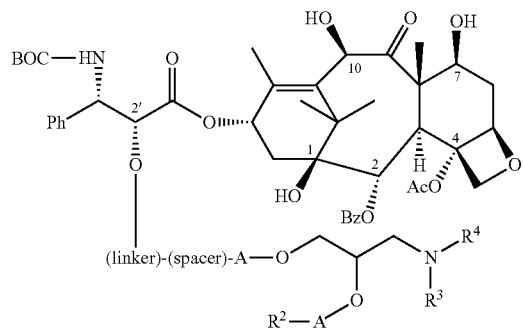
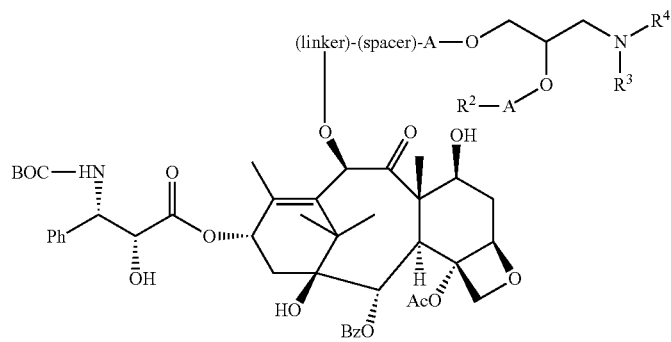
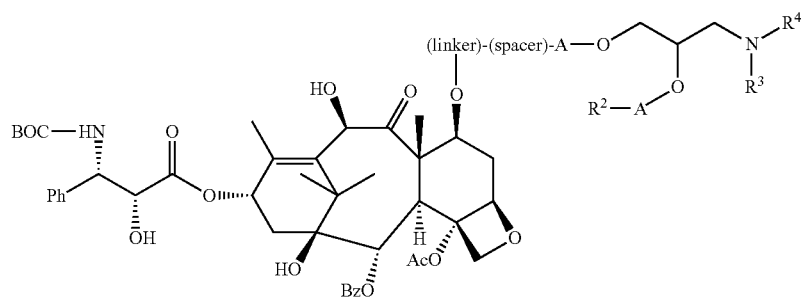
docetaxel monoesters, monocarbamates, and monosilyl ethers of Formula IVA
Paclitaxel derivatives of Formula IVA include esters, carbamates, and silyl ethers with the following representative structures:
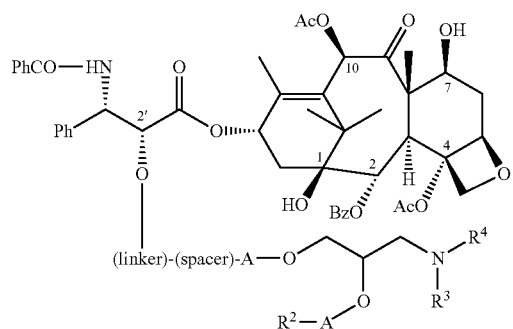

-continued

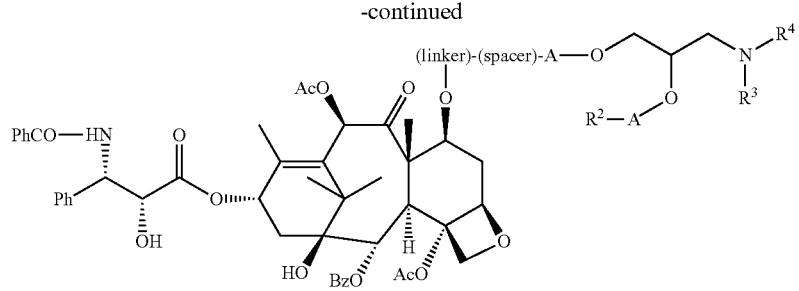

paclitaxel monoesters, monocarbamates, and monosilyl ethers of Formula IVA

Docetaxel derivatives of Formula IVB include esters, carbamates, and silyl ethers of the general type described earlier, but possessing the following representative structures:

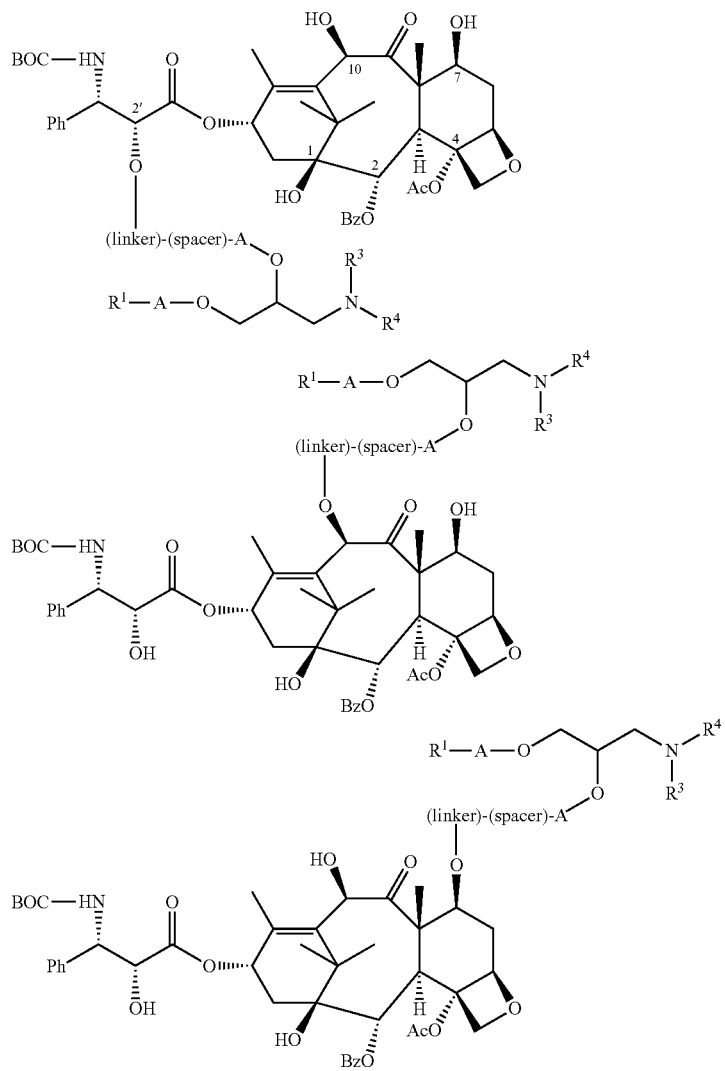

docetaxel monoesters, monocarbamates, and monosilyl ethers of Formula IVB

Paclitaxel derivatives of Formula IVB include esters, carbamates, and silyl ethers of the general type described earlier, but possessing the following representative structures:

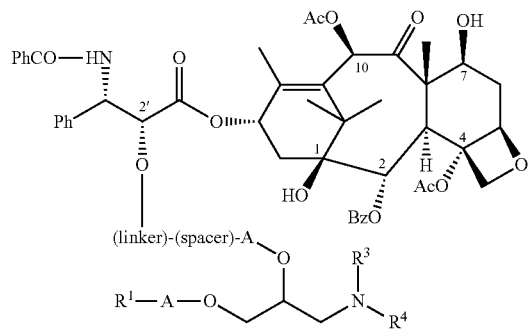

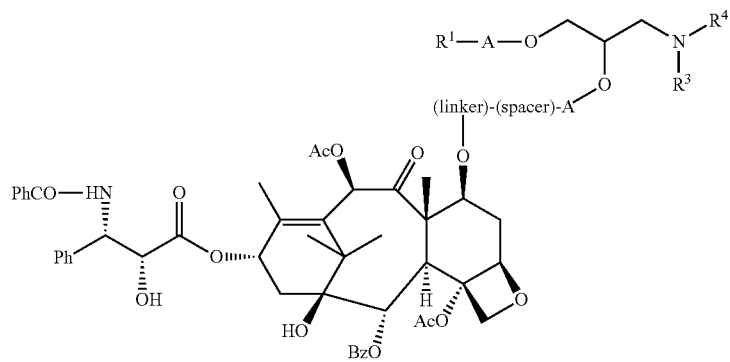

paclitaxel monoesters, monocarbamates, and monosilyl ethers of Formula IVB

Similarly, etoposide, 8, prednisone, 9, cyclosporin, 10, azathioprine, 11, and other drugs may be derivatized with a solubilizing unit that comprises a weakly basic group and a lipophilic group, such that the drug can be actively loaded within the LN membrane. With regard to compounds 8-11, 13 and 14 refer to derivatives of the formula [D]-[L]-[S]-[N] and 15 and 16 are derivatives of the formula [L]-[S]-[N], wherein [N] is according to Formula IVB in type 13 and Formula IVA in type 14 and [L] and [S] are as described above.

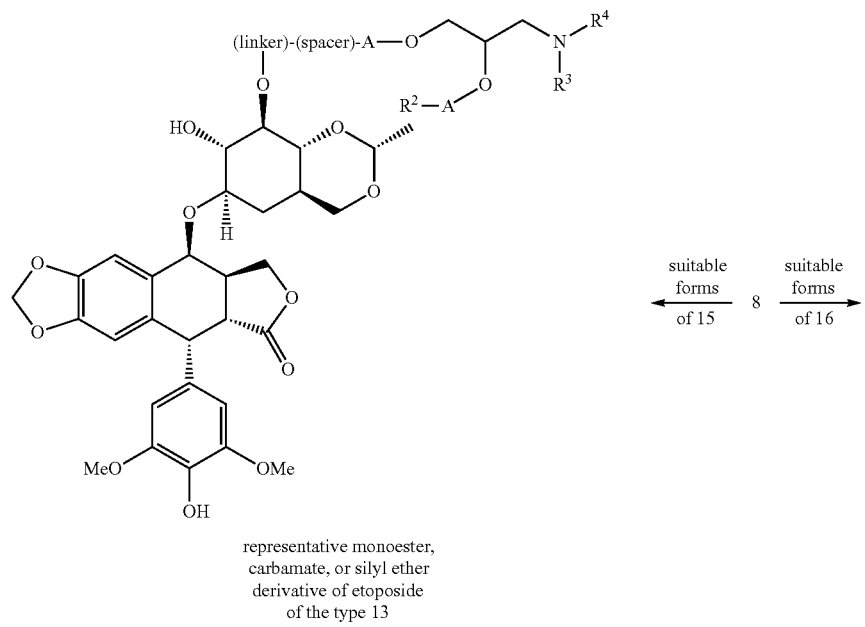

representative monoester, carbamate, or silyl ether derivative of etoposide of the type 13 suitable forms of 15 ← 8 → suitable forms of 16

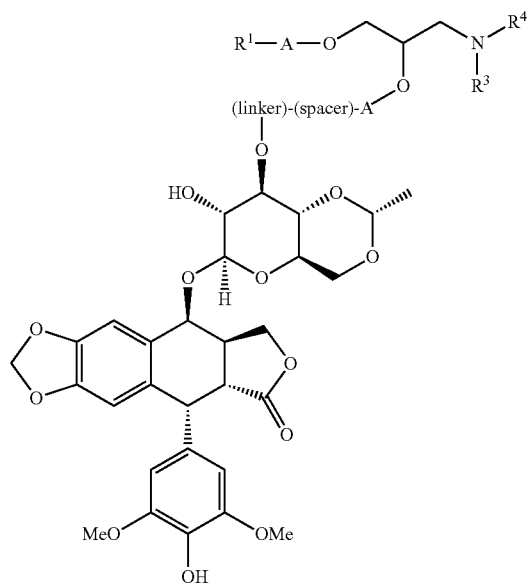
representative monoester, carbamate, or silyl ether
derivative of etoposide of the type 14
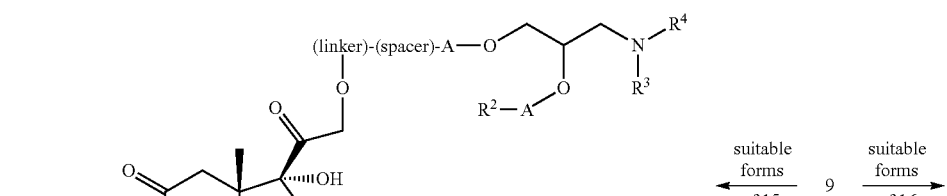
representative monoester,
carbamate, or silyl ether
derivative of prednisone
of the type 13
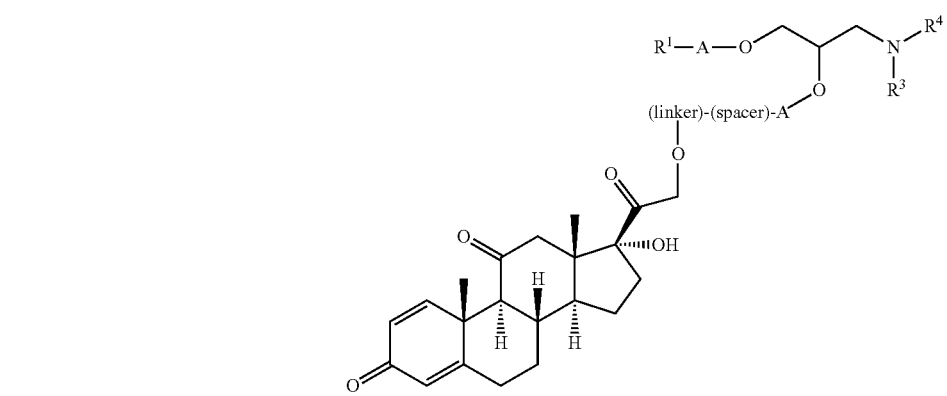
representative monoester,
carbamate, or silyl ether
derivative of prednisone
of the type 14

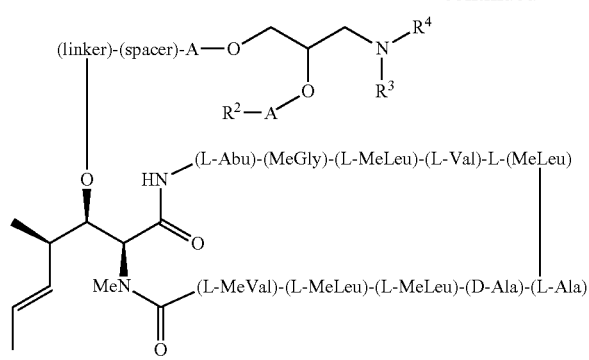
representative ester, carbamate, or silyl ether derivative of cyclosporin of the type 13
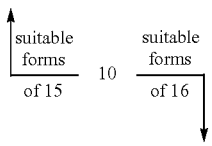
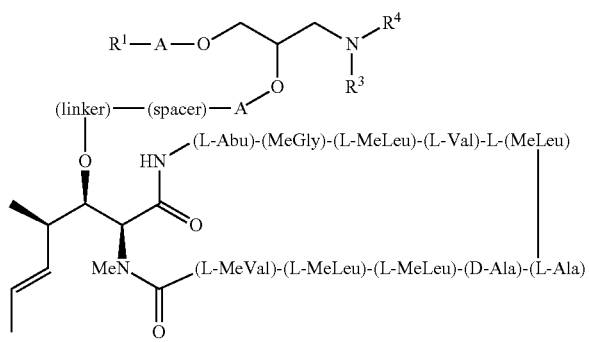
representative ester, carbamate, or silyl ether derivative of cyclosporin of the type 14
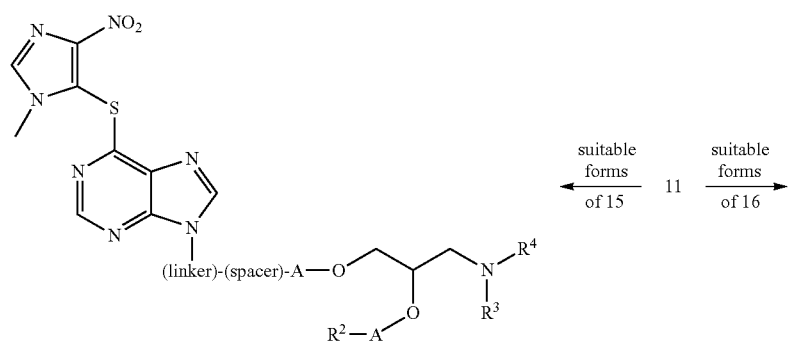
representative derivative of azathioprine of the type 13

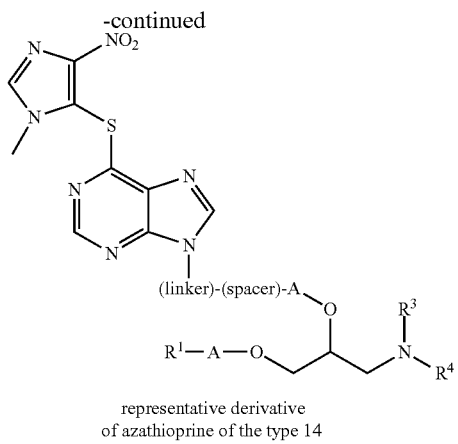

representative derivative
of azathioprine of the type 14

In some aspects, the drug is a new chemical entity (NCE) selected, e.g., from a combinatorial library, for therapeutic efficacy and one or more properties, such as lipophilicity and/or low aqueous solubility, that would interfere with the pharmaceutical utility of the drug absent the instant methods.

In further aspects, drug derivatives are prepared by modifying a newly discovered and/or characterized drug (e.g., a new chemical entity (NCE)). Often pharmacologically potent hits from chemical library screens prove to be less than ideal candidates for pharmaceutical development and use. For example, solubility issues are the main reasons that most NCEs do not advance in development and are discarded. The chemistry platform outlined herein enables development and use of such compounds by specifically modifying them with weak-base chemical moieties that promote formulation in LN using known methods. The integration of high-throughput combinatorial chemistry methods for generating and screening drug candidates with the medicinal chemistry platform described herein provides an alternative approach for the development of drugs (and diagnostic agents) that can replace existing drug development strategies predicated on finding compounds with drug-like properties.

Accordingly, in some aspects, methods are provided herein for identifying drug candidates having a therapeutic activity of interest and low aqueous solubility, lipophilicity, and/or other properties that would prevent or interfere with use of the free compound and/or prevent efficient loading of the compound into LN. For example, in some aspects, methods are provided comprising the steps of: screening a population of compounds produced through combinatorial chemistry to identify drug candidates having a therapeutic activity of interest, and screening the drug candidates for one or more additional properties to identify candidates for derivatization according to methods described herein. In further aspects, the candidates for derivatization are derivatized with a weakly basic group, actively loaded into LN, and the LN are screened to identify formulation candidates having a desired therapeutic activity. Advantageously, screening methods provided herein identify drug candidates for use in LN formulations that would otherwise not be detected using standard methods.

Liposomes used in methods and compositions provided herein can be formed from standard vesicle-forming lipids, which generally include neutral and negatively or positively charged phospholipids and a sterol, such as cholesterol. The selection of lipids is generally guided by consideration of, e.g., liposome size, stability of the liposomes in the bloodstream, the desired release rate, and other factors known in the art.

In some aspects, the major lipid component of liposomes used in methods and compositions described herein is phosphatidylcholine. Phosphatidylcholines having a variety of acyl chain groups of varying chain length and degree of saturation may be used. In some aspects, phosphatidylcholines containing saturated fatty acids with carbon chain lengths in the range of $C_{14}$ to $C_{22}$ are preferred. Saturated long-chain phosphatidylcholines are less permeable and more stable in vivo than their unsaturated counterparts. Phosphatidylcholines with mono- or di-unsaturated fatty acids and mixtures of saturated and unsaturated fatty acids may also be used. Other suitable lipids include, e.g., etherlipids in which the fatty acids are linked to glycerol via ether linkages rather than ester linkages. Liposomes used herein may also be composed of sphingomyelin or phospholipids with head groups other than choline, such as ethanolamine, serine, glycerol, phosphatidic acid and inositol.

In some preferred aspects, liposomes include a sterol, preferably cholesterol, at molar ratios of from 0.1 to 1.0 (cholesterol:phospholipid). Examples of preferred liposome compositions include distearoylphosphatidylcholine/cholesterol, dipalmitoylphosphatidylcholine/cholesterol, dimyristoylphosphatidylcholine/cholesterol and egg sphingomyelin/cholesterol.

In other aspects, liposomes can contain negatively or positively charged lipids. Examples of useful negatively charged lipids include, but are not limited to dimyrystoyl, -dipalmitoyl- and distearoylphasphatidylglycerol, dimyrystoyl, -dipalmitoyl- and dipalmitoylphosphatidic acid, dimyrystoyl, -dipalmitoyl- and dipalmitoylphosphatidylethanolamine, their unsaturated diacyl and mixed acyl chain counterparts as well as cardiolipin. Not limiting examples of positively charged lipids include N,N'-dimethyl-N,N'-dioctacyl ammonium bromide (DDAB) and chloride DDAC), N-(1-(2,3-dioleyloxy)propyl)-N,N,N-trimethylammonium chloride (DOTMA), 3β-[N—(N',N'-dimethylaminoethyl)carbamoyl) cholesterol (DC-chol), 1,2-dioleoyloxy-3-[trimethylammonio]-propane (DOTAP), 1,2-dioctadecyloxy-3-[trimethylammonio]-propane (DSTAP), and 1,2-dioleoyloxypropyl-3-dimethyl-hydroxyethyl ammonium chloride (DORI) and cationic lipids described in e.g. B. Martin, M. Sainlos, A. Aissaoui, N. Oudrhiri, M. Hauchecorne, J.-P. Vigneron, J.-M. Lehn and P. Lehn The design of cationic lipids for gene delivery. *Current Pharmaceutical Design* 2005, 11, 375-394.

In further aspects, liposomes used herein are coated with a polymer layer to enhance stability of the LN in vivo (e.g., sterically stabilized liposomes). For example, in some embodiments, LN are formed from liposomes containing poly(ethylene glycol)-conjugated lipids (PEG-lipids) that form a hydrophilic surface layer that improves the circulation half-life of LN and enhances the amount of LN that reach therapeutic targets, such as a site of infection or a tumor site. The general approach is described, e.g., in Working et al. J Pharmacol Exp Ther, 289: 1128-1133 (1999); Gabizon et al., J Controlled Release 53: 275-279 (1998); AdlakhaHutcheon et al., Nat Biotechnol 17: 775-779 (1999); and Koning et al., Biochim Biophys Acta 1420: 153-167 (1999). Examples of useful PEG-lipids include, but are not limited to, 1,2-Diacyl-sn-Glycero-3-Phosphoethanolamine-N-[Methoxy(Polyethylene glycol)-350] (mPEG 350 PE); 1,2-Diacyl-sn-Glycero-3-Phosphoethanolamine-N-[Methoxy(Polyethylene glycol)-550] (mPEG 550 PE); 1,2-Diacyl-sn-Glycero-3-Phosphoethanolamine-N-[Methoxy(Polyethylene glycol)-750] (mPEG 750 PE); 1,2-Diacyl-sn-Glycero-3-Phosphoethanolamine-N-[Methoxy(Polyethylene glycol)-1000] (mPEG 1000 PE); 1,2-Diacyl-sn-Glycero-3-Phosphoethanolamine-N-[Methoxy(Polyethylene glycol)-2000] (mPEG 2000 PE); 1,2-Diacyl-sn-Glycero-3-Phosphoethanolamine-N-[Methoxy(Polyethylene glycol)-3000] (mPEG 3000 PE); 1,2-Diacyl-sn-Glycero-3-Phosphoethanolamine-N-[Methoxy(Polyethylene glycol)-5000] (mPEG 5000 PE); N-Acyl-Sphingosine-1-[Succinyl (Methoxy Polyethylene Glycol) 750] (mPEG 750 Ceramide); N-Acyl-Sphingosine-1-[Succinyl(Methoxy Polyethylene Glycol) 2000] (mPEG 2000 Ceramide); and N-Acyl-Sphingosine-1-[Succinyl(Methoxy Polyethylene Glycol) 5000] (mPEG 5000 Ceramide).

A variety of methods are available for preparing liposomes as described, e.g., in Szoka et al., Ann. Rev. Biophys. Bioeng. 9:467 (1980); U.S. Pat. Nos. 4,235,871, 4,501,728, and 4,837,028; Liposomes, Marc J. Ostro, ed., Marcel Dekker, Inc., New York, 1983, Chapter 1; and Hope, et al., Chem. Phys. Lip. 40:89 (1986), all of which are incorporated herein by reference. In some preferred aspects, the liposomes are small, approximately 100 nm in diameter liposomes generated by extruding hydrated lipid dispersions through filters with 100 nm pores, as described generally in Hope et al., Biochim. Biophys. Acta, 812: 55-65 (1985), incorporated herein by reference.

In one method, multilamellar vesicles of heterogeneous sizes are produced by dissolving vesicle-forming lipids in a suitable organic solvent or solvent system and drying the mixture under vacuum or an inert gas to form a thin lipid film. Alternatively, the lipids may be dissolved in a suitable solvent, such as tertiary butanol, and then lyophilized to form a more homogeneous lipid mixture. The film or powder is covered with an aqueous buffered solution of a monovalent or divalent metal ion and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate. In another method, the lipids are dissolved in a water-miscible organic solvent such as ethanol and then combined with the aqueous buffer to form a multilamellar liposome suspension. Alternatively, the lipids are dissolved in a water-immiscible organic solvent, mixed with the aqueous medium and liposomes formed by evaporation of the organic solvent.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization or microfluidization are other methods which rely on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane or an asymmetric ceramic membrane is a very effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

In some aspects, methods are provided for loading a weak base derivative into liposomes using an active loading technique. In some aspects, liposomes are loaded by imposing a pH gradient across the liposome membrane (wherein the liposome interior is acidic) and incubating the liposome with the drug to be encapsulated, as described, e.g., in Maurer, N., Fenske, D., and Cullis, P. R. (2001) Developments in liposomal drug delivery systems. Expert Opinion in Biological Therapy 1, 923-47; N. L. Boman, D. Masin, L. D. Mayer, P. R. Cullis and M. B. Bally (1994) "Liposomal Vincristine Which Exhibits Increased Drug Retention and Increased Circulation Longevity Cures Mice Bearing P388 Tumors", Cancer Res. 54, 2830-2833; D. N. Waterhouse, T. D. Madden, P. R. Cullis, M. B. Bally, L. D. Mayer, M. Webb, Preparation, characterization, and biological analysis of liposomal formulations of vincristine. Methods Enzymol. 391 (2005) 40-57, hereby incorporated by reference. In some preferred aspects, the pH gradient is an ammonium sulfate gradient, as described generally in G. Haran, R. Cohen, L. K. Bar, Y. Barenholz, Transmembrane ammonium sulfate gradients in liposomes produce efficient and stable entrapment of amphipathic weak bases. Biochim. Biophys. Acta 1115 (1993) 201-215 and U.S. Pat. No. 5,316,771, hereby incorporated by reference. Once the drug has been loaded into the liposomes, the compositions can be used directly, or the composition can be further treated to remove any unloaded drug.

pH loading techniques generally involve two steps, the generation of the pH gradient with low intraliposomal pH and the subsequent loading of the drug. Transmembrane proton gradients can be generated by a variety of ways. Liposomes can be prepared in a low pH buffer such as a pH 4 citrate buffer followed by exchange of the external buffer solution against a pH 7.5 buffer (e.g. Madden et al., *Chem. Phys. Lipids,* 53:37-46 (1990)). Alternatively, ionophores can be used in conjunction with cation gradients (high internal cation concentrations) (e.g. Fenske et al., *Biochim Biophy. Acta,* 1414: 188-204 (1998)). Ionophores such as nigericin and A23187 couple the outward movement of monovalent or divalent cations, respectively, to the inward movement of protons thus acidifying the liposome interior. Furthermore, liposomes can be prepared in the presence of high concentrations of a weak base such as ammonium sulfate (Haran et al., *Biochim. Biophys. Acta,* 1151:201-215 (1993)). Removal of the external ammonium salt solution results in the generation of a pH gradient according to the same principle, which is also responsible for the subsequent drug loading process. The ammonium sulfate loading technique does not require a large pH gradient to achieve efficient loading, as the loading process is sustained by an exchange of the two different amines (drug goes in, ammonia comes out) and hence works well at very low external pH. This is an advantage if, for example, the drug is unstable or insoluble at neutral pH. In addition to pH gradients, metal ion gradients can be used for active loading (e.g. Cheung et al., *Biochim Biophys Acta,* 1414:205-216 (1998)). This loading method relies the same basic principles as the pH gradient technique. The neutral form of the weak base drug can permeate across the membrane and is retained in the aqueous interior of the liposomes through formation of a drug-metal ion complex.

For loading of water-soluble weak base drugs into LN, the drug can be dissolved in an aqueous solution (e.g. 300 mM sucrose, or isotonic buffer solutions with appropriate pH), combined with the liposome suspension and then incubated at appropriate temperature. The drug solution can contain a small (non-membrane permeabilizing) amount of a water-miscible organic solvent to increase the solubility of the drug (e.g. <10% ethanol). The incubation temperature and time depend on the lipid composition and the nature of the drug. Typically, liposomes composed of cholesterol and long-chain saturated fatty acids such as DSPC/chol LN are less permeable than LN formed from short-chain saturated lipids (e.g. DMPC/chol) or unsaturated lipids and require higher temperatures to achieve rapid and efficient loading. For example, DSPC/chol LN typically require temperatures equal or higher than 60° C.; loading is typically complete after 5-15 minutes, but may take up to 2 hours.

For loading of lipophilic weak base drugs, the drug can be treated like a lipid. For example, lipids and drug can be co-mixed and liposomes formed as described above; the lipophilic drug is then distributed between the two monolayers of the liposome bilayer. The drug in the external monolayer is then loaded into the liposome interior (flipped to the inner monolayer of the LN bilayer) in response to a trans-membrane pH or other ion gradient using the methods described above.

In additional aspects, pharmaceutical compositions are provided comprising a LN formulation provided herein. Also provided herein are methods for treating a disease or condition, comprising administering a LN composition provided herein. In yet further aspects, kits are provided comprising an LN composition described herein and instructional material teaching the methodologies and uses of the invention, as described herein.

Pharmaceutical compositions comprising the liposomes and compounds of the invention are prepared according to standard techniques, as well as those techniques described above. Preferably, the pharmaceutical compositions are administered parenterally, i.e., intraanicularly, intravenously, subcutaneously, or intramuscularly. More preferably, the pharmaceutical compositions are administered intravenously by a bolus injection or infusion. Suitable formulations for use in the present invention are found in Remington's Pharmaceutical Sciences, Mack Publishing Company, Philadelphia, Pa., 17th ed. (1985).

Preferably, the pharmaceutical compositions are administered intravenously Thus, this invention provides compositions for intravenous administration which comprise liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous suspension may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, and the like, for example, sodium acetate, sodium lactate, sodium chloride, sodium phosphate, polyethylene glycol ($PEG_{400}$), etc.

The concentration of liposomes, in the pharmaceutical formulations can vary widely, i.e., from less than about 0.5 mg/mL lipid, usually at or at least about 10-50 mg/mL lipid to as much as 100 mg/mL lipid or higher and will be selected primarily by fluid volumes, viscosities, stability, drug dose required, etc., in accordance with the particular mode of administration selected.

Liposome charge is an important determinant in liposome clearance from the blood, with negatively charged liposomes being taken up more rapidly by the reticuloendothelial system (Juliano, Biochem. Biophys. Res. Commun. 63:65 1 (1975)) and thus having shorter half-lives in the bloodstream. Liposomes with prolonged circulation half-lives are typically desirable for therapeutic and diagnostic uses, where liposomes have to accumulate at distal disease sites such as tumors. For instance, liposomes which have circulation half-lives from 2, 8, 12, or up to 24 hours are particularly preferred.

Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, or an anti-oxidant such as ascorbic acid are suitable.

The following examples are provided by way of illustration and are non-limiting.

EXAMPLES

Example 1

Chemical Synthesis Methods

Weak base derivatives and unmodified drugs were quantitated by ultra high performance liquid chromatography (UPLC). The instrument consisted of a Waters® Acquity™ UPLC system equipped with a photodiode array detector (PDA) and a triple-quad (TQ) MS detector; Empower™ data acquisition software version 2.0 was used (Waters, USA). Separations were performed using a Waters® Acquity™ BEH C18 column (1.7 µm, 2.1×100 mm) at a flow rate of 0.25 mL/min, with mobile phases A and B consisting of water with 0.1% trifluoroacetic acid (TFA) and acetonitrile with 0.1% TFA, respectively. For prednisone and etoposide derivatives and unmodified drugs the mobile phases consisted of water with 0.1% formic acid (A) and acetonitrile with 0.1% formic acid (B). The mobile phases were delivered at a programmed linear gradient at a column temperature of 23° C.

For docetaxel derivatives and docetaxel, separation was initiated with a mobile phase ratio of 50:50 (A:B). The ratio was changed to 10:90 (A:B) over a period of 2 min using a linear curve and then maintained at 10:90 (A:B) over a period of 0.5 min. The mobile phase was subsequently changed back to 50:50 (A:B) over a period of 0.1 min and this ratio was maintained for 0.4 min before the next sample was injected. For prednisone derivatives and prednisone, separation was initiated with a mobile phase ratio of 80:20 (A:B). The ratio was changed to 40:60 (A:B) over a period of 4 min using a linear curve and then to 10:90 (A:B) over a period of 0.1 min. The latter ratio was maintained for 0.4 min. The mobile phase was subsequently changed back to 80:20 (A:B) during a span of 0.1 min and this ratio was maintained for 0.9 min before the next sample was injected. For the etoposide derivative and etoposide, separation was initiated with a mobile phase ratio of 80:20 (A:B). The ratio was changed to 72.5:27.5 (A:B)

over a period of 1 min using a linear curve, then to 60:40 (A:B) over a period of 3 min and 10:90 (A:B) over a 0.1 min period. This ratio was maintained for 0.4 min. The mobile phase was subsequently changed back to 80:20 (A:B) during a span of 0.1 min and this ratio was maintained for 0.4 min before the next sample was injected.

The analyte was detected by a PDA and TQ-MS detector at a wavelength of 230 nm (in the case of docetaxel and docetaxel derivatives) and 254 nm (for prednisone and etoposide derivatives) and ES$^+$ ion mode with a cone voltage of 30V, respectively. LN formulated derivatives were solubilized in TFA- or formic acid-acidified ethanol (0.1% vol.). For detection of LN-formulated drugs within blood plasma samples, 50 μL plasma was added to 150 μL methanol acidified with TFA or formic acid (0.1% v/v) and the mixture was centrifuged at 4° C. for 30 min at 10,000×g to pellet the precipitated proteins. Acidification of methanol was necessary to stabilize the prodrugs. The limit of MS detection (LOD) for docetaxel and docetaxel derivative (TD-1) was between about 1-50 ng/mL when TFA-acidified methanol was used. The limit can be decreased to sub nM concentrations if needed by using formic acid in place of TFA.

Unless otherwise indicated, $^1$H and $^{13}$CNMR spectra were recorded at room temperature on Bruker models AV-300 (300 MHz for $^1$H and 75 MHz for $^{13}$C) and AV-400 (400 MHz for $^1$H and 100 MHz for $^{13}$C). Chemical shifts are reported in parts per million (ppm) on the δ scale and coupling constants, J, are in hertz (Hz). Multiplicities are described as "s" (singlet), "d" (doublet), "t" (triplet), "q" (quartet), "dd" (doublet of doublets), "dt" (doublet of triplets), "m" (multiplet), "b" (broad). Low-resolution mass spectra (m/z) were obtained in the electrospray (ESI) mode.

LN formulated derivatives were viewed by Cryo-TEM performed with a Tecnai G2 20 TWIN Mk. 2 Transmission Electron Microscope (CDRD Imaging, Vancouver, Canada). The Instrument was operating at 200 kV in bright-field mode. Digital images were recorded under low dose conditions with a FEI Eagle 4k HR CCD camera and analysis software FEI TIA. An underfocus of 1-3 μm was used to enhance image contrast. Sample preparation was done with a Vitrobot Mark IV vitrification robot on Lacey Formvar 300 grids (#01890 from Ted Pella).

All reagents and solvents were commercial products and were used without further purification. Flash chromatography was performed on Silicycle 230-400 mesh silica gel. Analytic and preparative TLC was carried out with Merck silica gel 60 plates with fluorescent indicator. Spots were visualized with UV light, KMnO$_4$ or p-anisaldehyde.

General Synthetic Strategy

Figure 10:
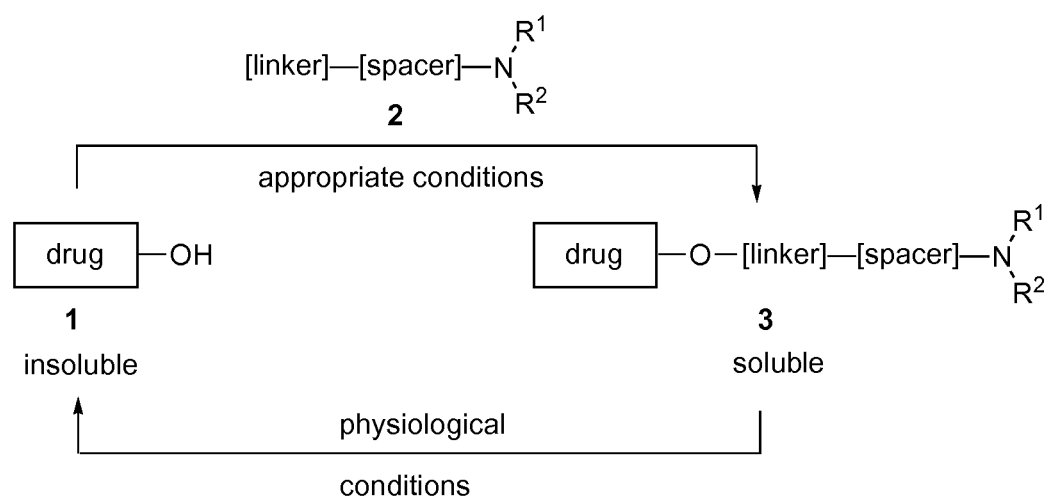
FIG. 10. Schematic illustration of the chemistry strategy employed for the synthesis of weak base drug derivatives based on esterifaction of hydroxyl groups located on the drug.

A general strategy provided herein (FIG. 10) involves the derivatization of a water-insoluble drug 1 that contains an appropriate anchoring site, such as an OH or an NH group, with a properly tailored solubilizing unit represented by the general structure 2. The general scheme also applies to the synthesis of lipophilic weak base drug derivatives. The resultant water-soluble conjugate 3 can be loaded into LN using a pH or ion gradient as the driving force. The derivative 3 is either active by itself and/or is rapidly converted into the active parent drug 1 under physiological conditions.

The technology is based on a number of physical properties of 3, such as (i) water solubility; (ii) pKa of the protonated nitrogen functionality; (iii) stability under liposome loading conditions; (iv) rate of release of the free drug under physiological conditions. In turn, these properties are a function of the nature of the linker, of the spacer, and of groups R$^1$ and R$^2$ in 2.

In some aspects, the solubilizing units comprise a carboxy linker group, a spacer such as n-C$_1$-C$_4$ chain, and an amine group such as N-methylpiperazine, morpholine, piperidine, pyrrolidine, or dimethylamine. Exemplary solubilizing units include:

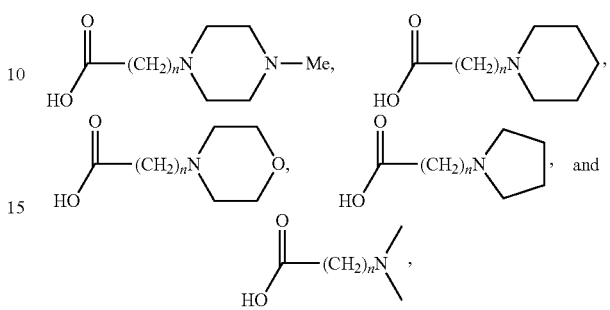

where n is between 1 and about 10, or more preferably 1 and 4.

Example 2

Taxane Derivatives

Docetaxel was derivatized at the hydroxyl group in the C-2' position with N-methyl-piperazinyl butanoic acid to form an amino ester prodrug (TD1), as described below.

2'-O—(N-methyl-piperazinyl butanoic acid ester) Derivative of Docetaxel (TD1)

Linker Synthesis: 4-(4-methylpiperazin-1-yl)butanoic acid hydrochloride

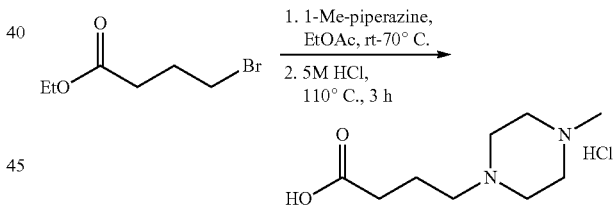

1-methyl piperazine (7.68 mL, 70 mmol, 4 equivalents) was added to a stirred solution of ethyl 4-bromobutanonate (2.5 mL, 17.3 mmol) in ethyl acetate (50 mL) at room temperature. The solution was stirred at 25° C. for 1 h with evolution of a white precipitate, and then heated on an oil bath to 70° C. for 1 h. TLC analysis (20% ethylacetate (EtOAc) in hexanes, Rf=0.9 (starting material), 0.1 (product), visualized with iodine, I2) indicated complete consumption of the bromide reagent. The reaction was diluted with EtOAc (100 mL), transferred to a separatory funnel and the organic phase washed with water (100 mL), sodium bicarbonate (NaHCO$_3$, saturated, 2×100 mL), brine (100 mL), dried over magnesium sulfate (MgSO$_4$) and concentrated to give a slightly yellow oil. The oil was dissolved in methylene chloride (20 mL) and loaded onto a pre-equilibrated plug of silica gel (20% EtOAc in hexanes, 150 mL SiO$_2$). The desired product was eluted from the silica with increasingly polar eluent (first with 20% EtOAc in hexanes, then with 5-25% MeOH (containing 5% NH$_4$OH) in EtOAc).

Fractions containing the desired material were pooled and concentrated to give ethyl-4-(4-methylpiperazin-1-yl)butanoate (3.63 g, quantitative). Water (20 mL) and hydrochloric acid (HCl, 10M, 20 mL, 10 equivalents) were added to the flask containing the resulting oil. The flask was fitted with a reflux condenser and heated at 110° C. for 3 h. The reaction mixture was then allowed to cool to room temperature and was subsequently concentrated under vacuum until there was only an oily residue remaining. The residue was re-dissolved in distilled water and the concentration process repeated. The remaining syrup was dissolved in ethanol (50 mL) at 85° C. Addition of a small quantity of water (~1 mL) was required to dissolve all solids (adding larger volumes of water will adversely affect yield). The solution was allowed to stand at room temperature for 3 h and was then transferred to a refrigerator (5° C.) for 16 h. The precipitate was filtered off, transferred to a pre-weighed vial and placed in a desiccator over Drierite at high vacuum for 16 h to give 4-(4-methylpiperazin-1-yl)butanoic acid hydrochloride as a crystalline and non hygroscopic material (3.02 g, 80% based on the mono HCl salt).

1H NMR (D$_2$O, 400 MHz) δ (ppm)=3.60 (br s, 8H), 3.26-3.22 (m, 2H), 2.93 (s, 3H), 2.43 (t, J=7.0 Hz, 2H), 1.99-1.91 (m, 2H). $^{13}$C NMR (D2O, 100 MHz) δ (ppm)=176.5, 55.9, 50.2, 48.7, 42.8, 30.3, 18.7.

Esterification and salt formation: TD-1hydrochloride salt ice bath and Mukaiyama reagent (2-chloro-1-methylpyridinium iodide, 1.667 g, 6.53 mmol, 1.32 equiv) was added. The solution went yellow with the dissolution of the pyridinium salt. The flask was removed from the ice bath after 30 minutes and the reaction was allowed to proceed for an additional 16 h. TLC indicated good, but incomplete conversion of the starting material to the desired product (8% MeOH (with 5% NH$_4$OH) in CH$_2$Cl$_2$, stained with 5% H$_2$SO$_4$ in ethanol). An additional 0.5 equivalents of the pyridinium salt (0.632 g, 0.5 equiv) and amino acid (0.120 g, 0.1 equiv) was added to the ice-cooled solution while stirring. After 3 h the reaction mixture was concentrated on a rotary evaporator at high vacuum to yield a slightly orange solid. The solid was dissolved in CH$_2$Cl$_2$ (150 mL) and EtOAc (20 mL), transferred to a separatory funnel and partitioned between the organic phase and a saturated NaHCO$_3$ solution (100 ml). The organic phase was then washed with brine (100 mL), dried over MgSO$_4$, filtered and concentrated to give a slightly golden syrup. The syrup was dissolved in CH$_2$Cl$_2$ (20 mL), loaded onto a pre-equilibrated silica gel column (4% MeOH (with 5% NH$_4$OH) in CH$_2$Cl$_2$, 250 mL, 40 mm diameter) and eluted with increasingly polar solvent (4-10% MeOH (with 5% NH$_4$OH) in CH$_2$Cl$_2$, 2% increments, 500 mL/increment).

The fractions containing the desired material were collected and concentrated to yield 3.8909 g (80.5%) of compound. $^1$H NMR analysis of the compound indicated good purity, with the presence (~10%) of peaks attributed to a regioisomer. The material was re-dissolved in CH$_2$Cl$_2$ and

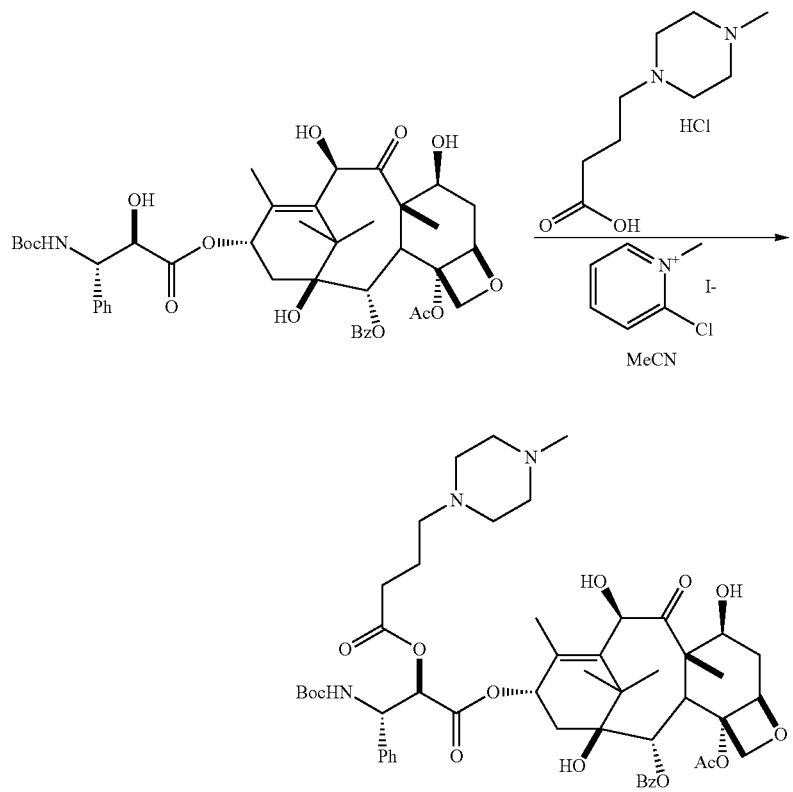

Triethylamine (NEt$_3$, 10.0 mL, 5 equivalents) was added to a stirred solution of docetaxel (3.997 g, 4.95 mmol) and 4-(4-methylpiperazin-1-yl)butanoic acid hydrochloride (1.213 g, 5.44 mmol, 1.1 equivalents) in dichloromethane (CH$_2$Cl$_2$, 60 mL). The reaction vessel was then cooled in an subjected to the same chromatographic conditions described above, using 1% increments of MeOH in CH$_2$Cl$_2$ from 5-10% (500 mL/increment). Fractions containing pure material were identified by TLC, collected and concentrated to give 2.96 g of compound with a clean NMR spectrum.

The material was dissolved in 2-propanol (45 mL) and HCl (6.3 mL, 1M in diethylether (Et$_2$O), 2.05 equivalents) was added dropwise under cooling (0° C.) to generate the hydrochloride salt. The suspension was concentrated to dryness, and the resulting cream colored solid was dried at high vacuum and re-crystallized from 2-propanol (45 mL) by the addition of Et$_2$O (10 mL). The precipitate was filtered off on a Buchner funnel and dried at high vacuum for 18 h yielding ~2.5 g. The docetaxel derivative (TD-1) was characterized by NMR, mass spectroscopy, elemental analysis and UHPLC-UV to confirm identity and purity. Chromatographic purity by UHPLC-UV was 96.7%.

$^1$H NMR (400 MHz, D$_2$O): δ (ppm)=8.11 (d, J=7.4 Hz, 2H), 7.65 (t, J=7.4 Hz, 1H), 7.56 (t, J=7.7 Hz, 2H), 7.43-7.37 (m, 4H), 7.25 (br t, J=6.2 Hz, 1H), 6.09 (m, 1H), 5.61 (d, J=7.1 Hz, 1H), 5.32 (m, 1H), 5.27-5.24 (m, 2H), 4.99 (d, J=8.1 Hz, 1H), 4.22-4.13 (m, 3H), 3.83 (br d, J=6.8 Hz, 1H), 3.61 (s, 1H), 3.21-3.09 (m, 2H), 2.67-2.33 (m, 6H), 2.23-2.17 (m, 1H), 2.12-1.98 (m, 2H), 1.97-1.76 (m, 5H), 1.68 (s, 3H), 1.40 (s, 9H), 1.15 (s, 3H), 1.11 (s, 3H).

$^{13}$C NMR (100 MHz, D$_2$O): δ (ppm)=211.22, 173.26, 172.48, 170.57, 167.58, 157.22, 138.72, 136.13, 134.48, 129.96, 129.29, 129.00, 128.77, 126.95, 84.49, 80.87, 78.51, 76.55, 75.55, 75.04, 74.26, 72.65, 71.28, 57.39, 55.59, 50.32, 48.78, 46.29, 42.83, 42.68, 35.25, 34.73, 30.13, 29.83, 29.60, 27.51, 25.900, 23.69, 22.43, 20.75, 18.77, 16.78, 13.60, 9.55.

Elemental analysis: calculated based on TD-1+2HCl+1H$_2$O: C, 58.53; H, 6.90; Cl, 6.65; N, 3.94; Obs.: C, 58.50; H, 6.97; Cl, 6.58; N, 4.13; HPLC/MS (m/z); 977.4 (m+H), 96.7% area by UPLC-UV.

TD1 Analogs

TD1 contains a dibasic amino acid ester at O-2' that is believed to assist in the directed release of the parent compound (docetaxel) through neighboring group participation. A series of TD1 analogs were synthesized as described below. The analogues have variations in the chain length of the amino-acyl linker and the structure of the basic amino-acyl moiety designed to modulate the rate of ester hydrolysis via anchimeric assistance (Pop et al., *Pharmaceutical Research*, 13(3):469-475 (1996); Rautio et al., *J. Med. Chem.*, 43(3): 1489-1494 (2000)), allowing the rate at which the parent compound is released to be fine-tuned for various therapeutic applications.

For a ring closing reaction, 3-7 membered ring transition states are favored when the reaction centre is sp$^2$ hybridized, as in the case of intramolecular ester hydrolysis. There are two possible modes of hydrolysis: Mode A, in which the amine acts directly at the carbonyl to generate the parent drug and an activated acyl-ammonium intermediate; and Mode B, in which the amine acts as a general base to increase the nucleophilicity of the solvent (water in this case), thereby increasing the rate of hydrolysis and ejecting the zwitterionic amino acid. The TD1 analogues synthesized below all allow for hydrolysis by Mode A. Only shorter amino acid esters (n=1-3) allow hydrolysis by Mode B.

In the first series of analogues, the weak-base solubilization unit comprises a piperazinyl amino moiety with an alkyl linker of varying lengths relative to TD1. In the next series of analogues, the same alkyl linkers were used and the amino moiety was varied to include morpholino and piperidinyl substituents. The amino moieties vary in nucleophilicity according to the order: N-methyl piperazine>morpholine>piperidine (e.g., Baldwin, *J. Chem. Soc. Chem. Commun.*, 734-736 (1976); Baldwin et al., *J. Org. Chem.*, 42(24):3846-3852 (1977)). Basicity is inverted, with N-methyl piperidine having a pK$_a$ of 2 units higher than N-methyl piperazine. As such, the N-methyl piperazino compounds are expected to be more susceptible to Mode A hydrolysis and to require lower pH values to achieve protonation.

N-alkylation to amino-ester (general procedure)

tert-butyl 3-(4-methylpiperazin-1-yl)propanoate

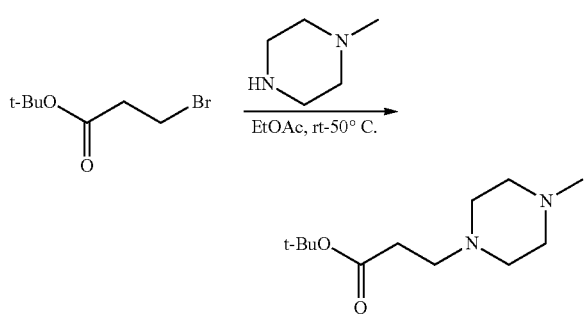

4-methyl piperazine (7.68 mL, 70 mmol, 4 equiv) was added to a stirred solution of tert-butyl 3-bromopropionate (3.0 mL, 18 mmol) in ethyl acetate (15 mL) at 0° C. The solution was stirred at 25° C. for 1 h with evolution of a white precipitate, then heated on an oil bath to 55° C. for 2 h. TLC analysis (20% EtOAc in Hexanes, R$_f$=0.9 (starting material), 0.1 (product)) indicated complete consumption of the bromide reagent. The reaction was diluted with EtOAc (100 mL) and transferred to a separatory funnel, and the organic phase was washed with water (100 mL), NaHCO$_3$ (sat'd, 2×100 mL), and brine (100 mL), dried over MgSO$_4$ and concentrated to give a slightly yellow oil. The oil was dissolved in methylene chloride (20 mL), loaded on to a pre-equilibrated plug of silica gel (20% EtOAc in Hexanes, 150 mL SiO$_2$) and the desired product was eluted from the silica with increasingly polar eluent (EtOAc in hexanes, starting at 20%, 200 mL volumes increasing in 15% increments to 100%). Fractions containing the desired material were concentrated to give tert-butyl 3-(4-methylpiperazin-1-yl)propanoate (4.1 g, quantitative). $^1$H NMR (400 MHz, CDCl$_3$) δ (ppm)=3.45 (d, J=3 Hz, 2H), 2.64 (t, J=7.3 Hz, 2H), 2.47 (br s, 6H), 2.38 (t, J=7.3 Hz, 2H), 2.25 (s, 3H), 1.42 (s, 9H).

The same general procedure was used to prepare the following analogs:

Benzyl 2-(4-methylpiperazin-1-yl)acetate

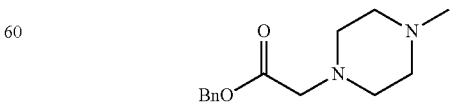

$^1$H NMR (400 MHz, CDCl$_3$) δ (ppm)=7.33-7.27 (m, 5H), 5.15 (s, 2H), 3.25 (s, 2H), 2.60 (br s, 4H), 2.48 (br s, 4H), 2.27 (s, 3H).

Ethyl 5-(4-methylpiperazin-1-yl)pentanoate

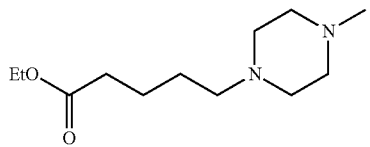 [SMILES: CCOC(=O)CCCCN1CCN(C)CC1]

¹H NMR (400 MHz, CDCl₃) δ (ppm)=4.10 (q, J=7.2 Hz, 2H), 2.43 (br s, 6H), 2.35-2.28 (m, 4H), 2.26 (s, 3H), 1.79 (br s, 2H), 1.62 (p, J=7.2 Hz, 2H), 1.54-1.46 (m, 2H), 1.23 (t, 7.2 Hz).

Benzyl 2-morpholinoacetate

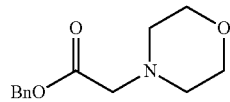

¹H NMR (400 MHz, CDCl₃) δ (ppm)=7.46-7.30 (m, 5H), 5.16 (s, 2H), 3.74 (t, J=4.7 Hz, 4H), 3.25 (s, 2H), 2.58 (t, J=4.7 Hz, 4H).

Tert-butyl 3-morpholinopropanoate

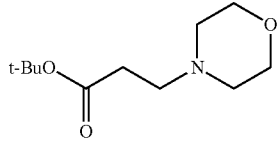 [SMILES: CC(C)(C)OC(=O)CCN1CCOCC1]

¹H NMR (400 MHz, CDCl₃) δ (ppm)=3.68 (t, J=4.5, $H), 2.63 (t, J=7.3 Hz, 2H), 2.44 (t, J=4.5 Hz, 4H), 2.39 (t, J=7.3 Hz, 2H), 1.44 (s, 9H).

Ethyl 4-morpholinobutanoate

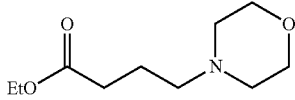

¹H NMR (400 MHz, CDCl₃) δ (ppm)=4.11 (q, J=7.1 Hz, 2H), 3.68 (t, j=4.7 Hz, 4H), 2.42-2.38 (m, 4H), 2.37-2.31 (m, 4H), 1.80 (p, J=7.3 Hz, 2H), 1.24 (q, J=7.1 Hz, 3H).

Ethyl 5-morpholinopentanoate

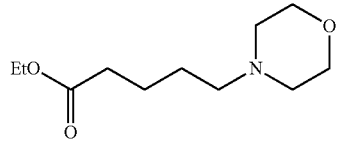 [SMILES: CCOC(=O)CCCCN1CCOCC1]

¹H NMR (400 MHz, CDCl₃) δ (ppm)=4.11 (q, J=7.1 Hz, 2H), 3.68 (t, j=4.7 Hz, 4H), 2.42-2.38 (m, 4H), 2.37-2.27 (m, 4H), 1.80-1.73 (m, 2H), 1.53-1.45 (m, 2H), 1.24 (q, J=7.1 Hz, 3H).

Hydrolysis to Amino Acid (General Procedure)

3-(4-methylpiperazin-1-yl)propanoic acid hydrochloride (TD11)

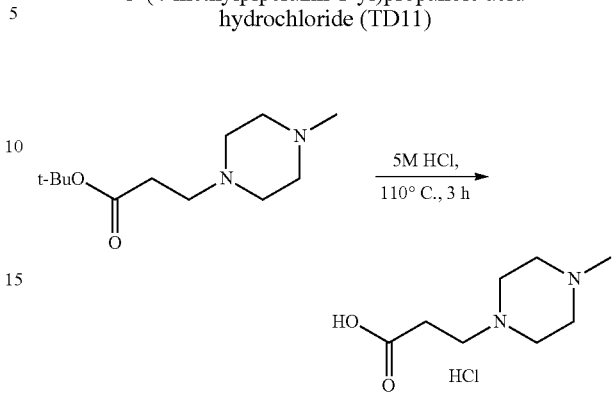

To a round bottom flask containing tent-butyl 3-(4-methylpiperazin-1-yl)propanoate (4.1 g, 18 mmol), was added a magnetic stir bar, water (20 mL) and HCl (10M, 20 mL, 10 equiv). The flask was fitted with a reflux condenser, placed in an oil bath and heated to a bath temperature of 110° C. for 3 h. No TLC analysis of this reaction was conducted. The reaction removed from the oil bath and allowed to cool to room temperature. Once the reaction had cooled sufficiently, it was transferred to a rotary evaporator connected to an oil-driven high vacuum pump. The contents of the flask were concentrated until pressure was 0.1 mm Hg and there was only an oily residue remaining. The flask was then removed, the contents re-dissolved in distilled water and the evaporation process was repeated, this time yielding a syrup that foamed when subjected to high vacuum after water removal. It should be noted that if the crude material has any significant amount of residual HCl, the acid will re-esterify when subjected to the following conditions for crystallization, adversely affecting yield. Ethanol (50 mL) and a magnetic stir bar were added and the flask was submerged in an oil bath at 85° C. to dissolve the syrup. Even at reflux not all of the material would dissolve so a small quantity of water (~1 mL) was added in a dropwise fashion until all solids dissolved. If excessive amounts of water are added at this time it will adversely affect yield.

The resulting solution was removed from the oil bath and allowed to stand at room temperature for 3 h before being transferred to a refrigerator (5° C.) for 16 h. The solids were suspended by sonicating to loosen them from the sides of the flask and filtered on to a filter paper lined Buchner funnel. The crystals were then transferred to a pre-weighed vial which was placed in a desiccator over Drierite, at high vacuum for 16 h to give solid, air-stable, crystalline and non hygroscopic material (3.07 g, 82% based on the mono HCl salt). ¹H NMR (D₂O, 400 MHz) δ (ppm)=3.6 (br s, 8H), 3.48 (t, J=6.8 Hz, 2H), 2.93 (s, 3H), 2.83 (t, J=6.8 Hz, 2H).

The same general procedure was used to prepare the following analogs:

2-(4-methylpiperazin-1-yl)acetic acid hydrochloride (TD2)

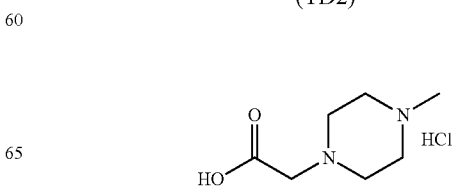

¹H NMR (D₂O, 400 MHz) δ (ppm)=3.87 (s, 2H), 3.85-3.35 (br m, 8H), 2.93 (s, 3H).

5-(4-methylpiperazin-1-yl)pentanoic acid hydrochloride (TD3)

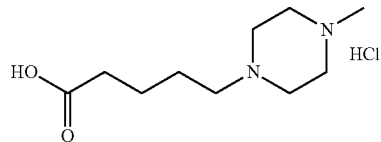

¹H NMR (D₂O, 400 MHz) δ (ppm)=3.59 (br s, 8H), 3.22 (t, J=7.8 Hz, 2H), 2.93 (s, 3H), 2.36 (t, J=7.2 Hz, 2H), 1.75-1.69 (m, 2H), 1.57 (p, J=7.8 Hz).

4-morpholinobutanoic acid hydrochloride (TD4)

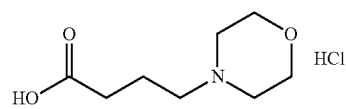 [SMILES: O=C(O)CCCN1CCOCC1 ; Cl]

¹H NMR (D₂O, 400 MHz) δ (ppm)=4.02 (br d, J=12.3 Hz, 2H), 3.73 (br t, J=12.3 Hz, 2H), 3.46 (br d, J=12.3 Hz, 2H), 3.15-3.06 (m, 4H), 2.41 (t, J=7.1 Hz, 2H), 1.97-1.89 (m, 2H).

2-morpholinoacetic acid hydrochloride (TD5)

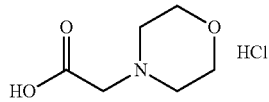

¹H NMR (D₂O, 400 MHz) δ (ppm)=4.10-3.70 (m, 6H), 3.50 (br s, 2H), 3.2 (br s, 2H).

3-morpholinopropanoic acid hydrochloride (TD6)

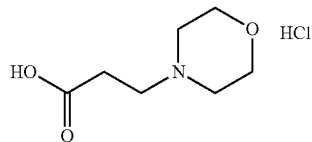 [SMILES: O=C(O)CCN1CCOCC1 ; Cl]

¹H NMR (D₂O, 400 MHz) δ (ppm)=4.02 (br d, J=12.3 Hz, 2H), 3.73 (br t, J=12.3 Hz, 2H), 3.46 (br d, J=12.3 Hz, 2H), 3.39 (t, J=7.0 Hz, 2H), 3.13 (br t, J=12.3 Hz, 2H), 2.79 (t, J=7.0 Hz, 2H).

5-morpholinopentanoic acid hydrochloride (TD12)

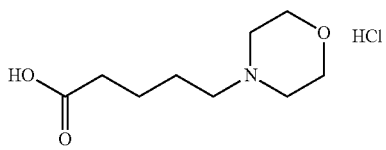 [SMILES: O=C(O)CCCCN1CCOCC1 ; Cl]

¹H NMR (D₂O, 400 MHz) δ (ppm)=4.02 (br d, J=12.3 Hz, 2H), 3.73 (br t, J=12.3 Hz, 2H), 3.46 (br d, J=12.3 Hz, 2H), 3.15-3.06 (m, 4H), 2.41 (t, J=7.1 Hz, 2H), 1.72-1.66 (m, 2H), 1.60-1.52 (m, 2H).

4-(piperidin-1-yl)butanoic acid hydrochloride (TD7)

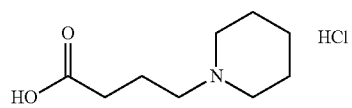 [SMILES: O=C(O)CCCN1CCCCC1 ; Cl]

¹H NMR (D₂O, 400 MHz) δ (ppm)=3.43 (br d, J=12.1 Hz, 2H), 3.04-2.99 (m, 2H), 2.88 (td, J=2.7, 12.1 Hz, 2H), 2.38 (t, J=7.1 Hz, 2H), 1.95-1.80 (m, 4H), 1.76-1.55 (m, 3H), 1.45-1.32 (m, 1H).

2-(piperidin-1-yl)acetic acid hydrochloride (TD8)

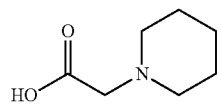

5-(piperidin-1-yl)pentanoic acid hydrochloride (TD9)

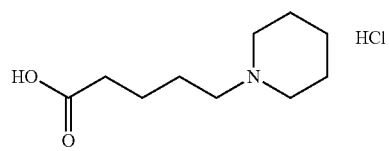 [SMILES: O=C(O)CCCCN1CCCCC1 ; Cl]

¹H NMR (D₂O, 400 MHz) δ (ppm)=3.43 (br d, J=12.1 Hz, 2H), 3.04-2.99 (m, 2H), 2.80 (td, J=2.7, 12.1 Hz, 2H), 2.38 (t, J=7.1 Hz, 2H), 1.88-1.78 (m, 2H), 1.76-1.49 (m, 7H), 1.45-1.32 (m, 1H).

3-(piperidin-1-yl)propanoic acid hydrochloride (TD13)

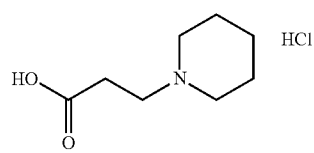 [SMILES: O=C(O)CCN1CCCCC1 ; Cl]

¹H NMR (D₂O, 400 MHz) δ (ppm)=3.43 (br d, J=12.1 Hz, 2H), 3.29 (t, J=7.1 Hz, 2H), 2.88 (td, J=2.7, 12.1 Hz, 2H), 2.76 (t, J=7.1 Hz, 2H), 1.85-1.80 (m, 2H), 1.76-1.62 (m, 3H), 1.45-1.32 (m, 1H).

2'-O-acylation (general procedure)
TD4: Morpholino butanoic acid ester

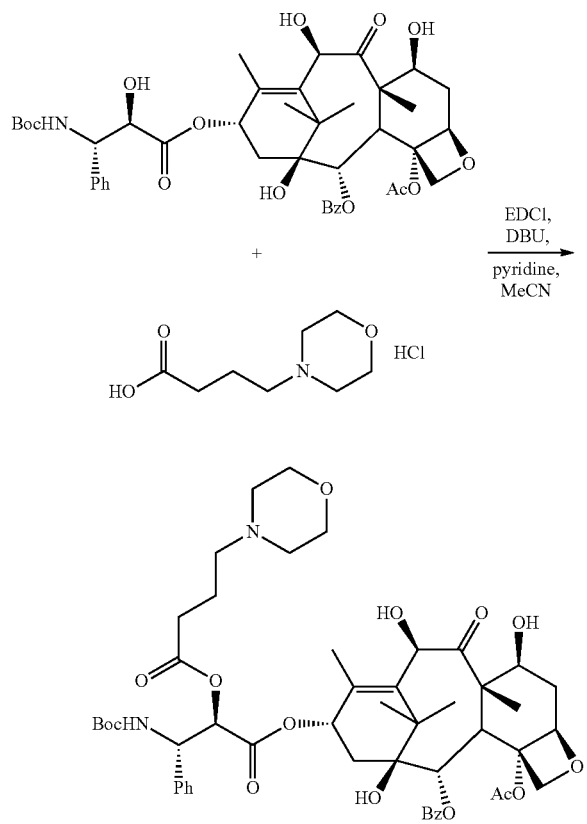

A stirred solution of 4-morpholinobutanoic acid hydrochloride (0.095 g, 0.45 mmol, 1.2 equiv) in pyridine (4 mL) and DBU (0.140 mL, 3 equiv) in a 25 mL round bottom flask was cooled in an ice bath at 0° C. and acetonitrile (2 mL) was added, followed by Taxotere® (0.303 g, 0.375 mmol, 1 equiv). 1-ethyl-3-(3'-dimethylaminopropyl)carbodiimide (EDCI, 0.180 g, 2.5 equiv) was added in portions over 15 minutes. The resulting suspension was stirred, gradually warming to room temperature as the ice bath melted over the course of 16 h. TLC analysis (30% Hexanes in EtOAc/6% MeOH (spiked with 5% $NH_4OH$) revealed almost complete conversion at this time. Ethanol (2 mL) was added and the flask was transferred to a rotary evaporator and concentrated at high vac. The resulting oil was re-dissolved in ethanol and concentrated again. The dried residue was dissolved in methylene chloride (~4 mL) and loaded on to a pre-equilibrated silica gel column (60 mL silica, 30% Hexanes in EtOAc/2% MeOH (spiked with 5% $NH_4OH$)) and eluted with increasingly polar solvent mixtures (2-8% MeOH, 2% increments, 100 mL/increment). Fractions containing the desired material were pooled and concentrated to give the desired compound (0.255 g, 71%).

$^1$H NMR (400 MHz, $CD_3OD$) δ (ppm)=8.11 (d, J=7.4 Hz, 2H), 7.71-7.48 (m, 3H), 7.48-7.31 (m, 4H), 7.25 (m, 1H), 6.09 (m, 1H), 5.63 (d, J=7.1 Hz, 1H), 5.40-5.16 (m, 3H), 4.99 (d, J=8.1 Hz, 1H), 4.28-4.13 (m, 3H), 3.86 (br d, J=6.8 Hz, 1H), 3.64 (m, 4H), 2.67-2.10 (m, 14H), 1.99-1.72 (m, 7H), 1.68 (s, 3H), 1.40 (s, 9H), 1.15 (s, 3H), 1.11 (s, 3H).

The material was recrystallized from EtOAc/Hexanes and used for biological and solubility testing. After re-crystallization, HPLC/MS (m/z); 963.2 (m+H) 99.8% area by UV.

The same general procedure was used to generate the following analogs:

TD2: N-methyl-piperazinyl acetic acid ester

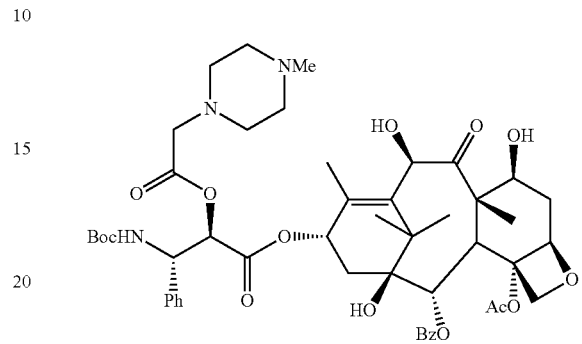

$^1$H NMR (400 MHz, $CD_3OD$) δ (ppm)=8.11 (d, J=7.4 Hz, 2H), 7.66 (t, J=7.4 Hz, 1H), 7.57 (t, J=7.7 Hz, 2H), 7.41 (m, 4H), 7.25 (m, 1H), 6.08 (m, 1H), 5.62 (d, J=7.1 Hz, 1H), 5.42 (d, 2H), 5.27 (s, 1H), 4.99 (d, J=8.1 Hz, 1H), 4.29-4.13 (m, 3H), 3.85 (br d, J=6.8 Hz, 1H), 3.42-3.33 (m, 3H), 2.71-2.27 (m, 16H), 2.03 (q, 1H), 1.92 (s, 3H), 1.89-1.79 (m, 1H), 1.68 (s, 3H), 1.39 (s, 9H), 1.15 (s, 3H), 1.11 (s, 3H). HPLC/MS (m/z); 949.4 (m+H) 95% area by UV.

TD3: N-methyl-piperazinyl pentanoic acid ester

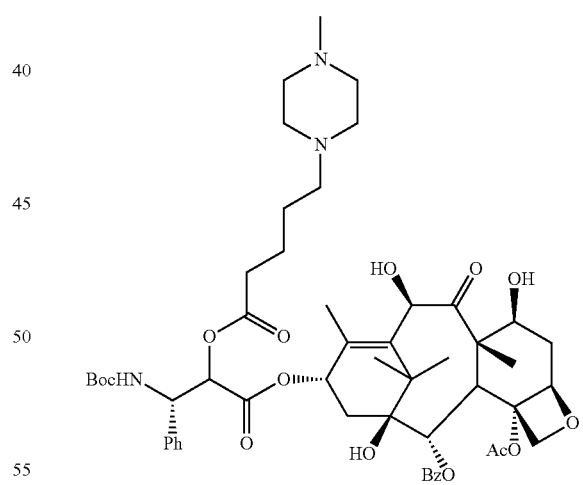

$^1$H NMR (400 MHz, $CD_3OD$) δ (ppm)=8.11 (d, J=7.4 Hz, 2H), 7.66 (t, J=7.4 Hz, 1H), 7.57 (t, J=7.7 Hz, 2H), 7.41 (m, 4H), 7.25 (m, 1H), 6.08 (m, 1H), 5.62 (d, J=7.1 Hz, 1H), 5.37-5.18 (m, 3H), 4.99 (d, J=8.1 Hz, 1H), 4.29-4.13 (m, 3H), 3.85 (d, J=6.8 Hz, 1H 1H), 3.63-3.48 (m, 5H), 2.80-2.27 (m, 24H), 2.27-2.13 (m, 1H), 2.03 (q, 2H), 1.97-1.54 (m, 19H), 1.57-1.49 (br m, H), 1.39 (s, 9H), 1.15 (s, 3H), 1.11 (s, 3H). HPLC/MS (m/z); 990.6 (m+H) 96% area by UV.

TD5: Morpholino acetic acid ester

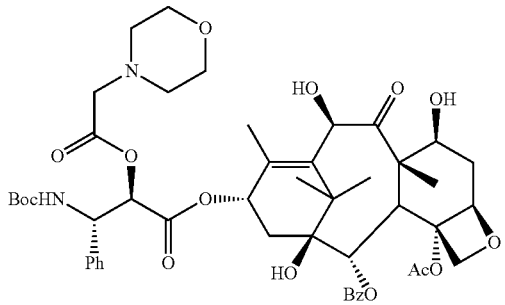

¹H NMR (400 MHz, CD$_3$OD) δ (ppm)=8.12 (d, J=7.4 Hz, 2H), 7.64 (t, J=7.4 Hz, 1H), 7.59-7.50 (m, 2H), 7.44-7.34 (m, 4H), 7.32-7.20 (m, 1H), 6.16 (m, 1H), 5.64 (d, J=7.1 Hz, 1H), 5.42 (br d, 2H), 5.27 (s, 1H), 5.01 (d, J=8.1 Hz, 1H), 4.27-4.15 (m, 3H), 3.89 (d, J=6.8 Hz, 1H), 3.71-3.58 (m, 4H), 3.38 (d, 1H), 2.54-2.26 (m, 9H), 2.12-2.01 (m, 1H), 1.92 (s, 3H), 1.87-1.76 (m, 1H), 1.69 (s, 3H),), 1.39 (s, 9H), 1.15 (s, 3H), 1.11 (s, 3H). HPLC/MS (m/z); 936.1 (m+H) 98% area by UV.

TD6: Morpholino propionic acid ester

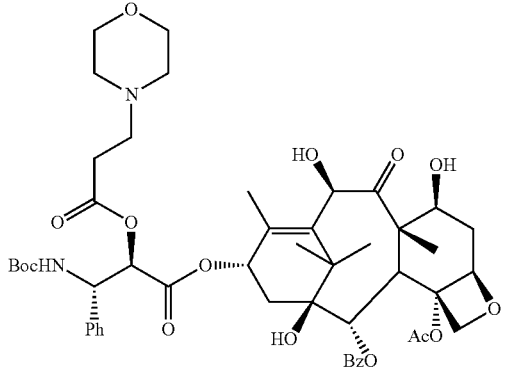

¹H NMR (400 MHz, CD$_3$OD) δ (ppm)=8.11 (d, J=7.4 Hz, 2H), 7.66 (t, J=7.4 Hz, 1H), 7.61-7.50 (m, 2H), 7.45-7.33 (m, 4H), 7.30-7.20 (m, 1H), 6.09 (m, 1H), 5.63 (d, J=7.1 Hz, 1H), 5.39-5.16 (m, 3H), 5.00 (d, J=8.1 Hz, 1H), 4.27-4.13 (m, 3H), 3.86 (d, J=6.8 Hz, 1H), 3.70-3.54 (m, 4H), 2.72-2.56 (m, 4H), 2.52-2.29 (m, 8H), 2.29-2.14 (m, 1H), 1.99-1.86 (m, 4H), 1.86-1.75 (m, 2H), 1.68 (m, 13H), 1.39 (s, 9H), 1.15 (s, 3H), 1.11 (s, 3H). HPLC/MS (m/z); 950.9 (m+H) 94% area by UV.

TD8: Piperidinyl acetic acid ester

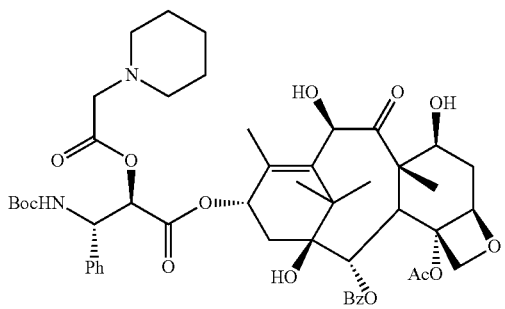

¹H NMR (400 MHz, CD$_3$OD) δ (ppm)=8.16 (d, J=7.4 Hz, 2H), 7.63 (t, J=7.4 Hz, 1H), 7.54 (t, J=7.7 Hz, 2H), 7.44-7.34 (m, 4H), 7.27 (m, 1H), 6.17 (m, 1H), 5.65 (d, J=7.1 Hz, 1H), 5.49-5.38 (m, 2H), 5.28 (s, 1H), 5.01 (d, J=8.1 Hz, 1H), 4.24-4.15 (m, 3H), 3.90 (d, J=6.8 Hz, 1H), 3.36-3.32 (m, 1H), 3.19-3.11 (m, 1H), 2.57-2.25 (m, 9H), 2.16-2.06 (m, 1H), 1.92 (s, 3H), 1.87-1.76 (m, 1H), 1.69 (s, 3H), 1.65-1.50 (m, 4H), 1.40-1.22 (m, 11H), 1.15 (s, 3H), 1.11 (s, 3H). HPLC/MS (m/z); 933.8 (m+H) 94% area by UV.

TD7: Piperidinyl butanoic acid ester

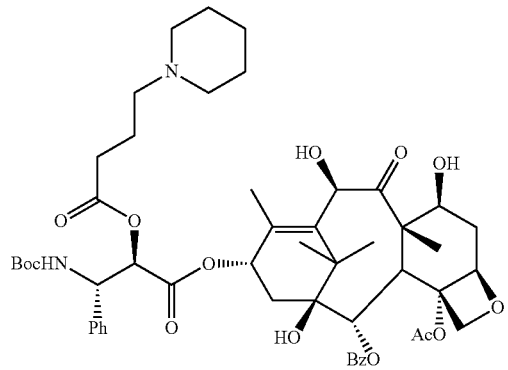

¹H NMR (400 MHz, CD$_3$OD) δ (ppm)=8.11 (d, J=7.4 Hz, 2H), 7.65 (t, J=7.4 Hz, 1H), 7.56 (t, J=7.7 Hz, 2H), 7.44-7.33 (m, 4H), 7.29-7.20 (m, 1H), 6.09 (m, 1H), 5.63 (d, J=7.1 Hz, 1H), 5.36-5.30 (m, 1H), 5.29-5.26 (m, 2H), 5.03-4.95 (m, 1H), 4.27-4.14 (m, 3H), 3.86 (d, J=6.8 Hz, 1H), 2.59-2.16 (m, 15H), 2.01-1.75 (m, 8H), 1.68 (s, 3H), 1.64-1.54 (m, 5H), 1.47 (m, 3H), 1.40 (s, 9H), 1.15 (s, 3H), 1.11 (s, 3H). HPLC/MS (m/z); 962.5 (m+H) 94% area by UV.

TD9: Piperidinyl pentanoic acid ester

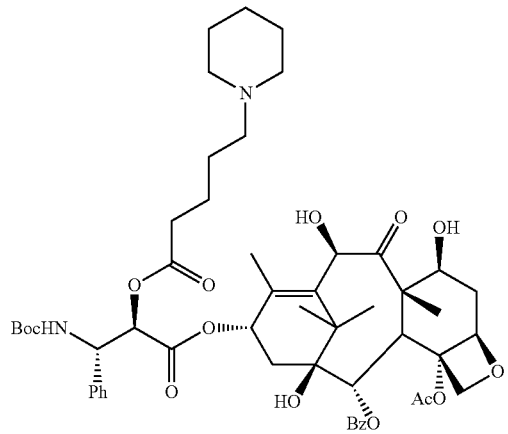

¹H NMR (400 MHz, CD$_3$OD) δ (ppm)=8.11 (d, J=7.4 Hz, 2H), 7.66 (, J=7.4 Hz, 1H), 7.57 (t, J=7.7 Hz, 2H), 7.45-7.33 (m, 4H), 7.25 (br s, 1H), 6.08 (m, 1H), 5.62 (d, J=7.1 Hz, 1H), 5.31 (m, 1H), 5.28-5.18 (m, 2H), 4.99 (d, J=8.1 Hz, 1H), 4.27-4.15 (m, 3H), 3.85 (d, J=6.8 Hz, 1H), 2.51-2.18 (m, 17H), 1.97-1.75 (m, 5H), 1.75-1.46 (m, 20H), 1.43-1.38 (m, 10H), 1.15 (s, 3H), 1.11 (s, 3H). HPLC/MS (m/z); 976.2 (m+H) 96% area by UV.

7-OH acylation (general procedure)
Protection: GCW00006-09

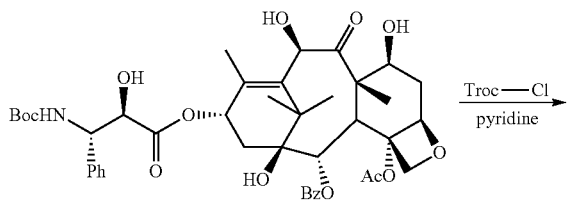

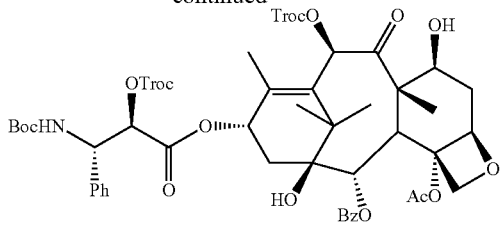

To a stirred, cooled (−45° C.) solution of docetaxel (0.746 g, 0.923 mmol) in methylene chloride (20 mL) and pyridine (1.6 mL) was added trichloroethyl chloroformate (Troc-Cl, 0.137 mL, 1.01 mmol, 1.1 equiv) in a dropwise fashion. The reaction was allowed to stir for 1 h at reduced temperature, and a second, equal portion of Troc-Cl (0.137 mL, 1.01 mmol, 1.1 equiv) was added in a dropwise fashion. The reaction was allowed to gradually warm to room temperature with stirring over the course of the next 16 h. At that time TLC analysis (30% EtOAc in Hexanes) indicated a minimal amount of remaining starting material and the formation of three new spots presumed to be the 2',10-di-Troc, the 2',7-di-Troc and the 2',7,10-tri-Troc protected compounds. The reaction was diluted with a minimal amount of ethanol and concentrated to dryness on a high-vac equipped rotovap. The residue was then dissolved in a minimal amount of $CH_2Cl_2$ and loaded on to a pre-equilibrated column of silica gel (3 cm×20 cm, 20% EtOAc in hexanes). Careful elution of the desired products from the column using increasingly polar solvent mixtures (20-60% EtOAc in hexanes, 100 mL volumes, 5% increments), and collection and concentration of the clean fractions yielded the desired isomer as an amorphous white solid (0.433 g, 40%).

$^1$H NMR (400 MHz, $CDCl_3$) δ (ppm)=8.11 (d, 2H), 7.61 (t, 1H), 7.51 (t, 2H), 7.45-7.33 (m, 5H), 6.29 (m, 1H), 6.16 (s, 1H), 5.69 (d, 1H), 5.59-5.56 (m, 1H), 5.55-5.42 (m, 2H), 5.35 (br s, 1H), 4.96 (br d, 1H), 4.89 (d, 1H), 4.76 (q, 2H), 4.69 (d, 1H), 4.41-4.37 (m, 1H), 4.32 (d, 1H), 4.18 (d, 1H), 3.96-3.91 (m, 3H), 3.78 (d, 1H), 2.61-2.53 (m, 1H), 2.43 (s, 3H), 2.39-2.18 (m, 3H), 2.11-1.76 (m, 11H), 1.73 (br s, 1H), 1.69 (s, 3H), 1.32 (s, 9H), 1.28-1.17 (m, 6H).

The same general procedure was used to generate the following analogs:

Esterification: GCW00006-10

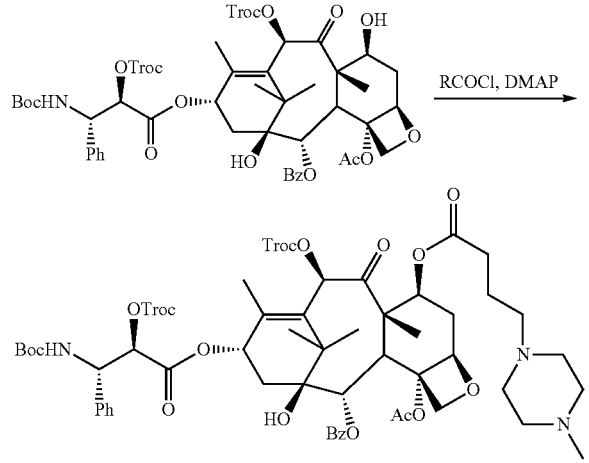

To a round bottom flask containing 4-(4-methylpiperazin-1-yl)butanoic acid hydrochloride (0.58 g, 2.61 mmol) and a magnetic stir bar was added thionyl chloride (15 mL). The resulting solution was heated to reflux for 1.5 h, cooled to room temperature, concentrated on a rotary evaporator, suspended in anhydrous toluene (10 mL), concentrated on a rotary evaporator again to yield a white solid and dried on a high vacuum line for 3 h to a steady weight that gave off no odor of thionyl chloride or hydrochloric acid.

To a solution of GCW00006-09 (0.433 g, 0.375 mmol) in methylene chloride (Dri-Solve, 8 mL), containing a magnetic stirrer was added N,N-dimethylamino-pyridine (DMAP, 0.229 g, 5 equiv). The solution was cooled to 0° C. and the above described amino acyl chloride hydrochloride (0.100 g, 1.1 equiv) was added in portions over the course of a couple of minutes. The reaction was followed based on TLC analysis for the consumption of starting material as the DMAP tended to co-elute with the mono-amino acylated product. After 2 h, some remaining starting material was still observed by TLC and an additional portion of the amino-acyl chloride hydrochloride was added (0.05 g, 0.55 equiv). After an additional hour with stirring at room temperature, TLC indicated almost complete consumption of the starting material. The reaction was concentrated on a rotary evaporator to give an oil that was dissolved in a minimal amount of $CH_2Cl_2$ (5 mL) and loaded on to a pre-equilibrated column of silica (3 cm×20 cm, 4:1 $CH_2Cl_2$/Hexanes) and subjected to flash chromatography (4:1 $CH_2Cl_2$/Hexanes with 1-10% MeOH (containing 5% $NH_4OH$). Fractions containing the desired material were collected and concentrated to give a colorless glass (0.284 g, 57%).

$^1$H NMR (400 MHz, $CD_3OD$) δ (ppm)=8.11 (d, J=7.5 Hz, 2H), 7.61 (t, J=7.7 Hz, 1H), 7.51 (t, J=7.7 Hz, 2H), 7.43-7.39 (m, 4H), 7.28-7.26 (m, 1H), 6.13-6.05 (m, 2H), 5.64 (d, J=6.8 Hz, 1H), 5.60-5.56 (m, 1H), 5.55-5.42 (m, 2H), 5.36-5.34 (m, 1H), 4.99 (d, J=6.8 Hz, 1H), 4.92 (d, J=11.2 Hz, 1H), 4.83 (d, J=11.2 Hz, 1H), 4.19 (dd, J=8.2, 19.0 Hz, 1H), 3.85 (d, J=6.3 Hz, 1H), 2.67-2.22 (m, 20H), 2.05-1.89 (m, 4H), 1.82-1.71 (m, 6H), 1.40 (s, 9H), 1.15 (s, 3H), 1.11 (s, 3H). HPLC/MS (m/z); 1325.7 (m+H) 83% area by UV (contaminated with 10% methyl carbonate (m/z=1210.4)).

Deprotection to form TD10: 7-O—(N-methyl-piperazinyl butanoic acid ester)

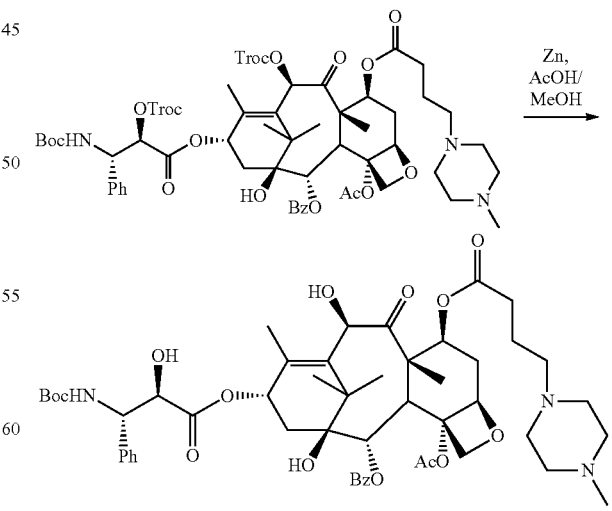

To a vigorously stirred solution of GCW00006-10 (0.276 g, 0.2 mmol) in methanol and acetic acid (50 mL, 10% AcOH) was added elemental zinc dust (~0.1 g). The reaction was monitored by TLC and within 1 h all of the starting material had been consumed and converted to a singular lower running spot (10% MeOH (w 5% NH₄OH) in CH₂Cl₂). The reaction was diluted with MeOH (50 mL) and filtered on a filter paper lined Buchner funnel. The resulting solution was concentrated to dryness on a rotary evaporator to give a stiff syrup that was dissolved in CH₂Cl₂ (5 mL) and loaded on to a pre-equilibrated column of silica gel (3 cm×15 cm, 2% MeOH (w 5% NH₄OH) in CH₂Cl₂) and eluted with increasing polar solvent (2-10% MeOH (w 5% NH₄OH) in CH₂Cl₂, 2% increments, 150 mL/increment). Fractions containing the clean material, as determined by TLC were collected and concentrated to give a white solid (0.0764, 39%). HPLC/MS indicates minor contamination (~10%) containing a methyl carbonate substituent at undetermined location on the parent compound.

(m/z=1035.3) $^1$H NMR (400 MHz, CD$_3$OD) δ (ppm)=8.12 (d, J=7.5 Hz, 2H), 7.68 (t, J=7.7 Hz, 1H), 7.58 (t, J=7.7 Hz, 2H), 7.43-7.39 (m, 4H), 7.28-7.26 (m, 1H), 6.13-6.05 (m, 2H), 5.67 (d, J=6.8 Hz, 1H), 5.60-5.56 (m, 1H), 5.38 (s, 1H), 5.14 (br s, 1H), 5.01 (d, J=6.8 Hz, 1H), 4.52 (br s, 1H), 3.98 (d, J=6.3 Hz, 1H), 2.67-2.22 (m, 18H), 2.10-1.71 (m, 10H), 1.40 (s, 9H), 1.15 (s, 3H), 1.12 (s, 3H). $^{13}$C NMR (100 MHz, CD$_3$OD) δ (ppm)=209.32, 173.04, 172.30, 170.61, 166.25, 156.36, 145.92, 139.27, 138.27, 136.40, 133.20, 129.98, 129.78, 128.31, 128.19, 127.38, 126.83, 83.70, 80.46, 79.32, 77.75, 76.12, 74.86, 74.24, 74.03, 71.68, 71.00, 57.16, 57.00, 56.14, 54.18, 52.14, 46.06, 44.51, 42.98, 37.97, 35.41, 32.98, 31.33, 31.19, 27.30, 25.39, 21.69, 21.43, 21.28, 20.17. HPLC/MS (m/z); 977.1 (m+H) 85% area by UV.

Example 3

Water-Soluble Prednisone Derivatives

N-methyl-piperazinyl-butanoic acid ester

Linker Synthesis

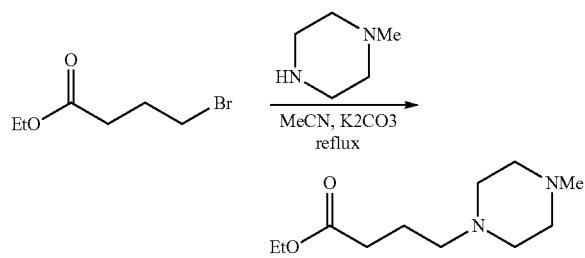

A mixture of ethyl 4-bromobutanoate (5.75 g, 29.5 mmol; Aldrich No.167118) and 1-methylpiperazine (3.55 mL, 32.0 mmol; Aldrich No. 130001) and anhydrous K₂CO₃ (4.5 g, 32.5 mmol; Fisher No. P208) in acetonitrile (MeCN, 150 mL) was refluxed for 18 h before concentrated in vacuo. The organic layer was then separated and the aqueous layer was extracted with dichloromethane (DCM, 3×150 mL). The combined organic extracts were washed with water (150 mL), dried (Na₂SO₄), and concentrated in vacuo to give ethyl 4-(4-methylpiperzin-1-yl)butanoate (6.01 g, 96%) as a yellow oil.

$^1$H NMR (CDCl$_3$): 4.03 (q, 2H, J=7.15 Hz), 2.29-2.44 (m, 7H), 2.21-2.28 (m, 5H), 2.18 (s, 3H), 1.67-1.75 (m, 2H), 1.18 (t, 3H, J=7.14 Hz)

$^{13}$C NMR (CDCl$_3$): 174.4, 61.1, 58.5, 56.1, 54.0, 47.0, 33.2, 23.1, 15.2

ESI-MS: 215.1 [M+H]$^+$; 237.2 [M+Na]$^+$

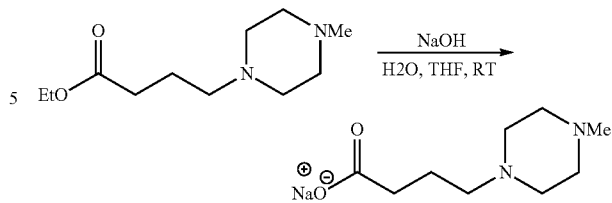

To a solution of ethyl 4-4(methylpiperazin-1-yl)butanoate (6.01 g, 28.1 mmol) in tetrahydrofuran (THF, 150 mL) was added a solution of NaOH (1.20 g, 30 mmol) in water (150 mL). The mixture was stirred at RT for 18 h before concentrated to dryness to give sodium 4-(4-methylpiperazin-1-yl) butanoate (6.06 g, quant.) as a white powder.

$^{13}$C NMR (MeOH-d$_4$): 181.0, 58.2, 54.2, 52.4, 44.8, 35.7, 23.2

ESI-MS: 187.3 [M+H]$^+$; 209.2 [M+Na]$^+$

Esterification

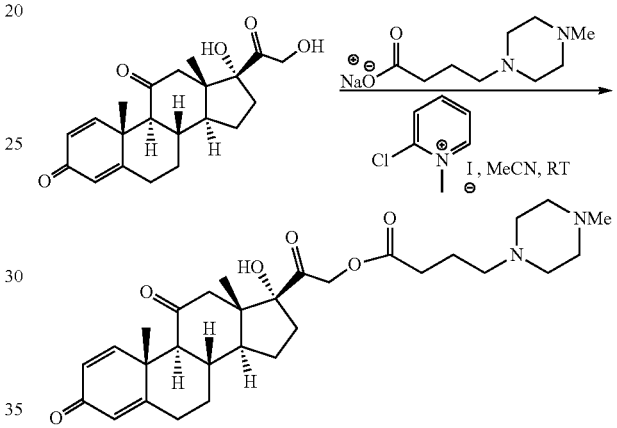

To a suspension of sodium 4-(4-methylpiperazin-1-yl)butanoate (128 mg, 0.615 mmol) and prednisone (200 mg, 0.559 mmol) in acetonitrile (MeCN, 10 mL) was added 2-chloro-1-methyl-pyridinium iodide (235 mg, 0.922 mmol; Aldrich No. 198005). The resulting suspension was stirred at RT for 18 h before quenching with water (30 mL). The product was then extracted with ethylacetate (EtOAc, 4×20 mL), washed with sat. aq. NaHCO₃ (3×20 mL) and brine (20 mL), dried (Na₂SO₄), and concentrated in vacuo. Further purification was performed on a silica gel column (solvent: 1% NH₄OH, 10% MeOH, 89% dichloromethane) to give the free base of the derivatized prednisone (108 mg, 36%) as a white solid.

$^1$H NMR (CDCl$_3$): 7.64 (d, 1H, J=10.40), 6.08 (dd, 1H, J=10.40, 1.90), 6.06 (t, 1H, J=2.90), 5.06 (ABq, 2H, J=94.78, 17.81), 2.85 (d, 1H, J=12.32), 2.65 (t, 1H, J=12.57), 2.56-1.06 (CM, 32H), 2.16 (s, 3H), 1.34 (s, 3H), 0.57 (s, 3H)

$^{13}$C NMR (CDCl$_3$): 209.17, 205.05, 186.61, 172.86, 167.44, 155.93, 127.29, 124.31, 88.18, 67.78, 60.05, 57.30, 54.92, 52.73, 51.28, 49.97, 49.56, 45.89, 42.47, 36.00, 34.47, 33.64, 32.23, 31.63, 23.21, 21.93, 18.68, 15.30

MS: 527.4 [M+H]$^+$

N-methyl-piperazinyl acetic acid ester

Linker synthesis

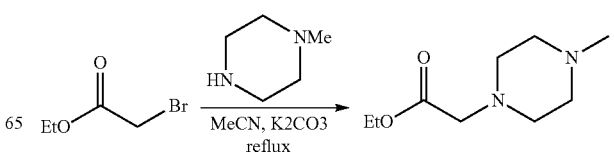

A mixture of ethyl 2-bromoacetate (4.93 g, 29.5 mmol), 1-methylpiperazine (3.55 mL, 32.0 mmol; Aldrich No. 130001), and $K_2CO_3$ (4.5 g, 32.5 mmol; Fisher No. P208) in $CH_3CN$ (150 mL) was refluxed for 18 h before concentrated in vacuo. The organic layer was then separated and the aqueous layer was extracted with DCM (3×150 mL). The combined organic extracts were washed with water (150 mL), dried ($Na_2SO_4$), and concentrated in vacuo to give ethyl 4-(4-methylpiperzin-1-yl)acetate (5.26 g, 96%) as a yellow oil.

$^1$H NMR ($CDCl_3$): 3.76 (q, 2H, J=7.14 Hz), 2.76 (s, 3H), 2.30-1.90 (br, 4H), 0.85 (t, 3H, J=7.14 Hz)

$^{13}$C NMR ($CDCl_3$): 169.55, 59.90, 58.93, 54.44, 53.26, 52.47, 45.59, 13.84

ESI-MS: 187 [M+H]$^+$

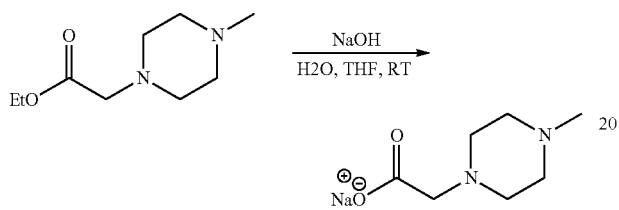

To a solution of ethyl 2-4(methylpiperazin-1-yl)acetate (5.26 g, 28.3 mmol) in THF (150 mL) was added a solution of NaOH (1.20 g, 30 mmol) in water (150 mL). The mixture was stirred at RT for 18 h before concentrated to dryness to give sodium 4-(4-methylpiperazin-1-yl)acetate (5.24 g, quant.) as a white powder.

$^{13}$C NMR (MeOH-$d_4$): 169.55, 59.90, 58.93, 54.44, 52.47, 45.59

ESI-MS: 187.3 [M+H]$^+$; 209.2 [M+Na]$^+$

Esterification

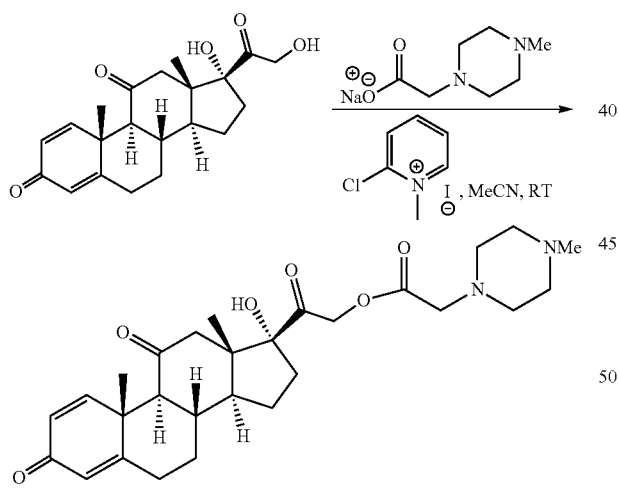

To a suspension of sodium 2-(4-methylpiperazin-1-yl)acetate (111 mg, 0.615 mmol) and prednisone (200 mg, 0.559 mmol) in $CH_3CN$ (10 mL) was added 2-chloro-1-methyl-pyridinium iodide (235 mg, 0.922 mmol; Aldrich No. 198005). The resulting suspension was stirred at RT for 18 h before quenching with water (30 mL). The product was then extracted with EtOAc (4×20 mL), washed with sat. aq. $NaHCO_3$ (3×20 mL) and brine (20 mL), dried ($Na_2SO_4$), and concentrated in vacuo. Further purification was performed on a silica column (solvent: 1% $NH_4OH$, 10% MeOH, 89% DCM) to give the derivatized prednisone (154 mg, 38%) as a white solid.

$^1$H NMR ($CDCl_3$): 7.71 (d, 1H, J=10.28), 6.19 (dd, 1H, J=10.24, 1.96), 6.07 (t, 1H, J=1.93), 4.93 (ABq, 2H, J=124.45, 17.56), 3.33 (s, 1H), 2.89 (d, 1H, J=13.36), 2.84-1.17 (CM, 32H), 2.27 (s, 3H), 1.43 (s, 3H), 0.66 (s, 3H)

$^{13}$C NMR ($CDCl_3$): 208.88, 204.58, 186.58, 169.85, 167.06, 155.68, 127.49, 124.50, 88.38, 67.96, 60.22, 59.01, 54.73, 53.42, 52.71, 51.43, 49.67, 49.56, 46.00, 42.45, 36.06, 34.79, 33.73, 32.25, 23.26, 18.75, 15.45

MS: 449.3 [M+H]$^+$

Example 4

Lipophilic Prednisone Derivatives

Internal Linoleyl Linkers 1-(tent-butyldimethylsilyloxy)-3-(dimethylamino)propan-2-ol A dry dichloromethane (10 mL) solution of 3-(dimethylamino)-1,2-propanediol (98%, 1.00 g, 8.39 mmol, 1.0 equiv) and imidazole (0.57 g, 8.39 mmol, 1.0 equiv) was stirred at 0° C. under argon for 15 minutes. Solid tert-butyldimethylsilyl chloride (1.26 g, 8.39 mmol, 1.0 equiv) was added to the mixture and the resultant was stirred for 2 hours at 0° C. The mixture was then diluted with 20 mL of dichloromethane and poured into deionized water (15 mL). The organic layer was separated and the aqueous layer was extracted with two additional portions of dichloromethane (20 mL). The combined organic extracts were dried ($MgSO_4$), filtered and concentrated to afford crude 1-(tent-butyldimethylsilyloxy)-3-(dimethylamino)propan-2-ol, a thick clear oil, which was used without further purification.

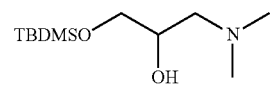

$^1$H NMR: 3.72-3.80 (m, 1H), 3.63 (d, 2H, J=5.19), 2.34-2.46 (m, 2H), 2.33 (s, 6H), 0.91 (2, 9H), 0.08 (s, 6H)

3-(tert-butyldimethylsilyloxy)-N,N-dimethyl-2-((9Z,12Z)-octadeca-9,12-dienyloxy)propan-1-amine A toluene (10 mL) solution of crude 1-(tert-butyldimethylsilyloxy)-3-(dimethylamino)propan-2-ol (1.0 g, 4.29 mmol, 1.0 equiv) was carefully added dropwise to a toluene suspension (5 mL) of NaH (60%, 0.17 g, 4.29 mmol, 1.0 equiv) at 0° C. under argon and the resultant was stirred for 15 minutes. A toluene solution (5 mL) of linoleyl methanesulfonate (1.47 g, 4.29 mmol, 1.0 equiv) was added dropwise to the stirring mixture and the reaction was then stirred for 18 hours at 90° C. The mixture was then cooled to room temperature and quenched by the slow addition of ethanol (10 mL). The mixture was then concentrated and the residue was taken up with deionized water (15 mL) and extracted three times with EtOAc (20 mL). The combined organic extracts were washed with deionized water (15 mL), dried ($MgSO_4$), filtered, and concentrated. Chromatographic purification of the residue (0-5% MeOH in chloroform) yielded 109 mg (53% yield) of 3-(tert-butyldimethylsilyloxy)-N,N-dimethyl-2-((9Z,12Z)-octadeca-9,12-dienyloxy)propan-1-amine, a thick clear oil.

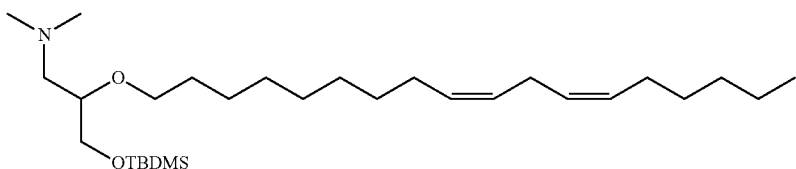 [SMILES: CCCCC/C=C\C/C=C\CCCCCCCCOC(CO[Si](C)(C)C(C)(C)C)CN(C)C]

¹H NMR: 5.28-5.42 (m, 4H), 3.47-3.62 (m, 4H), 3.37-3.42 (m, 1H), 2.77 (t, 2H, J=5.94), 2.28-2.47 (m, 2H), 2.25 (s, 6H), 2.01-2.09 (m, 5H), 1.50-1.58 (m, 2H), 1.30 (br, 18H), 0.09 (s, 9H), 0.06 (s, 6H).
¹³C NMR: 130.22, 130.01, 127.98, 127.88, 70.16, 63.07, 37.35, 32.79, 31.52, 29.59, 29.49, 29.39, 29.34, 29.32, 29.23, 29.15, 29.11, 29.00, 27.19, 25.72, 25.62, 25.40, 22.57, 14.07.

3-(dimethylamino)-2-((9Z,12Z)-octadeca-9,12-dienyloxy)propan-1-ol

TBAF (1.0 M in THF, 0.5 mL, 0.50 mmol, 1.2 equiv) was added in one portion to a dry THF (100 μL) solution of 3-(tert-butyldimethylsilyloxy)-N,N-dimethyl-2-((9Z,12Z)-octadeca-9,12-dienyloxy)propan-1-amine (0.2 g, 0.42 mmol, 1.0 equiv) and the mixture was stirred at room temperature for 2 hours. The mixture was concentrated and the residue was partitioned between EtOAc (15 mL) and aqueous saturated ammonium chloride solution (10 mL). The layers were separated and the aqueous layer was extracted with 2 additional portions of EtOAc (10 mL). The combined extracts were dried (MgSO₄), filtered, and concentrated to give crude 3-(dimethylamino)-2-((9Z,12Z)-octadeca-9,12-dienyloxy)propan-1-ol, a thick, beige oil, which was used without further purification.

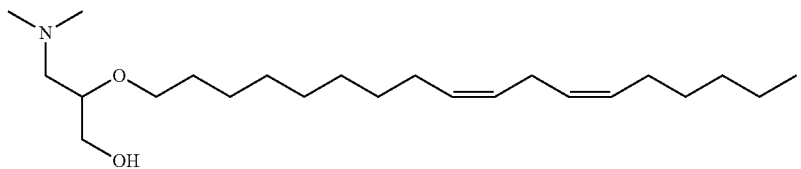 [SMILES: CCCCC/C=C\C/C=C\CCCCCCCCOC(CO)CN(C)C]

¹H NMR: 5.29-5.43 (m, 4H), 3.77-3.82 (m, 1H), 3.65-3.71 (m, 1H), 3.42-3.51 (m, 3H), 2.78 (t, 2H, J=5.97), 2.54-2.57 (m, 2H), 2.30 (s, 6H), 2.02-2.09 (m, 4H), 1.50-1.57 (m, 2H), 1.30 (br, 15H), 0.87-0.92 (m, 4H).

4-(3-(dimethylamino)-2-((9Z, 12Z)-octadeca-9,12-dienyloxy)propoxy)-4-oxobutanoic Acid Succinic anhydride (0.60 g, 5.99 mmol, 1.1 equiv) was added in one portion to a dry THF (11 mL) solution of 3-(dimethylamino)-2-((9Z,12Z)-octadeca-9,12-dienyloxy)propan-1-ol (2.0 g, 5.45 mmol, 1.0 equiv) and the resultant was refluxed for 18 hours under argon. The mixture was concentrated and then dissolved in EtOAc (10 mL) and poured into deionized water (20 mL). The layers were separated and the aqueous layer was extracted with two additional portions of EtOAc (25 mL). The combined organic extracts were dried (MgSO₄), filtered and concentrated to provide crude 4-(3-(dimethylamino)-2-((9Z,12Z)-octadeca-9,12-dienyloxy)propoxy)-4-oxobutanoic acid, a thick yellow oil, which was used without further purification.

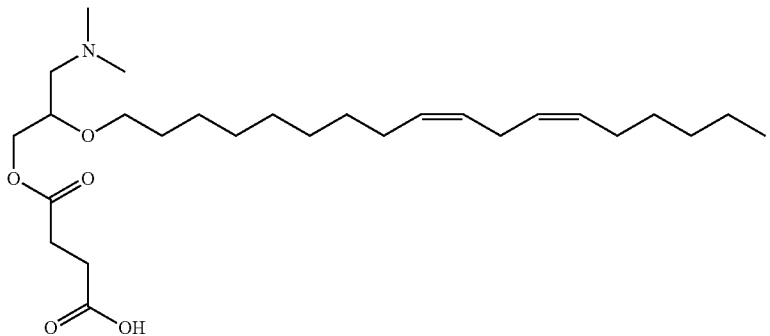 [SMILES: CCCCC/C=C\C/C=C\CCCCCCCCOC(COC(=O)CCC(=O)O)CN(C)C]

¹H NMR: 5.29-5.43 (m, 4H), 4.28 (d, 1H, J=11.25), 3.92-3.98 (m, 1H), 3.84 (br, 1H), 3.60-3.67 (m, 1H), 3.43-3.50 (m, 1H), 3.11-3.15 (d, 1H, J=12.45), 2.75-2.79 (m, 2H), 2.67 (s, 6H), 2.53-2.65 (m, 5H), 2.01-2.08 (m, 4H), 1.53-1.57 (m, 2H), 1.29-1.30 (br, 18H), 0.87-0.91 (m, 3H).

¹³C NMR: 176.63, 172.55, 130.09, 129.98, 127.91, 127.84, 73.90, 69.90, 67.85, 62.54, 59.08, 44.11, 31.44, 30.53, 29.97, 29.93, 29.58, 29.42, 29.36, 29.27, 29.20, 27.14, 27.11, 26.04, 25.55, 22.50, 14.01.

External Linoleyl Linkers 1-(dimethylamino)-4-((9Z,12Z)-octadeca-9,12-dienyloxy)butan-2-ol A toluene (10 mL) solution of 3-(dimethylamino)-1,2-propanediol (98%, 1.00 g, 8.39 mmol, 1.0 equiv)) was carefully added dropwise to a toluene suspension (5 mL) of NaH (60%, 0.34 g, 8.39 mmol, 1.0 equiv) at 0° C. under argon and the resultant was stirred for 15 minutes. A toluene solution (5 mL) of linoleyl methanesulfonate (2.87 g, 8.39 mmol, 1.0 equiv) was added dropwise to the stirring mixture and the reaction was then stirred for 18 hours at 90° C. The mixture was then cooled to room temperature and quenched by the slow addition of ethanol (10 mL). The mixture was concentrated and the residue was taken up with deionized water (20 mL) and extracted three times with EtOAc (30 mL). The combined organic extracts were washed with deionized water (20 mL), dried (MgSO₄), filtered, and concentrated. Chromatographic purification of the residue (0-5% MeOH in chloroform) provided 1-(dimethylamino)-4-((9Z,12Z)-octadeca-9,12-dienyloxy)butan-2-ol, a thick, clear oil.

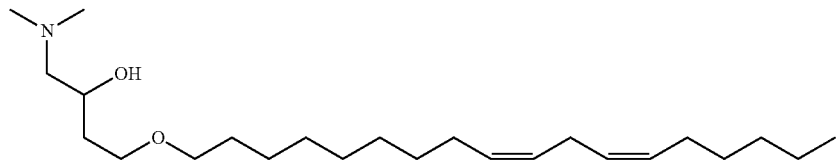 [SMILES: CCCCC/C=C\C/C=C\CCCCCCCCOCCC(O)CN(C)C]

4-(1-(dimethylamino)-4-((9Z,12Z)-octadeca-9,12-dienyloxy)butan-2-yloxy)-4-oxobutanoic Acid Succinic anhydride (0.60 g, 5.99 mmol, 1.1 equiv) was added in one portion to a dry THF (11 mL) solution of 1-(dimethylamino)-4-((9Z,12Z)-octadeca-9,12-dienyloxy)butan-2-ol (2.0 g, 5.45 mmol, 1.0 equiv) and the resultant was refluxed for 18 hours under argon. The mixture was concentrated and the residue was partitioned between EtOAc (10 mL) and deionized water (20 mL). The layers were separated and the aqueous layer was extracted with two additional portions of EtOAc (25 mL). The combined organic extracts were dried (MgSO₄), filtered and concentrated to provide crude 4-(1-(dimethylamino)-4-((9Z,12Z)-octadeca-9,12-dienyloxy)butan-2-yloxy)-4-oxobutanoic acid, a thick, yellow oil, which was used without further purification.

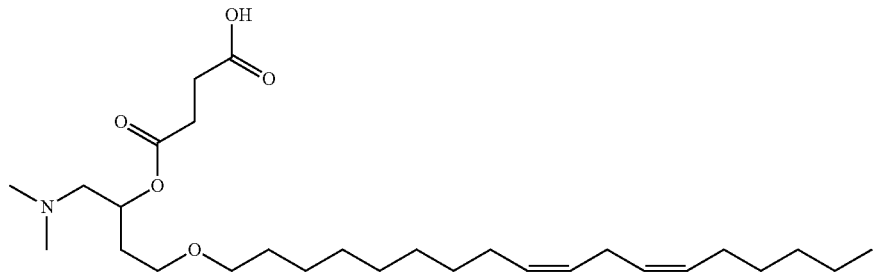 [SMILES: CCCCC/C=C\C/C=C\CCCCCCCCOCCC(CN(C)C)OC(=O)CCC(=O)O]

Esterification of Prednisone with Internal Linker

NEt$_3$ (100 µL, 0.74 mmol, 1.0 equiv) was added dropwise to a dry dichloromethane solution (10 mL) of 4-(3-(dimethylamino)-2-((9Z,12Z)-octadeca-9,12-dienyloxy)propoxy)-4-oxobutanoic acid and the resultant was stirred for 15 minutes under argon at room temperature. PyBOP (0.48 g, 0.93 mmol, 1.25 equiv) was added in one portion and the resultant was stirred for 10 minutes. Prednisone (0.32 g, 0.89 mmol, 1.2 equiv) was added to the mixture and the resultant was stirred at room temperature for 18 hours and then concentrated to provide a thick yellow oil, (90% pure). Purification by flash column chromatography (5-15% MeOH in chloroformand (0-15% MeOH in EtOAc) provided the desired product h. SOCl$_2$ was evaporated, and without further purification the crude acid chloride was dissolved in dry CH$_3$CN (1 mL) under argon atmosphere. The solution was cooled to 0° C., etoposide (6, 50 mg, 0.085 mmoles) dissolved in CH$_3$CN (1 mL) was added dropwise, followed by triethylamine (10 µL). Stirring was continued for 2 h, with monitoring of the reaction by TLC. The solution was then concentrated in vacuo and the crude product was taken up with water and extracted with ethyl acetate (3×10 mL). The combined organic extracts were dried over anhydrous sodium sulfate and concentrated in vacuo. The crude product was purified by silica gel (230-400 mesh) column chromatography (gradient 5-10% MeOH in CH$_2$Cl$_2$) to give 30 mg of desired free base of etoposide derivative 7 as a white solid.

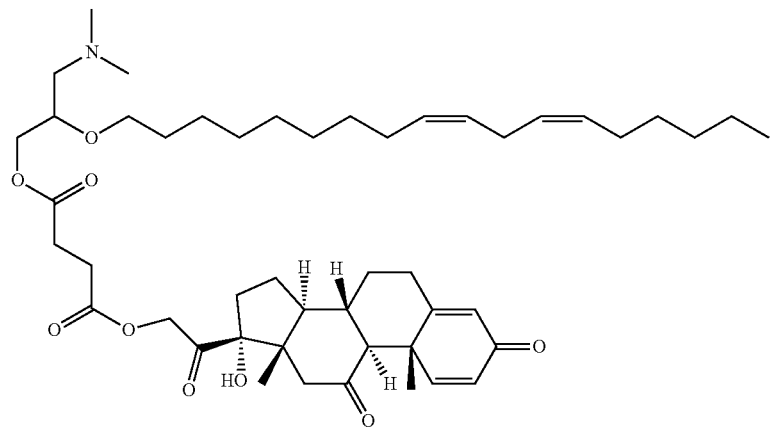 [SMILES: CCCCC/C=C\C/C=C\CCCCCCCCOC(COC(=O)CCC(=O)OCC(=O)[C@@]1(O)CC[C@H]2[C@@H]3CCC4=CC(=O)C=C[C@]4(C)[C@H]3C(=O)C[C@@]21C)CN(C)C]

$^1$H NMR (CDCl$_3$): 7.68 (d, 1H, J=10.23), 6.20 (dd, 1H, J$_1$=10.23, J$_2$=1.86), 6.07 (s, 1H), 5.27-5.42 (m, 4H), 4.80 (dd, 1H, J$_1$=17.70, J$_2$=5.61), 4.09-4.36 (m, 3H), 3.54-3.69 (m, 3H), 3.34 (m, 1H), 3.07-3.22 (m, 1H), 2.94-2.98 (m, 1H), 2.88 (s, 6H), 2.74-2.78 (m, 3H), 2.65-2.68 (m, 3H), 2.37-2.50 (m, 3H), 2.25 (dd, 1H, J$_1$=12.24, J$_1$=2.31), 2.00-2.05 (m, 8H), 1.42 (s, 3H), 1.30 (br, 18H), 0.89 (m, 3H), 0.64 (s, 3H).
MS: 808.8 [M+H]$^+$.

Example 5

Etoposide Derivatives 4-(4-Methylpiperazin-1-yl)butanoic acid dihydrochloride salt (4, 20 mg, 0.09 mmol) was dissolved in SOCl$_2$ (0.5 mL), and stirred under argon atmosphere at room temperature for 3

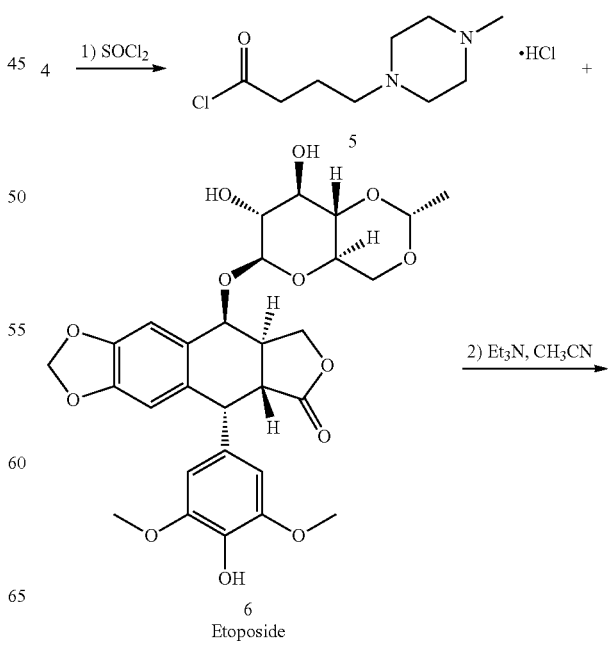

-continued

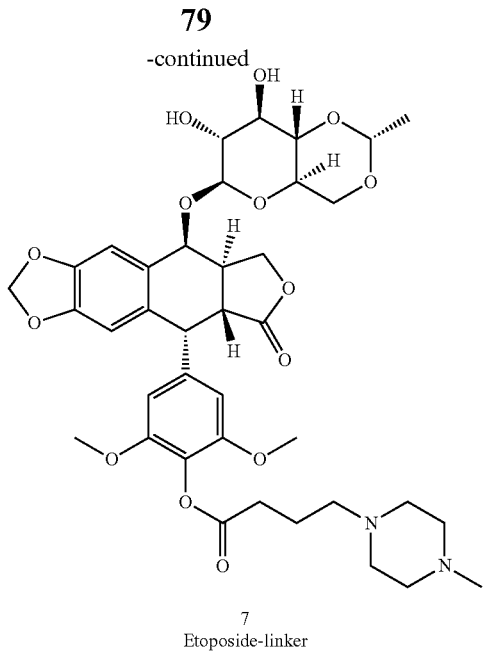

7
Etoposide-linker

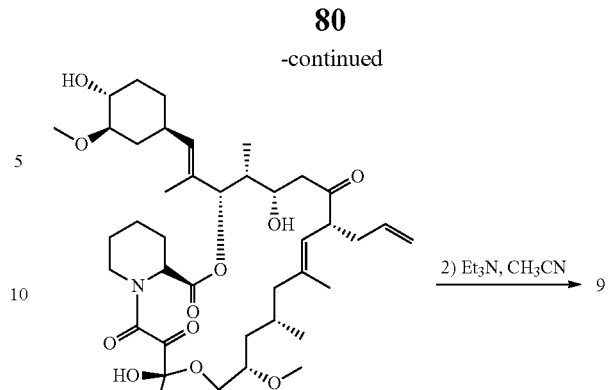
8
Tacrolimus

Expected product:

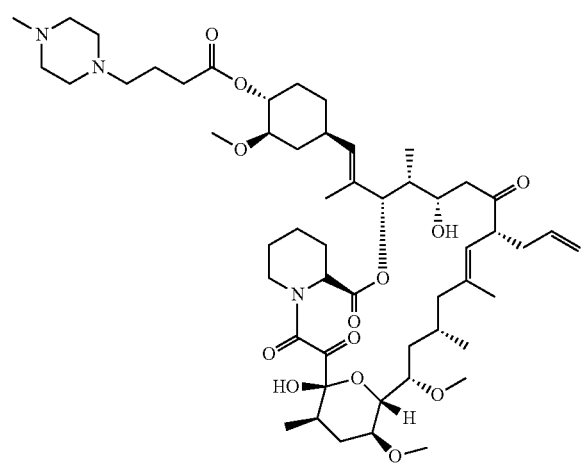
Tacrolimus-liner

¹H NMR (CDCl₃): 6.83 (s, 1H), 6.55 (s, 1H), 6.27 (s, 2H), 5.98-6.00 (d, 2H, J=7.15 Hz), 4.91-4.90 (d, 2H), 4.73-4.78 (q, 1H), 4.63-4.67 (t, 2H), 4.40-4.46 (t, 1H), 4.15-4.26 (m, 2H), 3.75-3.78 (t, 2H), 3.66 (s, 3H), 3.55-3.62 (m), 3.49 (s, 3H), 3.25-3.47 (m), 2.81-2.93 (m), 2.44-2.64 (m), 2.31 (s, 3H), 1.87-1.97 (m), 1.39-1.40 (d, 3H).

ESI-MS: 757.5 [M+H]⁺.

Example 6

Tacrolimus Derivatives 4-(4-Methylpiperazin-1-yl)butanoic acid hydrochloride salt (4, 25 mg, 0.12 mmol) was dissolved in SOCl₂ (0.5 mL), and stirred under argon atmosphere at room temperature for 3 h., then SOCl₂ was evaporated and without further purification compound 5 was dissolved in dry CH₃CN (1 mL) under argon atmosphere. The solution was cooled to 0° C., then tacrolimus (8, 80 mg, 0.1 mmoles) dissolved in CH₃CN (1 mL) was added, followed by triethylamine (10 µL), Stirring was continued for 2 h, then the solution was concentrated in vacuo. The crude product was taken up with water and extracted with ethyl acetate (3×15 mL). The combined organic extracts were dried over anhydrous sodium sulfate and concentrated in vacuo. The crude product was purified by silica gel (230-400 mesh) column chromatography (gradient 5-10% MeOH in CH₂Cl₂) to give 45 mg of desired free base of tacrolimus derivative 9 as a white solid.

¹H NMR (CDCl₃): 5.63 (m, 1H), 5.20-5.32 (m, 2H), 6.27 (s, 2H), 4.98-5.10 (m), 4.80 (d, 1H), 4.63-4.63 (d, 1H), 4.41-4.46 (d, 1H), 4.25 (s), 3.87-3.92 (m, 2H), 3.67-3.75 (m), 3.56-3.60 (m), 3.30-3.44 (m), 2.97-3.06 (br m), 2.30-2.75 (br m), 0.81-2.28 (broad continuous multiplets) (spectra attached)

ESI-MS: 973.0 [M+H]⁺.

Example 7

Cyclosporine and Azathioprine Derivatives

Cyclosporine and azathioprine derivatives, such as the derivatives shown below, will be prepared essentially according to the method described for tacrolimus involving reaction of the parent drug with an acid chloride. It is well established that azathioprine reacts selectively at N-9 with electrophilic agents (Mishra et al., *Ind. J. Chem., Sec. B*, 26B:847-50 (1987)). Thus, in some aspects, azathioprine derivatives provided herein will be derivatized at N-9.

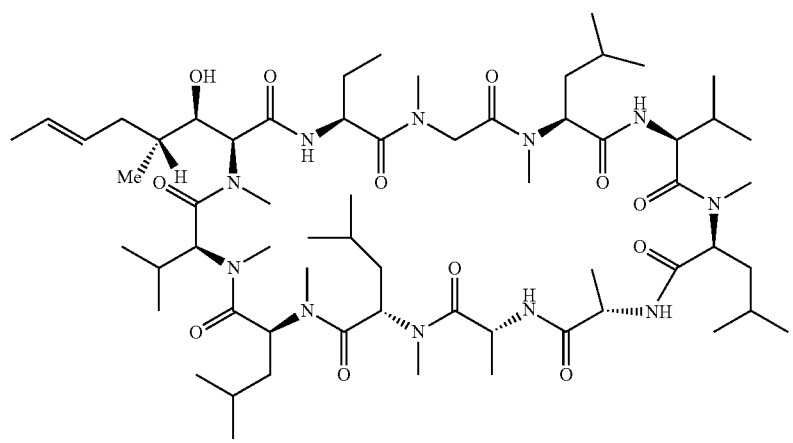
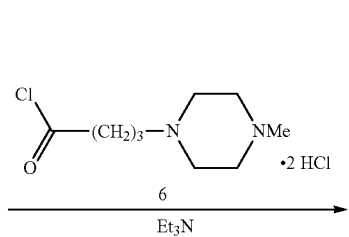
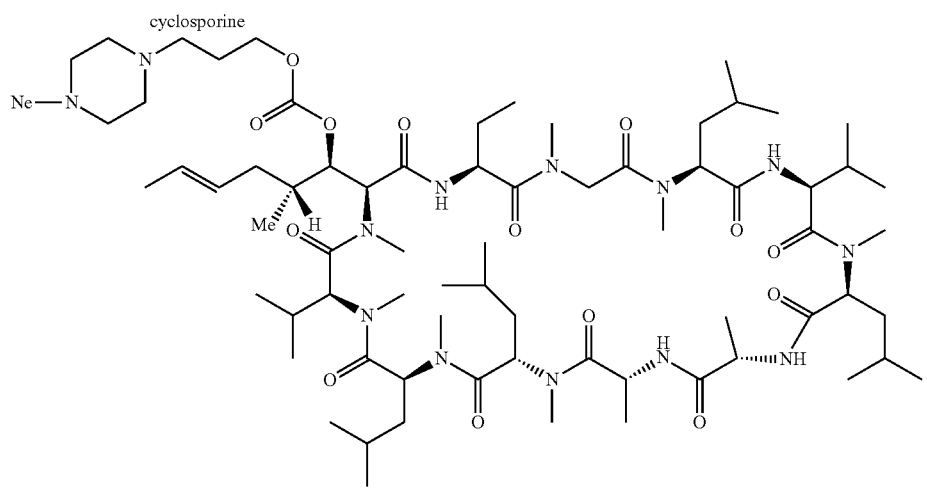

cyclosporine cyclosporine derivative

FIG. 7

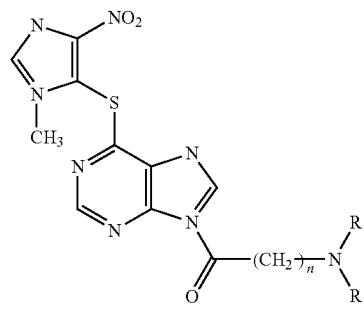

azathioprine derivatives

Example 8

Solubility of Weak-Base Derivatives

The solubility of the docetaxel derivatives was determined in acetate buffer at pH 5, which is the buffer used for active loading into LN. Compounds were dissolved in ethanol at 50 mg/ml (except TD2, which was dissolved at 25 mg/ml)). An aliquot was diluted 10-fold with 10 mM acetate buffer (pH 5) and the pH was checked and re-adjusted as necessary to reach pH 5. Alternatively, 10 mg of each compound was weighed into a glass vial, and 2 mL of 10 mM acetate buffer (pH 5) was added to the compound, followed by sonication of the suspension for 10 minutes. The precipitate was then removed using Microcon MY100 filters (MW cut-off 100,000 Da) and the filtrate analyzed by UPLC-UV for drug content. The measured solubilities are kinetic solubilities determined under non-equilibrium conditions.

Small (non membrane-permeabilizing) quantities of ethanol can optionally be used to increase aqueous solubility during loading. Thus, solubility data were generated in both buffer and buffer containing 10% (v/v) ethanol. The aqueous solubility of docetaxel derivatives (Table 2) varied significantly, with values ranging from about 20-500 times greater than that of docetaxel (Du et al., *Bioorganic & Medicinal Chemistry*, 15:6323-30 (2007)). Solubility decreased in the order N-methyl piperazino>piperidino>>morpholino. The solubility of the morpholino derivatives was significantly lower than that of the piperazino and piperidino derivatives.

TABLE 2

Aqueous solubility of docetaxel derivatives at pH 5 in the absence and presence of 10% ethanol.

| Prodrug | Solub. 10% EtOH (mg/ml) | Solub. in 10 mM acetate pH 5 (mg/ml) |
|---------|-------------------------|--------------------------------------|
| TD1     | 3.5                     | 1.7                                  |
| TD2     | 2.5                     | 2                                    |
| TD3     | 4.1                     | 2.5                                  |
| TD4     | —                       | 0.12                                 |
| TD5     | 0.3                     | 0.14                                 |
| TD6     | 1.5                     | 0.48                                 |
| TD7     | —                       | 1.9                                  |
| TD8     | —                       | 0.5                                  |
| TD9     | 2.3                     | 1                                    |
| TD10    | —                       | 3                                    |

The pKa of the amino group of TD1 was determined by acid-base titration to be 7.7, making it well suited for pH gradient loading into LN. As expected, the water solubility of the TD1 hydrochloride salt decreased with increasing pH (2.8 mg/ml at pH 4 and 1.7 mg/ml at pH 5).

Example 9

Stability of Weak-Base Derivatives

The chemical stability of the docetaxel derivatives was determined in aqueous solutions at different pH values and temperatures, and in biological media (mouse plasma). Aliquots of the docetaxel derivatives in acetonitrile were mixed with buffered citrate/HEPES (10 mM/10 mM) solutions at pH 4.0 and 7.5, or in mouse plasma in 1 mL glass HPLC sample vials sealed with Teflon-lined caps (final volume 0.25 ml, final docetaxel derivative concentration 50 µg/ml). Drug stability was determined 1, 4 and 24 hrs after incubation at 37° C. by UPLC-UV. At the indicated time points, a 3-fold excess of methanol/0.1% TFA was added to the sample. Citrate/HEPES buffered samples were analyzed by UHPLC as described above. For plasma samples, proteins precipitated by the addition of methanol/0.1% TFA pelleted by centrifugation at 14,000×g and supernatants were analyzed for the drug derivatives. Heparanized mouse plasma was diluted to 50% with 100 mM sodium-phosphate buffer to keep the pH constant throughout the experiment.

To be suitable for formulation in LN, derivatives must be stable at pH 4 (the pH present inside the LN carrier). In addition, prodrug derivatives should readily form the active drug under physiological conditions (e.g., at pH 7.4 and/or in the presence of endogenous enzymes) once released from the LN. Table 3 shows the hydrolytic stability of docetaxel derivatives at pH 4, pH 7.4, and in mouse plasma after 24 hours of incubation at 37° C. Among the C-2' amino ester docetaxel derivatives, TD1-4, TD7 and TD9 had adequate stability at pH 4. TD4 has extremely low solubility in water and incubation in plasma appeared to have no effect on TD9. TD1-3 and TD7 were selected for loading into LN and testing of such LN for drug release in vitro.

The results (Table 3 and FIG. 1) indicate that the derivatives are stable at the low pH values found inside LN (pH around 4) and are capable of undergoing rapid conversion into active drug following release from the LN carrier in vivo. The conversion to active drug is pH-dependent (faster at higher pH) and is significantly accelerated in the presence of hydrolytic enzymes present in biological fluids such as blood plasma.

TABLE 3

Prodrug levels (% remaining) after 24 hour incubation in pH 4 or 7.4 buffer or mouse plasma.

| | TD-1 | TD-2 | TD-3 | TD-4 | TD-5 | TD-6 | TD-7 | TD-8 | TD-9 |
|---|---|---|---|---|---|---|---|---|---|
| pH 4 | 94 | 99 | 99 | 98 | 81 | 68 | 94 | 78 | 99 |
| pH 7.4 | 23 | 59 | 69 | 92 | 64 | 18 | 13 | 36 | 65 |
| Plasma | 12 | 31 | 29 | 64 | 45 | 0 | 8 | 4 | 60 |

Example 10

Loading Efficiency

Piperazinyl ester (TD1-TD3), piperidine ester (TD7), and C-7 amino ester (TD10) derivatives of docetaxel, the N-methyl-piperazinyl butanoic acid and acetic acid ester derivatives of prednisone and the N-methyl-piperazinyl butanoic acid ester derivative of etoposide were tested for efficiency of loading into LN.

Preparation of LN

LN were prepared based on the ethanol procedure described by Boman et al., *Cancer Res*.; 54:2830-2833 (1994). Briefly, lipids (phospholipid/Chol, 55/45 molar ratio) were dissolved in ethanol and added slowly into an aqueous solution containing 350 mM ammonium sulfate at 60° C.; trace amounts of the lipid marker [$3^{H}$]CHE (0.15 μCi/mg total lipid) were co-dissolved with the other lipids in ethanol to prepare LN for release studies. The final ethanol concentration was 15% (v/v). The resulting LN dispersions were extruded at 60° C. through two stacked 100 nm polycarbonate filters (Nucleopore, Pleasanton, Calif.) using a heated thermobarrel extruder (Northern Lipids, Vancouver, Canada), as described by Hope et al., *Biochim. Biophys. Acta;* 812: 55-65 (1985). Residual ethanol and external ammonium sulfate were removed by tangential flow diafiltration at room temperature, and replaced with a 300 mM sucrose solution using a Midgee™ HOOP™ ultrafiltration cartridge (MW cutoff 100000; Amersham Biosciences). Quasi-elastic light scattering (QELS) was used to assess the size distribution of the extruded LN (target size 100±20 nm), using a NICOMP model 370 submicron particle sizer (Particle Sizing Systems, Santa Barbara, Calif.).

Drug Loading

The docetaxel, etoposide and prednisone derivatives were loaded into DSPC/Chol (55:45 mol %) LN using the ammonium sulfate-based remote-loading method described by Haran et al., *Biochim. Biophys. Acta;* 1151:201-15 (1993). Briefly, TD1 was dissolved at 2 mg/mL in 10 mM sodium acetate-buffered 300 mM sucrose (pH 5), the etoposide derivative was dissolved at 2.5 mg/ml 10 mM sodium acetate-buffered 300 mM sucrose (pH 5) and the prednisone derivative was dissolved at 7 mg/mL in 10 mM sodium acetate buffer (pH 5.3). The dissolved derivatives were added to pre-heated (60° C.) LN suspensions and the mixtures were incubated with stirring at 60° C. for the indicated times (typically 30 min). LN formulations are typically prepared at lipid concentrations between 5-10 mg/ml and drug-to-lipid weight ratios of 0.1-0.4 mg/mg. The unencapsulated docetaxel derivatives were removed by tangential flow diafiltration using a Midgee™ HOOP™ ultrafiltration cartridge (MW cutoff 100000; Amersham Biosciences) or size exclusion chromatography. The external solution was replaced with non-buffered physiological saline solution and the sample concentrated as needed. Drug-loaded LN formulations for in vivo studies were sterilized by filtration through 0.2 μm filters (Nalgene) and subsequently stored at 4° C. TD-1 was also loaded into LN composed of DPPC/chol (55:45 mol %) and DMPC/chol (55:45 mol %).

Figure 2:
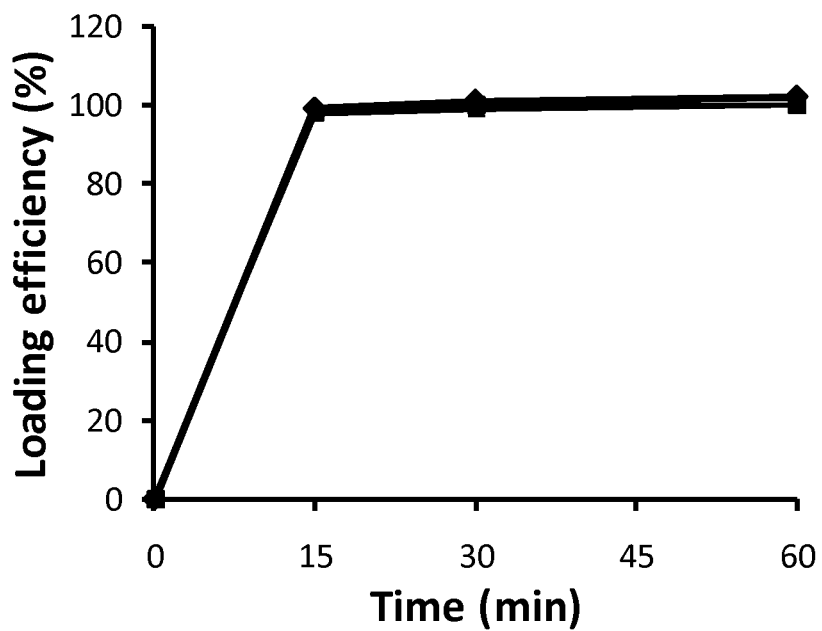
FIG. 2. Loading of docetaxel derivatives into LN. The derivatives were loaded by incubation at 60° C. into DSPC/chol LN through a pH (ammonium ion) gradient formed by 300 mM ammonium sulfate within LN and an external ammonium sulfate-free medium buffered at pH 5. (A) Loading efficiency of the docetaxel prodrug TD1 at prodrug-to-lipid ratios of 0.1 wt/wt (■), 0.2 wt/wt (♦) and 0.4 wt/wt (▲). (B) Loading efficiency of C-2'-piperazinyl ester (TD1-TD3), C-2'-piperidine ester (TD7), and C-7-amino ester (TD10) derivatives of docetaxel incubated with DSPC/Chol LN at a prodrug-to-lipid ratio of 0.2 wt/wt.
Figure 2:
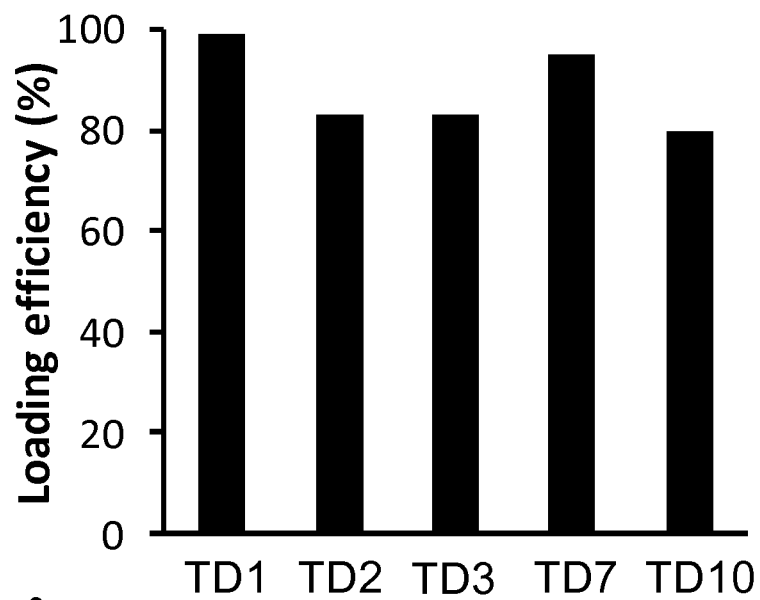
Figure 3:
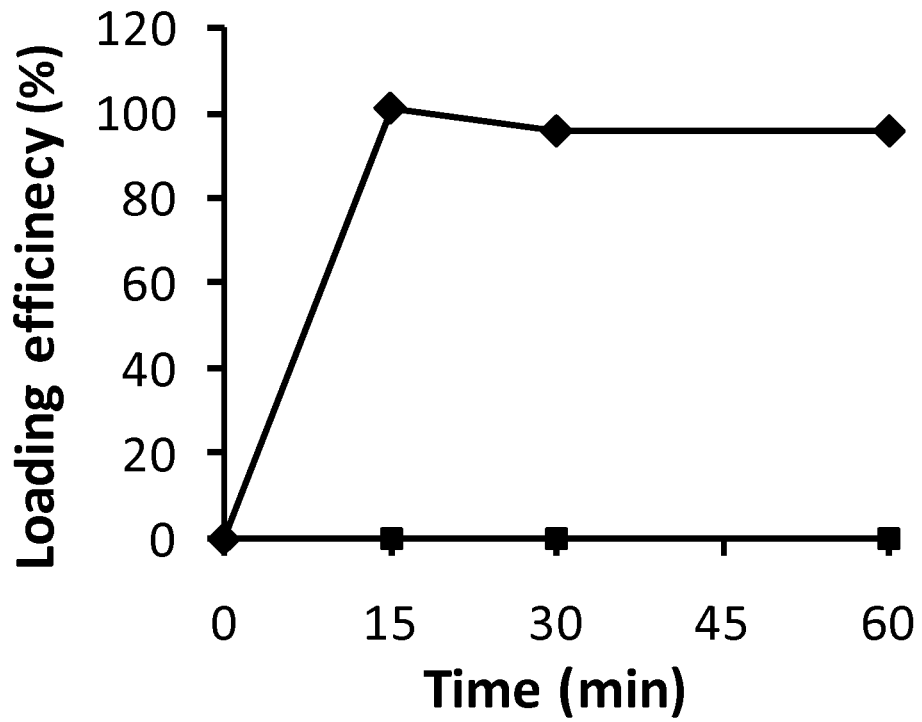
FIG. 3. Loading of prednisone derivatives. into LN. The derivatives were loaded at 60° C. into DSPC/Chol LN through a pH (ammonium ion) gradient formed by 300 mM ammonium sulfate within LN and an external ammonium sulfate-free medium buffered at pH 5. (A): Loading efficiency of an N-methyl-piperazinyl butanoic acid ester derivative of prednisone (♦) relative to the parent drug (■) at a drug-to-lipid ratio of 0.12 wt/wt. The prednisone derivative did not spontaneously partition into the LN bilayer; thus, there was no measurable amount of the derivative associated with the LN carrier in the absence of the ammonium sulfate (pH) gradient. (B): Loading efficiencies of prednisone derivatives with varying linker lengths after 15 min of incubation at 60° C.: comparison of N-methyl-piperazinyl butanoic acid ester (B) and N-methyl-piperazinyl acetic acid ester (E) derivatives. The N-methyl-piperazinyl butanoic acid ester derivative showed 100% loading efficiency whereas the N-methyl-piperazinyl acetic acid ester derivative showed about 75% loading efficiency.
Figure 3:
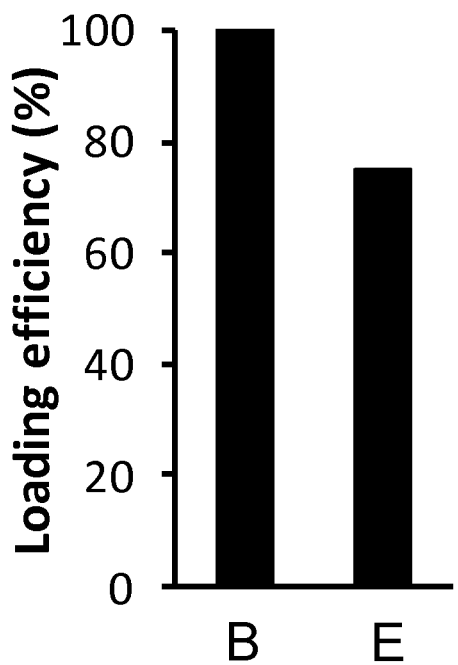
Figure 4:
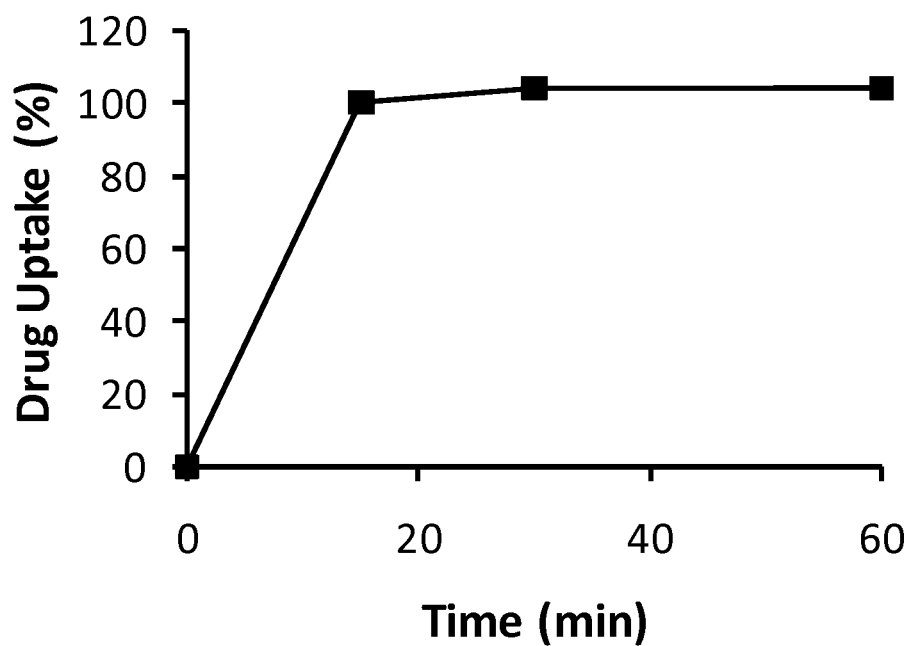
FIG. 4. Loading of an etoposide derivative into LN. The N-methyl-piperazinyl butanoic acid ester derivative was loaded at 60° C. into DMPC/Chol LN through a pH (ammonium ion) gradient formed by 300 mM ammonium sulfate within LN and an external ammonium sulfate-free medium buffered at pH 5. The derivative showed 100% loading efficiency within 15 min of incubation at 60° C. at a drug-to-lipid ratio of 0.16 wt/wt.

Loading efficiencies were determined by quantitating both prodrug and lipid levels before and after separation of external (non-encapsulated) prodrug from LN encapsulated prodrug by size exclusion chromatography using Sephadex G50 spin columns and comparing the respective prodrug/lipid ratios. Phospholipid concentrations were determined by the phosphorus assay of Fiske and Subbarow, *J. Biol. Chem.*; 66: 375-379 (1925), and cholesterol concentrations were quantitated using an enzymatic colorimetric assay (Wako Chemicals, Richmond, Va.). Derivative concentrations were determined by ultra high performance liquid chromatography (UHPLC) as described herein. Conversion of the prodrug into parent drug during loading was monitored as well. Results are shown in FIGS. 2 (docetaxel derivatives), 3 (prednisone derivatives) and 4 (etoposide derivative).

Example 11

Stability of LN Formulations

LN-derivative formulations with different lipid compositions (DSPC/Chol, DPPC/Chol and DMPC/Chol, each at 55/45 mol % and a derivative/lipid ratio of 0.2 wt/wt) were prepared at a derivative concentration of 3 mg/ml in 0.9% physiological saline. The LN formulations were sterile filtered and sterile-filled into 5 mL glass vials and the vials were stoppered and capped and then stored at 7° C. At various time points (once a week within the first month and monthly thereafter) over a 4 month period, formulations were analyzed for LN size (QELS), derivative retention (Sephadex G-50 spin column method) and derivative integrity. Results are summarized in FIG. 5A-C. All three formulations were extremely stable; prodrug release was not detectable (FIG. 5B); the average size and size distribution of the LN formulations remained unchanged (FIG. 5C); and prodrug hydrolysis was less than 4% (3.5-3.8%, FIG. 5A). No other degradation products were observed. The data demonstrates the feasibility of developing wet LN formulations. Freezing of formulations is another alternative.

LN prepared using an ammonium sulfate gradient technique have an intravesicular pH of approximately 4.0 (Maurer-Spurej et al., *Biochim. Biophys. Acta*, 1416:1-10 (1999)). In light of the significantly greater stability of the derivatives at pH 4 relative to pH 7.4 (see Table 2, above), LN encapsulation greatly improves the hydrolytic stability of the entrapped derivatives compared with the derivatives in aqueous solution. For example, at pH 4 TD1 has a hydrolysis half-life of about 49 days (or 7 weeks). In contrast, less than 3% of the encapsulated TD1 was converted into docetaxel over a period of 4 months (16 weeks). Cryo-TEM microscopy revealed that the prodrug is precipitated in the LN interior and as a consequence has significantly higher stability.

Figure 5:
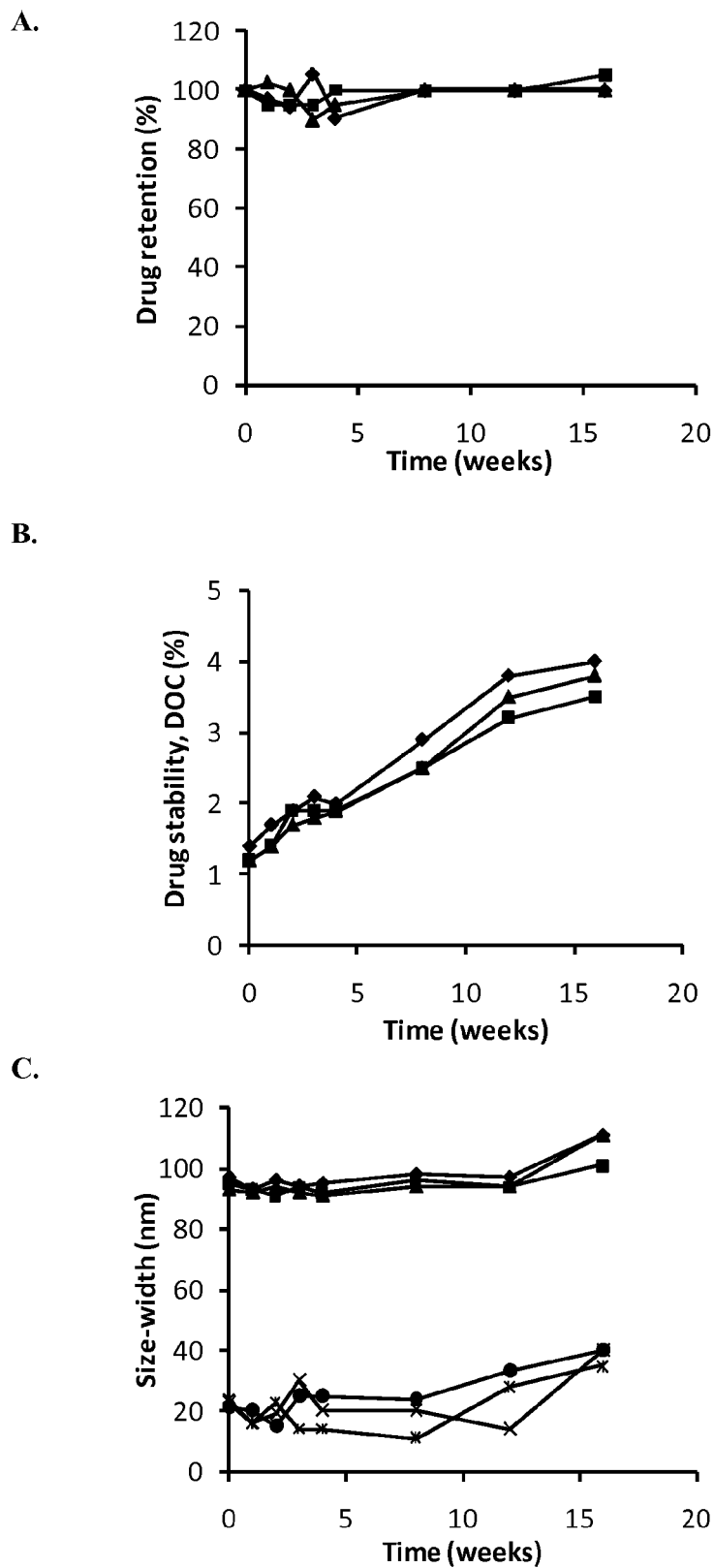
FIG. 5. Formulation stability. The stability of LN-docetaxel derivative formulations with different lipid compositions (DSPC/Chol, DPPC/Chol and DMPC/Chol) was followed over a period of 4 months upon cold storage (7° C.). The prodrug-to-lipid ratios of the formulations were 0.2 wt/wt. (A) Prodrug hydrolysis; increase of parent drug (docetaxel) was determined by UHPLC, (B) percentage of the prodrug retained in LN, (C) LN size and polydispersity measured by dynamic light scattering.
Figure 6:
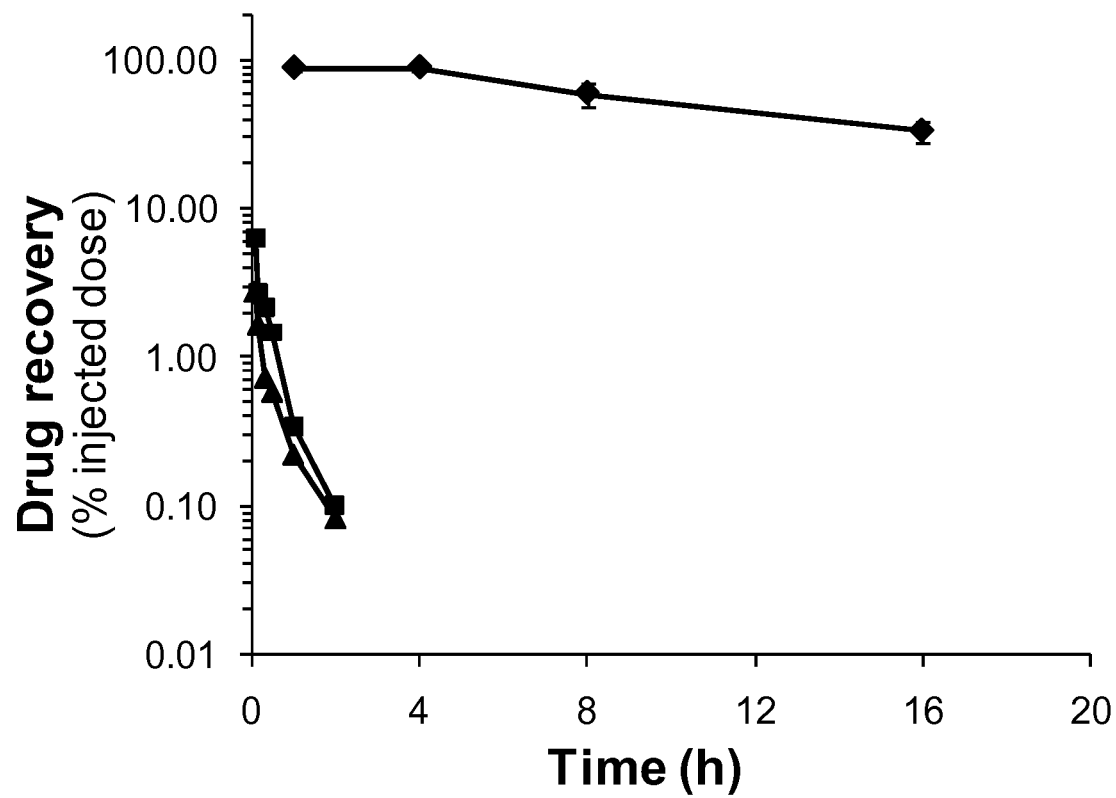
FIG. 6. Plasma elimination profiles of Taxotere™ (▲), TD1 formulated in the same manner as Taxotere™ (ethanol/polysorbate 80/physiological saline) (■) and DSPC/Chol LN formulation of TD1 (prodrug-to-lipid ratio 0.2 (wt/wt)) (♦) following i.v. administration in mice. Female Swiss Webster mice were injected intravenously with a single dose of the various formulations at equimolar docetaxel doses (20 mg/kg docetaxel). Prodrug levels in plasma were determined by UHPLC-MS. Data points represent mean values±standard deviation from each group of mice (n=4).

The rate at which TD1 (formulated in the same manner as Taxotere™ and in LN) and Taxotere™ are removed from the blood circulation was investigated following i.v. administration of the formulations to Swiss Webster mice. The mice were injected intravenously with a single bolus injection of equimolar doses (20 mg/kg docetaxel) of the formulations, and plasma levels of TD1 and docetaxel were determined by UHPLC-MS. Results are shown in FIG. 5. Both docetaxel/Taxotere™ and the derivative had plasma circulation half-lives of minutes and plasma concentrations below detectable levels by 2 h (FIG. 6). In contrast, formulation of the derivative in DSPC/Chol LN extended the circulation half-life from minutes to 10-12 hours with two orders of magnitude higher plasma concentrations (FIG. 6). Approximately 24% of the injected dose remained in the circulation at 16 h. The elimination of the LN-formulated derivative appears to be primarily determined by the elimination rate of the LN carrier. The data demonstrate that LN formulations of the derivative are stable in circulation and can achieve circulation half-lives that favor efficient drug accumulation at therapeutic targets.

Example 12

Release of Drug Derivatives from LN in vitro

The activity of LN-based drugs is highly dependent on the release rate of the drug from the carrier. For example, if the drug rapidly leaks out of the LN carrier, LN reaching the disease site will carry little or no drug and there will be negligible therapeutic benefit over the free drug. On the other hand, if a drug is released too slowly from the LN, the amount of drug reaching the disease site will never reach therapeutic concentrations. The main determinants of drug retention/release are the lipid composition of the LN carrier and the intra-vesicular form of the drug. The use of unsaturated lipids or lipids with shorter acyl chains favours faster drug release. Drug precipitation inside the LN can increase drug retention. Whether drug derivatives precipitate within LN can be determined by viewing LN formulations using cryo-TEM and/or other methods known in the art.

In vitro release of docetaxel derivatives from LN was assessed in mouse plasma. Drug retention was determined by comparison of the initial prodrug-to-lipid ratio with the prodrug-to-lipid ratios found at different time points. Docetaxel derivatives were encapsulated in DSPC/chol, DPPC/Chol and DMPC/Chol LN (55:45 mol %) containing trace amounts of the radiolabeled lipid marker $^3$H-cholesterylhexadecylether ($^3$H—CHE). LN formulations were mixed with mouse plasma at a final lipid concentration of 0.75 mg/ml, followed by incubation at 37° C. At various time points, aliquots were taken and run over Sephadex G-50 spin columns to remove the unentrapped prodrug (Pick, *Arch. Biochem. Biophys.*, 212:186-194 (1981)). The derivative and lipid concentrations in the eluates were determined by UHPLC and liquid scintillation counting, respectively.

Figure 7:
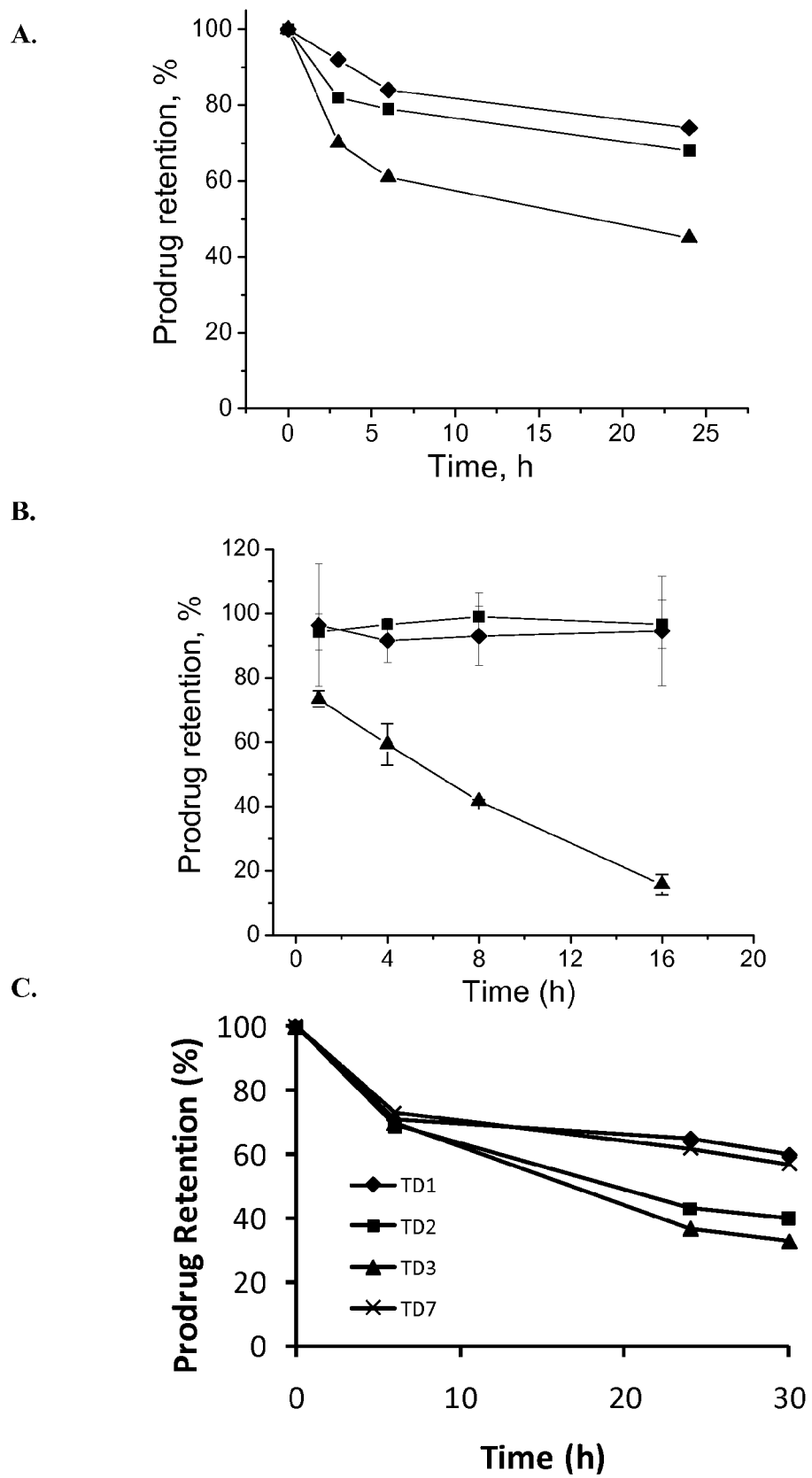
FIG. 7. Plasma drug retention profiles. Retention of the docetaxel derivative TD1 in DSPC/Chol (♦), DPPC/Chol (■) and DMPC/Chol (▲) LN formulations was determined in vitro (A) and in vivo (B). In vitro retention of TD1 in DSPC/chol LN was compared with other docetaxel derivatives (TD2-3 and TD7) formulated in DSPC/chol LN at the same drug-to-lipid ratio in mouse plasma (C). LN formulations containing trace amounts of the radiolabeled lipid [$^3$H]-CHE were injected intravenously into female Swiss Webster mice at a docetaxel equivalent dose of 20 mg/kg or incubated in vitro at 37° C. in mouse plasma. Plasma samples taken at the indicated time points were analyzed for lipid and prodrug content by liquid scintillation counting and UHPLC, respectively. For the in vitro retention studies unentrapped (released) drug was removed from the plasma samples by size exclusion chromatography using Sephadex G50 spin columns prior to analysis of lipid and drug content. Data points represent means±standard deviations (n=4).

FIG. 7A shows the percent retention of TD1 in LN, defined as the derivative/lipid (or prodrug/lipid) ratio found in the sample at a specified time point divided by the initial drug-to-lipid ratio. Both DSPC/Chol and DPPC/Chol LN show no or little release over the 16 h time course of the experiment. DMPC/Chol LN released the prodrug with a halftime of about 6 hours with 16% of the prodrug remaining entrapped 16 h post injection. Comparison of the retention profiles of DSPC/Chol LN formulations loaded at 0.1 and 0.2 mg/mg shows that drug retention is not dependent on prodrug-to-lipid ratio. In vitro release studies performed in mouse plasma are in good agreement with the in vivo studies (FIG. 7B). The increase in release seen with DMPC/Chol LN compared to DSPC and DPPC/Chol LN is consistent with a decrease in membrane permeability in going from DMPC, which has the shortest acyl chains (C14) to the longer chain lipids. FIG. 7C shows the in vitro retention properties of TD1 in DSPC/chol LN relative to other docetaxel derivatives (TD2-3 and TD7) formulated in DSPC/chol at the same prodrug-to-lipid ratio. All derivatives were efficiently retained. TD7 was released at a rate mirroring that of TD1, whereas TD2 and TD3 were released at a slightly faster rate (percent release is defined as 100 minus percent retention). The in vitro and in vivo data demonstrate that weak base derivatives can be efficiently retained in LN and that release rates can be regulated by varying the lipid composition of LN carriers.

Example 13

Pharmacokinetics and in vivo Drug Release

The pharmacokinetics (PK) of LN-encapsulated docetaxel derivatives were compared to the PK of Taxotere™, the commercial docetaxel formulation, and derivatives formulated in the same manner as Taxotere™. Taxotere™ and similarly formulated derivatives were formulated as described in the prescribing information for Taxotere™ (Sanofi-Aventis, U.S.) using ethanol/polysorbate 80/physiological saline solution to dissolve the drug. The docetaxel derivative was encapsulated in DSPC/chol, DPPC/Chol and DMPC/Chol LN (55:45 mol %) at a drug-to-lipid ratio of 0.2 wt/wt using the ammonium sulfate loading technique. The lipid components contained trace amounts (0.15 μCi/mg lipid) of the lipid marker [$^3$H]CHE, allowing monitoring of the elimination of both the prodrug and the LN carrier from circulation.

The PK and in vivo release studies were based on 4 time points (1, 4, 8 and 16 hrs) and 4 mice per time point. All formulations were administered i.v. via the lateral tail vein at docetaxel (or equivalent docetaxel) doses of 20 mg/kg and volumes based on subject weight (10 mL/kg). At various times, mice were anesthetized with ketamine/xylazine and blood was collected by cardiac puncture and placed into EDTA microtainer tubes. Animals were terminated immediately after blood collection. Plasma was separated from whole blood by centrifugation at 1,000 g for 10 min. Plasma proteins were precipitated by the addition of 150 μl of ice-cold methanol acidified with 0.1% TFA to 50 μl of plasma. The methanolic solutions were centrifuged for 30 min at 15,000×g at 4° C. to pellet the proteins and the supernatant was analyzed for docetaxel and drug derivatives by UHPLC. For LN formulations, 25-50 μl of plasma was added to scintillation fluid (PicoFluor 40, Perkin Elmer) and analyzed for lipid levels ([$^3$H]-CHE radioactivity) by scintillation counting. The percentage of prodrug remaining in LN (drug retention) was calculated by dividing the prodrug/lipid ratios found in plasma samples by those of the injected LN formulations, taken as 100%. Results are shown in FIG. 7B. As free docetaxel and docetaxel derivatives were cleared at much faster rates than LN-encapsulated forms, the prodrug/lipid ratios recovered from the plasma samples can be regarded as a direct indication of the amount of prodrug remaining encapsulated in LN.

Example 14

In vitro Anticancer Activity

The ability of the derivative to form the active drug (bioconversion) was further investigated by measuring the anticancer activity of TD1 in vitro relative to the parent compound (docetaxel). Anticancer activity was evaluated against a panel of 3 human cancer cell lines, including the ovarian cancer cell line ES-2, the prostate cancer cell line PC3 and the breast cancer cell line MDA435/LCC6 (BC Cancer Research Centre, Vancouver, BC) (Fields and Lancaster, *Am. Biotechnol. Lab.*, 11:48-50 (1993); Nakayama et al., *J. Immunol. Methods*, 204:205-208 (1997)). Cytotoxicity was determined using the Alamar Blue assay after a 72-h drug exposure period. Briefly, cells were incubated in 96 well plates at 37° C. for 72 hrs in the presence of varying amounts of TD1 or the parent drug (dissolved in DMSO); at the end of the incubation period, Alamar Blue solution was added to all of the wells (20 μl/well, 10% of culture volume). The plates were returned to the incubator for 4 h; sample fluorescence was determined at $\lambda_{ex}$=530 nm and $\lambda_{em}$=590 nm. Viability was calculated according to: Cell viability (%)=$(F_{plus\ drug}-F_{background})/(F_{minus\ drug}-F_{background})*100$, where $F_{plus\ drug}$ is the fluorescence reading in the presence of drug, $F_{minus\ drug}$ the cell control in the absence of drug and $F_{background}$ the background fluorescence (media alone). IC$_{50}$ values (nM) were calculated by fitting a sigmoidal curve to the concentration-viability plot and are presented in Table 4. TD1 was as active as docetaxel, indicating that the prodrug was readily converted into the active compound.

TABLE 4

In vitro cytotoxicity (IC$_{50}$ values) of docetaxel and docetaxel derivative.

| Cell line | IC$_{50}$ (nM) Docetaxel | IC$_{50}$ (nM) Derivative |
|---|---|---|
| PC-3 (prostate cancer) | 1 | 0.5 |
| MDA-MB-435/LCC6 (breast canc | <0.1 | <0.1 |
| ES-2 (ovarian cancer) | 0.1 | 0.1 |

Example 15

In vivo Anticancer Activity

The anticancer efficacy of LN-docetaxel derivative formulations was evaluated in a subcutaneous xenograft model of human breast cancer (MDA-MB-435/LCC6) after a single bolus injection. Murine MDA-MB-435/LCC6 cells were cultured in DMEM with 2 mM L-glutamine and 10% FBS at 37° C. in 5% CO$_2$ environment. Female RAG2-M mice were inoculated with 5×10$^6$ (50 μL) cells subcutaneously on the right hind flank. Once tumors reached a size of 100-150 mm$^3$, animals were randomized into groups (6 animals per group) and injected with a single i.v. bolus injection of Taxotere™ at a dose of 25 mg/kg or LN formulations of TD1 (DSPC/Chol, DPPC/Chol and DMPC/Chol at 55:45 mol % and a prodrug/lipid weight ratio 0.2 wt/wt) at three different doses (31.25 mg/kg, 50 mg/kg and 110 mg/kg, which is corresponds to 25, 40 and 88 mg/kg docetaxel). Tumor growth and animal weights were measured every third day. Tumor growth was monitored by measuring tumor dimensions with digital calipers and tumor volumes were calculated according to the equation length×(width)÷2 with the length (mm) being the longer axis of the tumor. Tumors were allowed to grow to a maximum of 700 mm$^3$ before termination; animals with ulcerated tumors were terminated.

The effectiveness of the treatment was assessed through comparison of established parameters of anticancer activity, including: tumor growth inhibition (optimal % T/C); tumor growth delay (T-C); difference in time for treated and control tumors to double in size; and NCI score (Plowman J, Dykes D J, Hollingshead M, Simpson-Herren L, Alley M C. 1997. Human tumor xenograft models in NCI drug development. In: Teicher B A, editor. Anticancer drug development guide: Preclinical screening, clinical trials, and approval. Totowa: Humana Press, Inc. pp 101-125). In addition, any drug-related deaths (within 15 days of last dose and low tumor burden) were recorded, as well as the maximum weight loss (mean of group). % T/C values and NCI scores were calculated as follows: changes in tumor volumes for each treated (T) and control (C) were calculated for each day tumors were measured by subtracting the median tumor volume on the day of first treatment from the median tumor volume on the specified observation day. The resulting values were used to calculate percent T/C according to % T/C=(ΔT/ΔC)×100. The optimal (minimum) value was used to quantitate antitumor activity. An NCI score of 0 is assigned to an optimal % T/C>42 and means that the treatment is ineffective. A score of 1 is assigned to optimal % T/C values 1-42 and indicates tumor growth is inhibited (Capdeville et al., *Nature Reviews Drug Discovery*, 1:493-502 (2002)).

Figure 8:
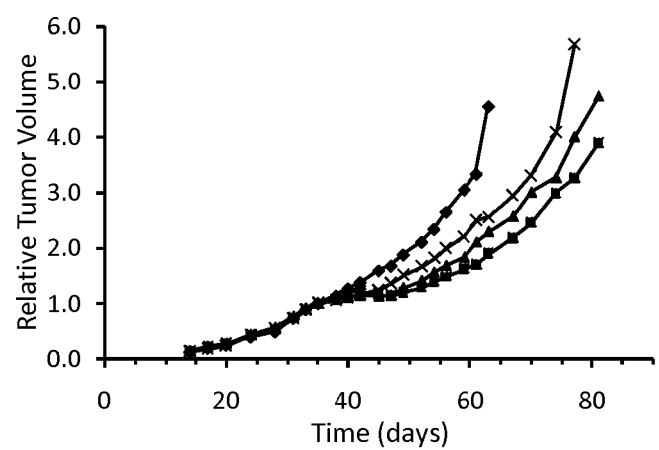
FIG. 8. Anticancer efficacy. Response of subcutaneous MDA435/LCC6 human breast carcinoma xenografts to treatment with Taxotere™ and LN-encapsulated TD1 in Rag2M mice. (A) Treatment with various LN formulations to determine the effect of lipid composition on efficacy. LN formulations (prodrug-to-lipid ratio 0.2 wt/wt) were composed of DSPC/Chol (■), DPPC/Chol (▲) and DMPC/Chol (✘) and administered at a docetaxel equivalent dose of 40 mg/kg. Untreated control received a saline injection (♦). (B) Dose-response for the DSPC/Chol LN formulation (prodrug-to-lipid ratio 0.2 wt/wt) administered at docetaxel equivalent doses of 25 (x), 40 (✘) and 88 (▲) mg/kg. Untreated controls received a saline injection (♦). Taxotere™ at 25 mg/kg docetaxel was included for comparison (■). (C) Comparison of Taxotere™ with the 88 mg/kg DSPC/Chol LN formulation. Tumor growth curves are shown with standard deviations. Treatment was initiated at day 35 with a single i.v. bolus injection. Points represent the means of relative tumor volumes (ratio of the tumor volume measured at a given time point to the tumor volume measured at the treatment day); mean values for 6 mice per group are presented.
Figure 8:
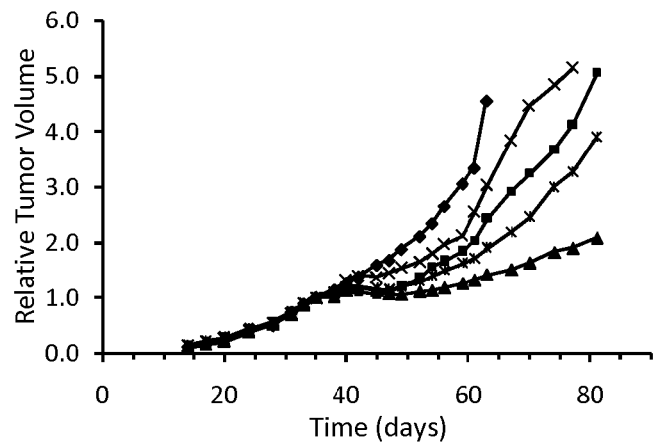
Figure 8:
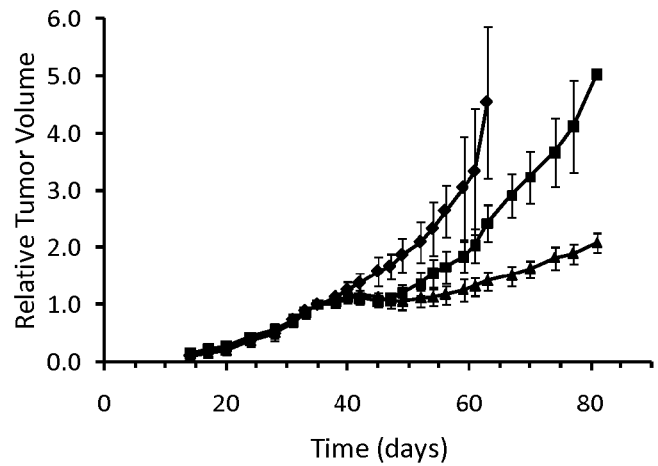
Figure 9:
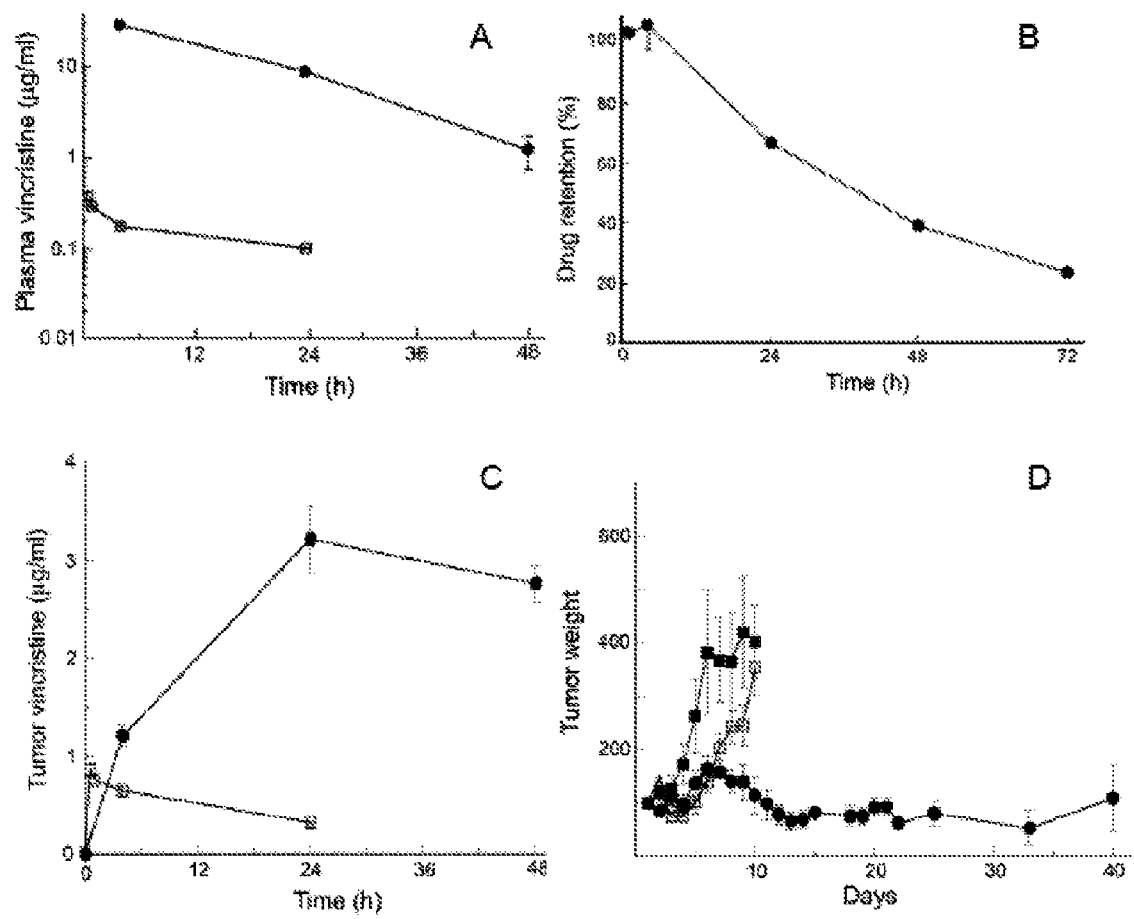
FIG. 9. In vivo kinetics and anticancer activity of free vincristine (VCR) (2 mg/kg) and vincristine (2 mg/kg) encapsulated in 100 nm egg sphingomyelin/cholesterol LN injected i.v. in SCID mice bearing A431 tumors. (8A) Concentration profile of free VCR (□) and LN formulated VCR (●) in blood plasma over time. Free VCR is rapidly removed from circulation, whereas LN formulated VCR has an extended circulation half-life. (8B) Release of free VCR (●) from LN formulations (% retention) over time. LN formulated VCR exhibits a sustained release profile in circulation. (8C) Tumor concentration (μg/ml) of VCR over time after administration of free VCR (□) and LN formulated VCR (●). The extended half-life and sustained release profile of LN formulated VCR results in increasing tumor accumulation of VCR over time. (8D) Anticancer activity of free VCR (□) and LN formulated VCR (●) relative to saline control (■). LN formulated VCR has significantly greater anticancer activity than the free compound. Nano-liposomal formulations increase the amount of drug reaching sites of tumor growth and prolongs the duration of exposure to therapeutically active levels of drug, resulting in increased antitumor activity.

The influence of lipid composition of the LN carrier on the efficacy of encapsulated TD1 is illustrated in FIG. 8A. DSPC/Chol, DPPC/Chol and DMPC/Chol LN formulations (TD1-to-lipid ratio 0.2 wt/wt) were administered at a docetaxel equivalent dose of 40 mg/kg. The DSPC/Chol formulation inhibited tumor growth most effectively, followed by DPPC/Chol and DMPC/Chol (least active) formulations. Antitumor efficacy is highly correlated with the release rate, with the formulation that exhibits the slowest release rate being the most active.

The therapeutic activity of the DSPC/Chol formulation (TD1-to-lipid ratio 0.2 wt/wt) was determined at 3 different doses (25, 40 and 88 mg/kg docetaxel) in comparison to 25 mg/kg Taxotere™/docetaxel. At equimolar doses (25 mg/kg docetaxel) Taxotere™ was slightly more efficacious than the LN formulation. However, the LN formulation can be administered at doses much higher than the MTD of Taxotere™. At these doses, DSPC/Chol LN formulations were significantly more efficacious (FIG. 8B). The most significant tumor growth suppression was observed at 88 mg/kg docetaxel with optimal % T/C value of 5% and a tumor growth delay (T-C) of 29 days compared to 9 days for Taxotere™ (Table 5). The results demonstrate that LN formulations are potentially much more effective than Taxotere™.

TABLE 5

Summary of antitumor activity and tolerability parameters of the docetaxel derivative TD1.

| Treatment | Docetaxel Dose (mg/kg) | Anti-Tumor Activity | | | Toxicity | |
|---|---|---|---|---|---|---|
| | | % T/C[a] | T-C[b] (days) | NCI Score | DRD[c] | MWL[d] |
| Taxotere ™ | 25 | 10 | 9 | 1 | 0/6 | −3.2 |
| DSPC/Chol | 25 | 55 | 4 | 0 | 0/6 | −0.9 |
| DSPC/Chol | 40 | 21 | 11 | 1 | 0/6 | −2.9 |
| DSPC/Chol | 88 | 5 | 29 | 1 | 0/6 | −3.8 |
| DPPC/Chol | 40 | 21 | 9 | 1 | 0/6 | Not observed |
| DMPC/Chol | 40 | 42 | 4 | 0 | 0/6 | −2.9 |

[a]Optimal % T/C. A % T/C >42 has an NCI score of 0 (inactive) and a % T/C from 1-42 has an NCI score of 1 (stands for tumor inhibition).
[b]Tumor growth delay (difference in time for treated and control tumors to double in size).
[c]Drug related deaths (DRD).
[d]Maximum mean weight loss per treatment group in percent (%), n = 6.

Example 16

Tolerability Studies

Tolerability studies were aimed at establishing the maximum tolerated dose (MTD) and the dose range for use in efficacy studies (efficacy studies were based on a single i.v. injection). Single dose MTD studies were performed in immune-compromised SCID/Rag2-M mice (also used for the efficacy studies) using LN-encapsulated TD1, TD1 formulated in the same manner as docetaxel in Taxotere™, and Taxotere™. The studies were based on administration of a single dose and relied on 3 mice/group and a dose escalation strategy based on three dose levels for the derivative and Taxotere and five dose levels for the LN formulations (DSPC/Chol 55:45 mol % at a prodrug/lipid weight ratio of 0.2 mg/mg). All formulations were injected i.v. via the lateral tail vein in a volume of 200 μl/20 g mouse.

Mice were monitored daily for signs of toxicity over a period of 14 days following drug administration. Tolerability was assessed by changes in body weight as well as behavioral parameters. The MTD was defined as the dose that results in ~15% loss in body weight and does not cause lethality. Body weights of individual mice were measured every second day over the course of the study. If weight loss was not a good predictor of tolerability, the dose where no animals needed to be terminated due to toxicity was used.

The results are summarized in Table 6. The single dose MTD of Taxotere™ was 29 mg/kg while the MTD of TD1 was 16 mg/kg (MTD in docetaxel equivalents corresponding to 20 mg/kg prodrug). TD1 showed acute toxicity (lethality) at a docetaxel equivalent dose of 20 mg/kg. The acute toxicity appeared to be related to drug precipitation following injection. In contrast, LN-encapsulated TD1 (DSPC/Chol 55:45 mol % LN, prodrug/lipid weight ratio 0.2 mg/mg) was well tolerated with no signs of toxicity (no significant changes in body weight and behavioral parameters) at docetaxel equivalent doses as high as 88 mg/kg (Table 6). The MTD of the LN formulation is at least 3 times higher than that of Taxotere™ (29 mg/kg) demonstrating that it is much better tolerated (less toxic) and thus can be administered at higher and more efficacious doses. Vehicle (polysorbate 80/physiological saline) alone had no adverse effects.

TABLE 6

Maximum tolerated doses (MTD) of Taxotere ™.

| Drug | Dose (mg/kg) | Max Wt Loss (%) | DRD | Clin. Observations | MTD (mg/kg) |
|---|---|---|---|---|---|
| Taxotere | 22 | −2.1 | 0/3 | | |
| | 29 | −2.7 | 0/3 | | 29 |
| | 36 | + | 1/3 | | |
| LN formulation | 40 | −0.4 | 0/3 | | |
| | 52 | −3.5 | 0/3 | | |
| | 64 | −0.6 | 0/3 | | |
| | 76 | −1.5 | 0/3 | | |
| | 88 | −2.3 | 0/3 | | >88 |
| Derivative | 16 | + | 0/3 | | 16 |
| | 20 | | 1/1 | Acute toxicity | |
| | 24 | | 3/3 | Acute toxicity | |

DRD: drug-related death

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:
1. A method of loading liposomal nanoparticles, the method comprising:
providing a suspension of liposomal nanoparticles in an external medium, the liposomal nanoparticles having an aqueous interior; and combining the suspension of liposomal nanoparticles with a docetaxel derivative represented by:

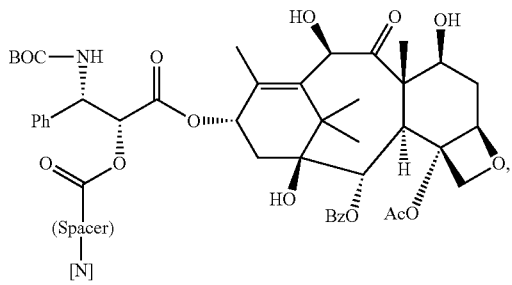

wherein —C(═O)-(Spacer)-[N] is selected from the group consisting of:

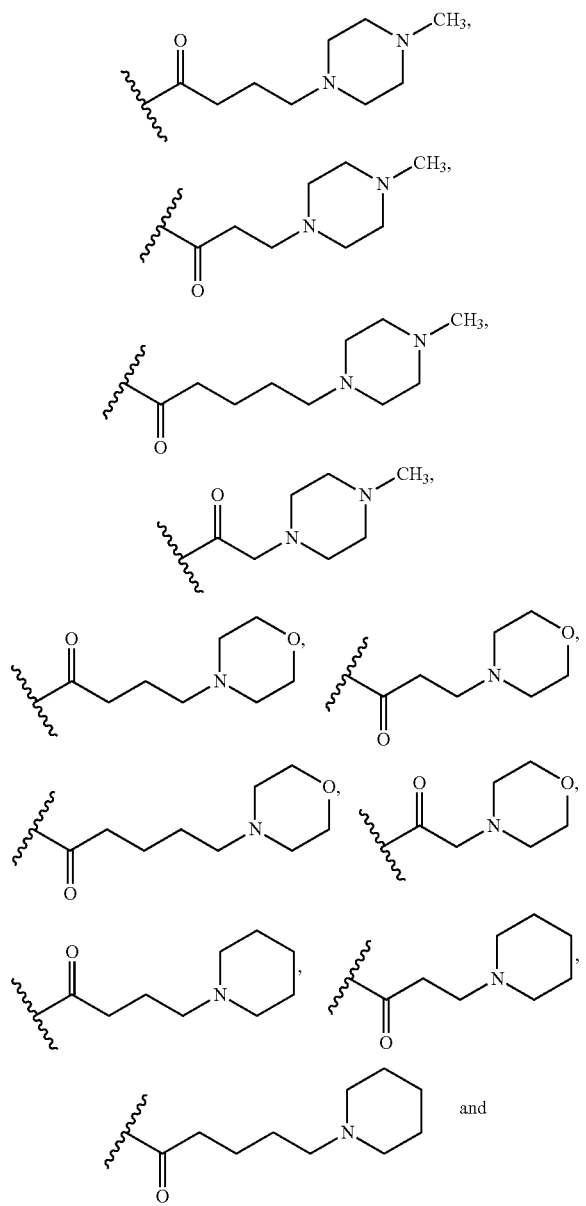

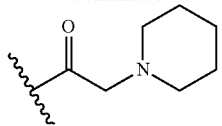

to provide a mixture, wherein the aqueous interior of the liposomal nanoparticles has an acidic pH relative to the external medium.

2. The method of claim 1, wherein the aqueous interior comprises a citrate buffer.

3. The method of claim 1, wherein the external medium comprises sucrose at a concentration of 300 mM.

4. The method of claim 1, wherein the liposomal nanoparticles comprise a phosphatidylcholine containing saturated $C_{14}$-$C_{22}$ carbon chains.

5. The method of claim 4, wherein the liposomal nanoparticles further comprise a sterol.

6. The method of claim 5, wherein the liposomal nanoparticles comprise the sterol and the phosphatidylcholine in a molar ratio of from 0.1:1 to 1:1.

7. The method of claim 1, wherein the liposomal nanoparticles are less than about 0.05 microns in size.

8. The method of claim 1, wherein the liposomal nanoparticles are between about 0.1 and 0.5 microns in size.

9. The method of claim 1, comprising maintaining the mixture at a temperature equal to or higher than 60° C. for a period of from 5 minutes to 2 hours.

10. The method of claim 1, wherein the loading efficiency is at least about 50%.

11. The method of claim 10, wherein the loading efficiency is at least about 85%.

12. The method of claim 1, further comprising replacing the external medium.

13. The method of claim 1, further comprising lyophilizing the suspension of liposomal nanoparticles.

14. The method of claim 1, wherein:
the liposomal nanoparticles are between about 0.1 and 0.5 microns in size,
the liposomal nanoparticles comprise the sterol and the phosphatidylcholine in a molar ratio of from 0.1:1 to 1:1;
the aqueous interior comprises a citrate buffer; and
combining the suspension of liposomal nanoparticles with a docetaxel derivative comprises:
dissolving the docetaxel derivative to form an aqueous solution, wherein the aqueous solution comprises sucrose at a concentration of 300 mM;
combining the aqueous solution with the suspension of liposomal nanoparticles to provide a mixture; and
maintaining the mixture at a temperature equal to or higher than 60° C. for a period of from 5 minutes to 2 hours.

15. A method of loading a docetaxel derivative into liposomal nanoparticles, the method comprising:
forming a docetaxel derivative or a pharmaceutically acceptable salt thereof;
providing a suspension of liposomal nanoparticles in an external medium, the liposomal nanoparticles having an aqueous interior, wherein the aqueous interior of the liposomal nanoparticles has an acidic pH relative to the external medium; and actively loading a docetaxel derivative or pharmaceutically acceptable salt thereof into the liposomal nanoparticles; wherein the docetaxel derivative has the structure:

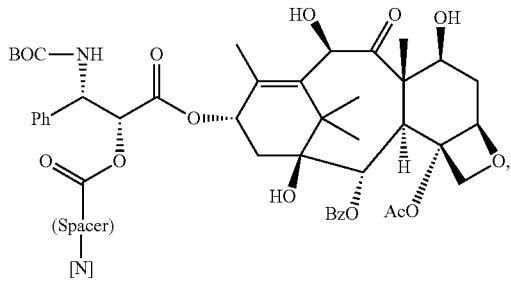

wherein —C(=O)-(Spacer)-[N] is selected from the group consisting of:

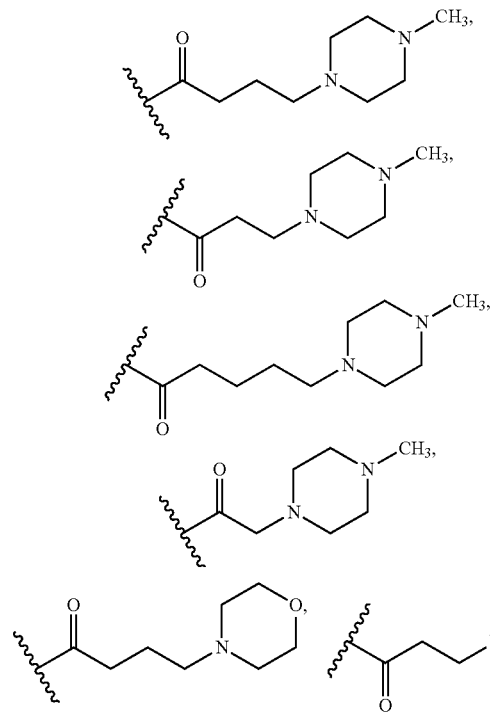

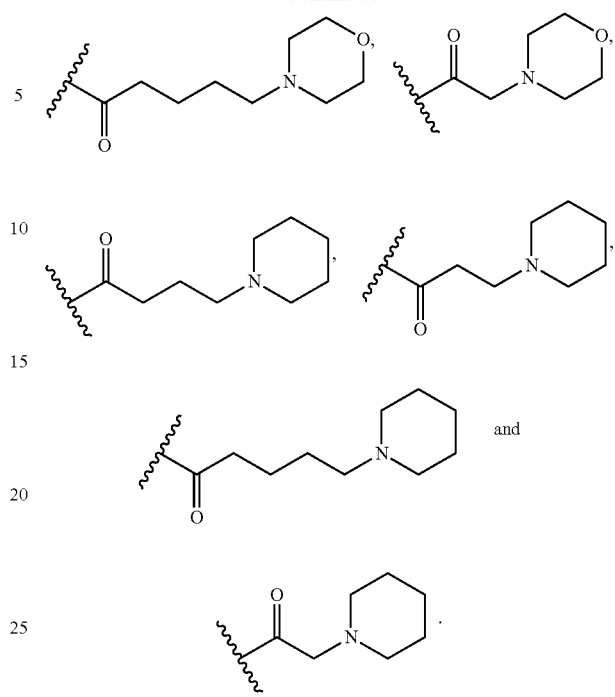

16. The method of claims 1 or 15, wherein the docetaxel derivative has the structure:

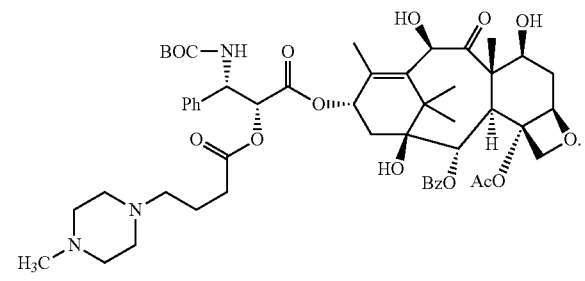

17. A loaded liposomal nanoparticle prepared according to the method of claim 1 or 15.

* * * * *